United States Patent
Concino et al.

(10) Patent No.: US 10,722,559 B2
(45) Date of Patent: Jul. 28, 2020

(54) MANNOSE-6-PHOSPHATE BEARING PEPTIDES FUSED TO LYSOSOMAL ENZYMES

(71) Applicant: Shire Human Genetic Therapies, Inc., Lexington, MA (US)

(72) Inventors: Michael F. Concino, Lexington, MA (US); Bettina Strack-Logue, Lexington, MA (US); Muthuraman Meiyappan, Lexington, MA (US); Angela W. Norton, Lexington, MA (US); Bohong Zhang, Lexington, MA (US); Andrea Iskenderian, Lexington, MA (US); Lieh Yoon Low, Lexington, MA (US); Dianna Lundberg, Lexington, MA (US); Alla Romashko, Lexington, MA (US); Hicham Naimy, Lexington, MA (US)

(73) Assignee: Shire Human Genetic Therapies, Inc., Lexington, MA (US)

( * ) Notice: Subject to any disclaimer, the term of this patent is extended or adjusted under 35 U.S.C. 154(b) by 155 days.

(21) Appl. No.: 15/503,223

(22) PCT Filed: Aug. 11, 2015

(86) PCT No.: PCT/US2015/044713
§ 371 (c)(1),
(2) Date: Feb. 10, 2017

(87) PCT Pub. No.: WO2016/025519
PCT Pub. Date: Feb. 18, 2016

(65) Prior Publication Data
US 2017/0232076 A1 Aug. 17, 2017

Related U.S. Application Data

(60) Provisional application No. 62/036,082, filed on Aug. 11, 2014.

(51) Int. Cl.
| | |
|---|---|
| *A61K 38/47* | (2006.01) |
| *A61K 38/43* | (2006.01) |
| *A61K 38/17* | (2006.01) |
| *A61K 38/20* | (2006.01) |
| *A61K 38/30* | (2006.01) |
| *C07K 14/47* | (2006.01) |
| *C07K 14/54* | (2006.01) |
| *C07K 14/65* | (2006.01) |
| *C12N 9/12* | (2006.01) |

(52) U.S. Cl.
CPC .......... *A61K 38/47* (2013.01); *A61K 38/1709* (2013.01); *A61K 38/204* (2013.01); *A61K 38/30* (2013.01); *A61K 38/43* (2013.01); *C07K 14/4703* (2013.01); *C07K 14/4705* (2013.01); *C07K 14/5412* (2013.01); *C07K 14/65* (2013.01); *C12N 9/1288* (2013.01); *C12Y 207/08017* (2013.01); *C07K 2319/06* (2013.01); *C12Y 302/0105* (2013.01)

(58) Field of Classification Search
CPC combination set(s) only.
See application file for complete search history.

(56) References Cited

U.S. PATENT DOCUMENTS

| 10,300,113 B2 * | 5/2019 | LeBowitz .............. A61K 38/30 |
| 2012/0021436 A1 | 1/2012 | Meiyappan et al. |

FOREIGN PATENT DOCUMENTS

| WO | WO 2003/057179 A2 | 7/2003 |
| WO | WO-2011/163652 A2 | 12/2011 |
| WO | WO2012/157136 | 11/2012 |
| WO | WO2013/055888 | 4/2013 |
| WO | WO 2014/085621 A1 | 6/2014 |

OTHER PUBLICATIONS

Stephane Lefrancois et al. (The Lysosomal Transport of Prosaposin Requires the Conditional Interaction of Its Highly Conserved D Domain with Sphingomyelin. The Journal of Biological Chemistry vol. 277, No. 19, Issue of May 10, pp. 17188-17199, 2002 (Year: 2002).*

Qing Zhao et al. Identification of a Novel Sequence Involved in Lysosomal Sorting of the Sphingolipid Activator Protein Prosaposin. (The Journal of Biological Chemistry vol. 275, No. 32, Issue of Aug. 11, pp. 24829-24839, 2000) (Year: 2000).*

Hashimoto, et al., N-terminal Deletion Mutants of Insulin-like Growth Factor-II (IGF-11) Show $Thr^7$ and $Leu^8$ Important for Binding to Insulin and IGF-1 Receptors and $Leu^8$ Critical for All IGF-11 Functions, The Journal of Biological Chemistry, vol. 270, No. 30, pp. 18013-18018, 1995.

(Continued)

*Primary Examiner* — Kagnew H Gebreyesus
(74) *Attorney, Agent, or Firm* — Proskauer Rose LLP; Fangli Chen; Julio J. Mendez

(57) ABSTRACT

A targeted therapeutic including a lysosomal enzyme and a lysosomal targeting moiety that is a peptide containing at least one N-linked glycosylation site. Methods of producing the targeted therapeutic may include nucleotide acids encoding the same and host cells co-expressing GNPT. Pharmaceutical compositions comprising the targeted therapeutic and methods of using the same to treat a lysosomal storage disease.

11 Claims, 40 Drawing Sheets
Specification includes a Sequence Listing.

(56) References Cited

OTHER PUBLICATIONS

Zhou, et al., Mannose 6-phosphate quantitation in glycoproteins using high-pH anion-exchange chromatography with pulsed amperometric detection, Analytical Biochemistry, vol. 306, No. 2, pp. 163-170, Jul. 15, 2002.

Jong, et al., Measuring Urinary Glycosaminoglycans in the Presence of Protein: An Improved Screening Procedure for Mucopolysaccharidoses Based on Dimethylmethylene Blue, Clinical Chemistry, vol. 38, No. 6, pp. 803-807, 1992.

Lawrence et al., Disease-Specific Non-Reducing End Carbohydrate Biomarkers for Mucopolysaccharidoses, Nat Chem Biol., vol. 8, No. 2, pp. 197-204, Jan. 8, 2012.

Barnes, et al., Extensive Mannose Phosphorylation on Leukemia Inhibitory Factor (LIF) Controls Its Extracellular Levels by Multiple Mechanisms, The Journal of Biological Chemistry, vol. 286, No. 28, pp. 24855-24864, Jul. 15, 2011.

Blanchard, et al., The Mannose 6-Phosphate/Insulin-like Growth Factor II Receptor Is a Nanomolar Affinity Receptor for Glycosylated Human Leukemia Inhibitory Factor, The Journal of Biological Chemistry, vol. 273, No. 33, pp. 20886-20893, Aug. 14, 1998.

Blanchard, et al., The Mannose 6-Phosphate/Insulin-Like Growth Factor II Receptor Mediates Internalization and Degradation of Leukemia Inhibitory Factor But Not Signal Transduction*, The Journal of Biological Chemistry, vol. 274, No. 35, pp. 24685-24693, Aug. 27, 1999.

Bockenhoff, et al., Comparison of Five Peptide Vectors for Improved Brain Delivery of the Lysosomal Enzyme Arylsulfatase A, The Journal of Neuroscience, vol. 34, No. 9, pp. 3122-3129, Feb. 26, 2014.

Duguay, et al., Post-Translational Processing of the Insulin-Like Growth Factor-2 Precursor, The Journal of Biological Chemistry, vol., 279, No. 29, pp. 18443-18451, Jul. 17, 1998.

Grubb, et al., New Strategies for Enzyme Replacement Therapy for Lysosomal Storage Diseases, Rejuvenation Research, vol. 13, No. 2-3, pp. 229-236, Jan. 1, 2010.

Kirkegaard., Emerging Therapies and Therapeutic Concepts for Lysosomal Storage Diseases, Expert Opinion on Orphan Drugs, vol. 1, No. 5, May 1, 2013, pp. 385-404, May 1, 2013.

Liu, et al., Synthesis of Novel Bivalent Mimetic Ligands for Mannose-6-Phosphate Receptors, Bioorganic & Medicinal Chemistry Letters, vol. 23, No. 8, pp. 2328-2331, Feb. 24, 2013.

Muro, New Biotechnological and Nanomedicine Strategies for Treatment of Lysosomal Storage Disorders, Wiley Interdisciplinary Review: Nanomedicine and Nanobiotechnology, vol. 2, No. 2, pp. 189-204, Mar. 28, 2010.

Shimizu, et al., Characterization of Human Melanotransferrin Expressed in Recombinant Baculorvirus Infected Insect Cells, The University of Winnipeg, pp. 1-104, Dec. 1, 1993.

Zhu, et al., Glycoengineered Acid A-Glucosidase With Improved Efficacy at Correcting the Metabolic Aberrations and Motor Function Deficits in a Mouse Model of Pompe Disease, Molecular Therapy, vol. 17, No. 6, pp. 954-963, Jun. 1, 2009.

* cited by examiner

M6P Content of Naglu-SapDC and Naglu-Lif Measured by PAD-HPLC Method

| Sample | M6P Content (mol /mol protein) |
|---|---|
| I2S | 1.91 |
| Naglu-SAPDC | 0.75 |
| GNPT / Naglu-SAPDC | 1.84 |
| Naglu-Lif | below detection |
| GNPT / Naglu-Lif | 1.07 |

FIG. 9

Anti-Naglu antibody Staining in Cerebral Cortex : Naglu-SapDC
(Positive staining neurons and glia cells were found in areas of cerebral cortex)

Anti-Naglu antibody Staining in the Liver : Naglu-SapDC

Anti-Naglu antibody Staining in the Liver : Naglu-Lif

SEQUENCE LISTING

```
<160> NUMBER OF SEQ ID NOS: 30

<210> SEQ ID NO 1
<211> LENGTH: 720
<212> TYPE: PRT
<213> ORGANISM: Homo sapiens

<400> SEQUENCE: 1

Asp Glu Ala Arg Glu Ala Ala Val Arg Ala Leu Val Ala Arg Leu
1               5                   10                  15

Leu Gly Pro Gly Pro Ala Ala Asp Phe Ser Val Ser Val Glu Arg Ala
                20                  25                  30

Leu Ala Ala Lys Pro Gly Leu Asp Thr Tyr Ser Leu Gly Gly Gly
                35              40                  45

Ala Ala Arg Val Arg Val Arg Gly Ser Thr Gly Val Ala Ala Ala
    50                  55                  60

Gly Leu His Arg Tyr Leu Arg Asp Phe Cys Gly Cys His Val Ala Trp
65                  70                  75                  80

Ser Gly Ser Gln Leu Arg Leu Pro Arg Pro Leu Pro Ala Val Pro Gly
                85                  90                  95

Glu Leu Thr Glu Ala Thr Pro Asn Arg Tyr Arg Tyr Gln Asn Val
                100                 105                 110

Cys Thr Gln Ser Tyr Ser Phe Val Trp Trp Asp Trp Ala Arg Trp Glu
                115                 120                 125

Arg Glu Ile Asp Trp Met Ala Leu Asn Gly Ile Asn Leu Ala Leu Ala
                130                 135                 140

Trp Ser Gly Gln Glu Ala Ile Trp Gln Arg Val Tyr Leu Ala Leu Gly
145                 150                 155                 160

Leu Thr Gln Ala Glu Ile Asn Glu Phe Phe Thr Gly Pro Ala Phe Leu
                165                 170                 175

Ala Trp Gly Arg Met Gly Asn Leu His Thr Trp Asp Gly Pro Leu Pro
                180                 185                 190

Pro Ser Trp His Ile Lys Gln Leu Tyr Leu Gln His Arg Val Leu Asp
                195                 200                 205

Gln Met Arg Ser Phe Gly Met Thr Pro Val Leu Pro Ala Phe Ala Gly
                210                 215                 220

His Val Pro Glu Ala Val Thr Arg Val Phe Pro Gln Val Asn Val Thr
225                 230                 235                 240

Lys Met Gly Ser Trp Gly His Phe Asn Cys Ser Tyr Ser Cys Ser Phe
                245                 250                 255

Leu Leu Ala Pro Glu Asp Pro Ile Phe Pro Ile Ile Gly Ser Leu Phe
                260                 265                 270

Leu Arg Glu Leu Ile Lys Glu Phe Gly Thr Asp His Ile Tyr Gly Ala
                275                 280                 285

Asp Thr Phe Asn Glu Met Gln Pro Pro Ser Ser Glu Pro Ser Tyr Leu
                290                 295                 300

Ala Ala Ala Thr Thr Ala Val Tyr Glu Ala Met Thr Ala Val Asp Thr
```

```
            305                 310                 315                 320
        Glu Ala Val Trp Leu Leu Gln Gly Trp Leu Phe Gln His Gln Pro Gln
                        325                 330                 335

Phe Trp Gly Pro Ala Gln Ile Arg Ala Val Leu Gly Ala Val Pro Arg
                        340                 345                 350

Gly Arg Leu Leu Val Leu Asp Leu Phe Ala Glu Ser Gln Pro Val Tyr
                        355                 360                 365

Thr Arg Thr Ala Ser Phe Gln Gly Gln Pro Phe Ile Trp Cys Met Leu
                370                 375                 380

His Asn Phe Gly Gly Asn His Gly Leu Phe Gly Ala Leu Glu Ala Val
        385                 390                 395                 400

Asn Gly Gly Pro Glu Ala Ala Arg Leu Phe Pro Asn Ser Thr Met Val
                        405                 410                 415

Gly Thr Gly Met Ala Pro Glu Gly Ile Ser Gln Asn Glu Val Val Tyr
                        420                 425                 430

Ser Leu Met Ala Glu Leu Gly Trp Arg Lys Asp Pro Val Pro Asp Leu
                        435                 440                 445

Ala Ala Trp Val Thr Ser Phe Ala Ala Arg Arg Tyr Gly Val Ser His
                450                 455                 460

Pro Asp Ala Gly Ala Ala Trp Arg Leu Leu Leu Arg Ser Val Tyr Asn
        465                 470                 475                 480

Cys Ser Gly Glu Ala Cys Arg Gly His Asn Arg Ser Pro Leu Val Arg
                        485                 490                 495

Arg Pro Ser Leu Gln Met Asn Thr Ser Ile Trp Tyr Asn Arg Ser Asp
                        500                 505                 510

Val Phe Glu Ala Trp Arg Leu Leu Leu Thr Ser Ala Pro Ser Leu Ala
                        515                 520                 525

Thr Ser Pro Ala Phe Arg Tyr Asp Leu Leu Asp Leu Thr Arg Gln Ala
                530                 535                 540

Val Gln Glu Leu Val Ser Leu Tyr Tyr Glu Glu Ala Arg Ser Ala Tyr
        545                 550                 555                 560

Leu Ser Lys Glu Leu Ala Ser Leu Leu Arg Ala Gly Gly Val Leu Ala
                        565                 570                 575

Tyr Glu Leu Leu Pro Ala Leu Asp Glu Val Leu Ala Ser Asp Ser Arg
                        580                 585                 590

Phe Leu Leu Gly Ser Trp Leu Glu Gln Ala Arg Ala Ala Ala Val Ser
                        595                 600                 605

Glu Ala Glu Ala Asp Phe Tyr Glu Gln Asn Ser Arg Tyr Gln Leu Thr
                610                 615                 620

Leu Trp Gly Pro Glu Gly Asn Ile Leu Asp Tyr Ala Asn Lys Gln Leu
        625                 630                 635                 640

Ala Gly Leu Val Ala Asn Tyr Tyr Thr Pro Arg Trp Arg Leu Phe Leu
                        645                 650                 655

Glu Ala Leu Val Asp Ser Val Ala Gln Gly Ile Pro Phe Gln Gln His
                        660                 665                 670

Gln Phe Asp Lys Asn Val Phe Gln Leu Glu Gln Ala Phe Val Leu Ser
                        675                 680                 685

Lys Gln Arg Tyr Pro Ser Gln Pro Arg Gly Asp Thr Val Asp Leu Ala
                        690                 695                 700

Lys Lys Ile Phe Leu Lys Tyr Tyr Pro Arg Trp Val Ala Gly Ser Trp
        705                 710                 715                 720

<210> SEQ ID NO 2
```

<211> LENGTH: 743
<212> TYPE: PRT
<213> ORGANISM: Homo sapiens

<400> SEQUENCE: 2

```
Met Glu Ala Val Ala Val Ala Ala Val Gly Val Leu Leu Leu Ala
1               5                   10                  15

Gly Ala Gly Gly Ala Ala Gly Asp Glu Ala Arg Glu Ala Ala Val
                20                  25                  30

Arg Ala Leu Val Ala Arg Leu Leu Gly Pro Gly Pro Ala Ala Asp Phe
                35                  40                  45

Ser Val Ser Val Glu Arg Ala Leu Ala Ala Lys Pro Gly Leu Asp Thr
50                  55                  60

Tyr Ser Leu Gly Gly Gly Ala Ala Arg Val Arg Val Arg Gly Ser
65                  70                  75                  80

Thr Gly Val Ala Ala Ala Gly Leu His Arg Tyr Leu Arg Asp Phe
                85                  90                  95

Cys Gly Cys His Val Ala Trp Ser Gly Ser Gln Leu Arg Leu Pro Arg
                100                 105                 110

Pro Leu Pro Ala Val Pro Gly Glu Leu Thr Glu Ala Thr Pro Asn Arg
                115                 120                 125

Tyr Arg Tyr Tyr Gln Asn Val Cys Thr Gln Ser Tyr Ser Phe Val Trp
                130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
                165                 170                 175

Arg Val Tyr Leu Ala Leu Gly Leu Thr Gln Ala Glu Ile Asn Glu Phe
                180                 185                 190

Phe Thr Gly Pro Ala Phe Leu Ala Trp Gly Arg Met Gly Asn Leu His
                195                 200                 205

Thr Trp Asp Gly Pro Leu Pro Pro Ser Trp His Ile Lys Gln Leu Tyr
210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
                260                 265                 270

Cys Ser Tyr Ser Cys Ser Phe Leu Leu Ala Pro Glu Asp Pro Ile Phe
                275                 280                 285

Pro Ile Ile Gly Ser Leu Phe Leu Arg Glu Leu Ile Lys Glu Phe Gly
                290                 295                 300

Thr Asp His Ile Tyr Gly Ala Asp Thr Phe Asn Glu Met Gln Pro Pro
305                 310                 315                 320

Ser Ser Glu Pro Ser Tyr Leu Ala Ala Thr Thr Ala Val Tyr Glu
                325                 330                 335

Ala Met Thr Ala Val Asp Thr Glu Ala Val Trp Leu Leu Gln Gly Trp
                340                 345                 350

Leu Phe Gln His Gln Pro Gln Phe Trp Gly Pro Ala Gln Ile Arg Ala
                355                 360                 365

Val Leu Gly Ala Val Pro Arg Gly Arg Leu Leu Val Leu Asp Leu Phe
                370                 375                 380

Ala Glu Ser Gln Pro Val Tyr Thr Arg Thr Ala Ser Phe Gln Gly Gln
```

```
            385                 390                 395                 400
Pro Phe Ile Trp Cys Met Leu His Asn Phe Gly Gly Asn His Gly Leu
                405                 410                 415

Phe Gly Ala Leu Glu Ala Val Asn Gly Gly Pro Glu Ala Ala Arg Leu
            420                 425                 430

Phe Pro Asn Ser Thr Met Val Thr Gly Met Ala Pro Glu Gly Ile
            435                 440                 445

Ser Gln Asn Glu Val Val Tyr Ser Leu Met Ala Glu Leu Gly Trp Arg
        450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
        515                 520                 525

Ile Trp Tyr Asn Arg Ser Asp Val Phe Glu Ala Trp Arg Leu Leu Leu
        530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
        595                 600                 605

Val Leu Ala Ser Asp Ser Arg Phe Leu Leu Gly Ser Trp Leu Glu Gln
        610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
        675                 680                 685

Gly Ile Pro Phe Gln Gln His Gln Phe Asp Lys Asn Val Phe Gln Leu
        690                 695                 700

Glu Gln Ala Phe Val Leu Ser Lys Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp
            740

<210> SEQ ID NO 3
<211> LENGTH: 524
<212> TYPE: PRT
<213> ORGANISM: Homo sapiens

<400> SEQUENCE: 3

Met Tyr Ala Leu Phe Leu Leu Ala Ser Leu Leu Gly Ala Ala Leu Ala
1               5                   10                  15
```

```
Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
        35                  40                  45

Leu Gln Thr Val Trp Asn Lys Pro Thr Val Lys Ser Leu Pro Cys Asp
    50                  55                  60

Ile Cys Lys Asp Val Val Thr Ala Ala Gly Asp Met Leu Lys Asp Asn
65                  70                  75                  80

Ala Thr Glu Glu Ile Leu Val Tyr Leu Lys Thr Cys Asp Trp
                85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
        115                 120                 125

Gly Glu Val Cys Ser Ala Leu Asn Leu Cys Glu Ser Leu Gln Lys His
    130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
            165                 170                 175

Leu Leu Leu Tyr Pro Gln Asp Gly Pro Arg Ser Lys Pro Gln Pro Lys
        180                 185                 190

Asp Asn Gly Asp Val Cys Gln Asp Cys Ile Gln Met Val Thr Asp Ile
    195                 200                 205

Gln Thr Ala Val Arg Thr Asn Ser Thr Phe Val Gln Ala Leu Val Glu
210                 215                 220

His Val Lys Glu Glu Cys Asp Arg Leu Gly Pro Gly Met Ala Asp Ile
225                 230                 235                 240

Cys Lys Asn Tyr Ile Ser Gln Tyr Ser Glu Ile Ala Ile Gln Met Met
            245                 250                 255

Met His Met Gln Pro Lys Glu Ile Cys Ala Leu Val Gly Phe Cys Asp
        260                 265                 270

Glu Val Lys Glu Met Pro Met Gln Thr Leu Val Pro Ala Lys Val Ala
    275                 280                 285

Ser Lys Asn Val Ile Pro Ala Leu Glu Leu Val Glu Pro Ile Lys Lys
290                 295                 300

His Glu Val Pro Ala Lys Ser Asp Val Tyr Cys Glu Val Cys Glu Phe
305                 310                 315                 320

Leu Val Lys Glu Val Thr Lys Leu Ile Asp Asn Asn Lys Thr Glu Lys
            325                 330                 335

Glu Ile Leu Asp Ala Phe Asp Lys Met Cys Ser Lys Leu Pro Lys Ser
        340                 345                 350

Leu Ser Glu Glu Cys Gln Glu Val Val Asp Thr Tyr Gly Ser Ser Ile
    355                 360                 365

Leu Ser Ile Leu Leu Glu Glu Val Ser Pro Glu Leu Val Cys Ser Met
370                 375                 380

Leu His Leu Cys Ser Gly Thr Arg Leu Pro Ala Leu Thr Val His Val
385                 390                 395                 400

Thr Gln Pro Lys Asp Gly Gly Phe Cys Glu Val Cys Lys Lys Leu Val
            405                 410                 415

Gly Tyr Leu Asp Arg Asn Leu Glu Lys Asn Ser Thr Lys Gln Glu Ile
        420                 425                 430

Leu Ala Ala Leu Glu Lys Gly Cys Ser Phe Leu Pro Asp Pro Tyr Gln
```

```
                435                 440                 445
Lys Gln Cys Asp Gln Phe Val Ala Glu Tyr Glu Pro Val Leu Ile Glu
            450                 455                 460

Ile Leu Val Glu Val Met Asp Pro Ser Phe Val Cys Leu Lys Ile Gly
465                 470                 475                 480

Ala Cys Pro Ser Ala His Lys Pro Leu Leu Gly Thr Glu Lys Cys Ile
                485                 490                 495

Trp Gly Pro Ser Tyr Trp Cys Gln Asn Thr Glu Thr Ala Ala Gln Cys
            500                 505                 510

Asn Ala Val Glu His Cys Lys Arg His Val Trp Asn
            515                 520

<210> SEQ ID NO 4
<211> LENGTH: 120
<212> TYPE: PRT
<213> ORGANISM: Homo sapiens

<400> SEQUENCE: 4

Asp Gly Gly Phe Cys Glu Val Cys Lys Lys Leu Val Gly Tyr Leu Asp
1               5                   10                  15

Arg Asn Leu Glu Lys Asn Ser Thr Lys Gln Glu Ile Leu Ala Ala Leu
            20                  25                  30

Glu Lys Gly Cys Ser Phe Leu Pro Asp Pro Tyr Gln Lys Gln Cys Asp
        35                  40                  45

Gln Phe Val Ala Glu Tyr Glu Pro Val Leu Ile Glu Ile Leu Val Glu
    50                  55                  60

Val Met Asp Pro Ser Phe Val Cys Leu Lys Ile Gly Ala Cys Pro Ser
65                  70                  75                  80

Ala His Lys Pro Leu Leu Gly Thr Glu Lys Cys Ile Trp Gly Pro Ser
                85                  90                  95

Tyr Trp Cys Gln Asn Thr Glu Thr Ala Ala Gln Cys Asn Ala Val Glu
            100                 105                 110

His Cys Lys Arg His Val Trp Asn
        115                 120

<210> SEQ ID NO 5
<211> LENGTH: 202
<212> TYPE: PRT
<213> ORGANISM: Homo sapiens

<400> SEQUENCE: 5

Met Lys Val Leu Ala Ala Gly Val Val Pro Leu Leu Leu Val Leu His
1               5                   10                  15

Trp Lys His Gly Ala Gly Ser Pro Leu Pro Ile Thr Pro Val Asn Ala
            20                  25                  30

Thr Cys Ala Ile Arg His Pro Cys His Asn Asn Leu Met Asn Gln Ile
        35                  40                  45

Arg Ser Gln Leu Ala Gln Leu Asn Gly Ser Ala Asn Ala Leu Phe Ile
    50                  55                  60

Leu Tyr Tyr Thr Ala Gln Gly Glu Pro Phe Pro Asn Asn Leu Asp Lys
65                  70                  75                  80

Leu Cys Gly Pro Asn Val Thr Asp Phe Pro Pro Phe His Ala Asn Gly
                85                  90                  95

Thr Glu Lys Ala Lys Leu Val Glu Leu Tyr Arg Ile Val Val Tyr Leu
            100                 105                 110

Gly Thr Ser Leu Gly Asn Ile Thr Arg Asp Gln Lys Ile Leu Asn Pro
```

```
            115                 120                 125
Ser Ala Leu Ser Leu His Ser Lys Leu Asn Ala Thr Ala Asp Ile Leu
        130                 135                 140

Arg Gly Leu Leu Ser Asn Val Leu Cys Arg Leu Cys Ser Lys Tyr His
145                 150                 155                 160

Val Gly His Val Asp Val Thr Tyr Gly Pro Asp Thr Ser Gly Lys Asp
                165                 170                 175

Val Phe Gln Lys Lys Leu Gly Cys Gln Leu Leu Gly Lys Tyr Lys
            180                 185                 190

Gln Ile Ile Ala Val Leu Ala Gln Ala Phe
            195                 200

<210> SEQ ID NO 6
<211> LENGTH: 180
<212> TYPE: PRT
<213> ORGANISM: Homo sapiens

<400> SEQUENCE: 6

Ser Pro Leu Pro Ile Thr Pro Val Asn Ala Thr Cys Ala Ile Arg His
1               5                   10                  15

Pro Cys His Asn Asn Leu Met Asn Ala Ile Arg Ala Gln Leu Ala Ala
            20                  25                  30

Leu Asn Gly Ser Ala Asn Ala Leu Phe Ile Leu Tyr Tyr Thr Ala Gln
        35                  40                  45

Gly Glu Pro Phe Pro Asn Asn Leu Asp Lys Leu Cys Gly Pro Asn Val
    50                  55                  60

Thr Asp Phe Pro Pro Phe His Ala Asn Gly Thr Glu Lys Ala Lys Leu
65                  70                  75                  80

Val Glu Leu Tyr Arg Ile Val Val Tyr Leu Gly Thr Ser Leu Gly Asn
                85                  90                  95

Ile Thr Arg Asp Gln Lys Ile Leu Asn Pro Ser Ala Leu Ser Leu His
            100                 105                 110

Ser Lys Leu Asn Ala Thr Ala Asp Ile Leu Arg Gly Leu Leu Ser Asn
        115                 120                 125

Val Leu Cys Arg Leu Cys Ser Lys Tyr His Val Gly His Val Asp Val
    130                 135                 140

Thr Tyr Gly Pro Asp Thr Ser Gly Lys Asp Val Ala Gln Lys Ala Lys
145                 150                 155                 160

Leu Gly Cys Gln Leu Leu Gly Lys Tyr Lys Gln Ile Ile Ala Val Leu
                165                 170                 175

Ala Gln Ala Phe
            180

<210> SEQ ID NO 7
<211> LENGTH: 220
<212> TYPE: PRT
<213> ORGANISM: Homo sapiens

<400> SEQUENCE: 7

Met Ala Gly Leu Ser Arg Gly Ser Ala Arg Ala Leu Leu Ala Ala Leu
1               5                   10                  15

Leu Ala Ser Thr Leu Leu Ala Leu Leu Val Ser Pro Ala Arg Gly Arg
            20                  25                  30

Gly Gly Arg Asp His Gly Asp Trp Asp Glu Ala Ser Arg Leu Pro Pro
        35                  40                  45

Leu Pro Pro Arg Glu Asp Ala Ala Arg Val Ala Arg Phe Val Thr His
```

```
            50                  55                  60
Val Ser Asp Trp Gly Ala Leu Ala Thr Ile Ser Thr Leu Glu Ala Val
 65                  70                  75                  80

Arg Gly Arg Pro Phe Ala Asp Val Leu Ser Leu Ser Asp Gly Pro Pro
                 85                  90                  95

Gly Ala Gly Ser Gly Val Pro Tyr Phe Tyr Leu Ser Pro Leu Gln Leu
                100                 105                 110

Ser Val Ser Asn Leu Gln Glu Asn Pro Tyr Ala Thr Leu Thr Met Thr
            115                 120                 125

Leu Ala Gln Thr Asn Phe Cys Lys Lys His Gly Phe Asp Pro Gln Ser
        130                 135                 140

Pro Leu Cys Val His Ile Met Leu Ser Gly Thr Val Thr Lys Val Asn
145                 150                 155                 160

Glu Thr Glu Met Asp Ile Ala Lys His Ser Leu Phe Ile Arg His Pro
                165                 170                 175

Glu Met Lys Thr Trp Pro Ser Ser His Asn Trp Phe Phe Ala Lys Leu
                180                 185                 190

Asn Ile Thr Asn Ile Trp Val Leu Asp Tyr Phe Gly Gly Pro Lys Ile
            195                 200                 205

Val Thr Pro Glu Glu Tyr Tyr Asn Val Thr Val Gln
        210                 215                 220

<210> SEQ ID NO 8
<211> LENGTH: 4
<212> TYPE: PRT
<213> ORGANISM: Homo sapiens

<400> SEQUENCE: 8

Asp Pro Gln Ser
1

<210> SEQ ID NO 9
<211> LENGTH: 185
<212> TYPE: PRT
<213> ORGANISM: Homo sapiens

<400> SEQUENCE: 9

Arg Gly Gly Arg Asp His Gly Asp Trp Asp Glu Ala Ser Arg Leu Pro
1               5                   10                  15

Pro Leu Pro Pro Arg Glu Asp Ala Ala Arg Val Ala Arg Phe Val Thr
                20                  25                  30

His Val Ser Asp Trp Gly Ala Leu Ala Thr Ile Ser Thr Leu Glu Ala
            35                  40                  45

Val Arg Gly Arg Pro Phe Ala Asp Val Leu Ser Leu Ser Asp Gly Pro
        50                  55                  60

Pro Gly Ala Gly Ser Gly Val Pro Tyr Phe Tyr Leu Ser Pro Leu Gln
 65                  70                  75                  80

Leu Ser Val Ser Asn Leu Gln Glu Asn Pro Tyr Ala Thr Leu Thr Met
                85                  90                  95

Thr Leu Ala Gln Thr Asn Phe Cys Lys Lys His Gly Phe Pro Leu Cys
                100                 105                 110

Val His Ile Met Leu Ser Gly Thr Val Thr Lys Val Asn Glu Thr Glu
            115                 120                 125

Met Asp Ile Ala Lys His Ser Leu Phe Ile Arg His Pro Glu Met Lys
        130                 135                 140

Thr Trp Pro Ser Ser His Asn Trp Phe Phe Ala Lys Leu Asn Ile Thr
```

-continued

```
145                 150                 155                 160
Asn Ile Trp Val Leu Asp Tyr Phe Gly Gly Pro Lys Ile Val Thr Pro
                165                 170                 175
Glu Glu Tyr Tyr Asn Val Thr Val Gln
            180                 185

<210> SEQ ID NO 10
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gly Gly Gly Gly Gly Ala Ala Ala Ala Gly Gly Gly Gly
1               5                   10

<210> SEQ ID NO 11
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Gly Ala Pro
1

<210> SEQ ID NO 12
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Gly Gly Gly Gly Pro
1               5

<210> SEQ ID NO 13
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Gly Ala Pro Gly Gly Gly Gly Gly Ala Ala Ala Ala Gly Gly Gly Gly
1               5                   10                  15

Gly Ala Pro Gly Gly Gly Gly Gly Ala Ala Ala Ala Gly Gly Gly Gly
            20                  25                  30

Gly Ala Pro
        35

<210> SEQ ID NO 14
<211> LENGTH: 57
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 14

Gly Ala Pro Gly Gly Gly Gly Ala Ala Ala Ala Gly Gly Gly
1               5                   10                  15

Gly Gly Gly Ala Pro Gly Gly Gly Gly Ala Ala Ala Ala Gly
            20                  25                  30

Gly Gly Gly Gly Gly Ala Pro Gly Gly Gly Gly Ala Ala Ala
        35                  40                  45

Ala Gly Gly Gly Gly Gly Gly Ala Pro
    50                  55

<210> SEQ ID NO 15
<211> LENGTH: 57
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Gly Ala Pro Gly Gly Gly Gly Ala Ala Ala Ala Gly Gly Gly
1               5                   10                  15

Gly Gly Gly Ala Pro Gly Gly Gly Gly Ala Ala Ala Ala Gly
            20                  25                  30

Gly Gly Gly Gly Gly Ala Pro Gly Gly Gly Gly Ala Ala Ala
        35                  40                  45

Ala Gly Gly Gly Gly Gly Gly Ala Pro
    50                  55

<210> SEQ ID NO 16
<211> LENGTH: 1256
<212> TYPE: PRT
<213> ORGANISM: Homo sapiens

<400> SEQUENCE: 16

Met Leu Phe Lys Leu Leu Gln Arg Gln Thr Tyr Thr Cys Leu Ser His
1               5                   10                  15

Arg Tyr Gly Leu Tyr Val Cys Phe Leu Gly Val Val Val Thr Ile Val
                20                  25                  30

Ser Ala Phe Gln Phe Gly Glu Val Val Leu Glu Trp Ser Arg Asp Gln
            35                  40                  45

Tyr His Val Leu Phe Asp Ser Tyr Arg Asp Asn Ile Ala Gly Lys Ser
        50                  55                  60

Phe Gln Asn Arg Leu Cys Leu Pro Met Pro Ile Asp Val Val Tyr Thr
65                  70                  75                  80

Trp Val Asn Gly Thr Asp Leu Glu Leu Leu Lys Glu Leu Gln Gln Val
                85                  90                  95

Arg Glu Gln Met Glu Glu Glu Gln Lys Ala Met Arg Glu Ile Leu Gly
                100                 105                 110

Lys Asn Thr Thr Glu Pro Thr Lys Lys Ser Glu Lys Gln Leu Glu Cys
            115                 120                 125

Leu Leu Thr His Cys Ile Lys Val Pro Met Leu Val Leu Asp Pro Ala
        130                 135                 140

Leu Pro Ala Asn Ile Thr Leu Lys Asp Leu Pro Ser Leu Tyr Pro Ser
```

-continued

```
                145                 150                 155                 160
            Phe His Ser Ala Ser Asp Ile Phe Asn Val Ala Lys Pro Lys Asn Pro
                            165                 170                 175
            Ser Thr Asn Val Ser Val Val Phe Asp Ser Thr Lys Asp Val Glu
                        180                 185                 190
            Asp Ala His Ser Gly Leu Leu Lys Gly Asn Ser Arg Gln Thr Val Trp
                        195                 200                 205
            Arg Gly Tyr Leu Thr Thr Asp Lys Glu Val Pro Gly Leu Val Leu Met
                210                 215                 220
            Gln Asp Leu Ala Phe Leu Ser Gly Phe Pro Thr Phe Lys Glu Thr
            225                 230                 235                 240
            Asn Gln Leu Lys Thr Lys Leu Pro Glu Asn Leu Ser Ser Lys Val Lys
                            245                 250                 255
            Leu Leu Gln Leu Tyr Ser Glu Ala Ser Val Ala Leu Leu Lys Leu Asn
                        260                 265                 270
            Asn Pro Lys Asp Phe Gln Glu Leu Asn Lys Gln Thr Lys Lys Asn Met
                        275                 280                 285
            Thr Ile Asp Gly Lys Glu Leu Thr Ile Ser Pro Ala Tyr Leu Leu Trp
                290                 295                 300
            Asp Leu Ser Ala Ile Ser Gln Ser Lys Gln Asp Glu Asp Ile Ser Ala
            305                 310                 315                 320
            Ser Arg Phe Glu Asp Asn Glu Glu Leu Arg Tyr Ser Leu Arg Ser Ile
                            325                 330                 335
            Glu Arg His Ala Pro Trp Val Arg Asn Ile Phe Ile Val Thr Asn Gly
                        340                 345                 350
            Gln Ile Pro Ser Trp Leu Asn Leu Asp Asn Pro Arg Val Thr Ile Val
                        355                 360                 365
            Thr His Gln Asp Val Phe Arg Asn Leu Ser His Leu Pro Thr Phe Ser
                370                 375                 380
            Ser Pro Ala Ile Glu Ser His Ile His Arg Ile Glu Gly Leu Ser Gln
            385                 390                 395                 400
            Lys Phe Ile Tyr Leu Asn Asp Asp Val Met Phe Gly Lys Asp Val Trp
                            405                 410                 415
            Pro Asp Asp Phe Tyr Ser His Ser Lys Gly Gln Lys Val Tyr Leu Thr
                        420                 425                 430
            Trp Pro Val Pro Asn Cys Ala Glu Gly Cys Pro Gly Ser Trp Ile Lys
                        435                 440                 445
            Asp Gly Tyr Cys Asp Lys Ala Cys Asn Asn Ser Ala Cys Asp Trp Asp
                450                 455                 460
            Gly Gly Asp Cys Ser Gly Asn Ser Gly Gly Ser Arg Tyr Ile Ala Gly
            465                 470                 475                 480
            Gly Gly Gly Thr Gly Ser Ile Gly Val Gly Gln Pro Trp Gln Phe Gly
                            485                 490                 495
            Gly Gly Ile Asn Ser Val Ser Tyr Cys Asn Gln Gly Cys Ala Asn Ser
                        500                 505                 510
            Trp Leu Ala Asp Lys Phe Cys Asp Gln Ala Cys Asn Val Leu Ser Cys
                        515                 520                 525
            Gly Phe Asp Ala Gly Asp Cys Gly Gln Asp His Phe His Glu Leu Tyr
                530                 535                 540
            Lys Val Ile Leu Leu Pro Asn Gln Thr His Tyr Ile Ile Pro Lys Gly
            545                 550                 555                 560
            Glu Cys Leu Pro Tyr Phe Ser Phe Ala Glu Val Ala Lys Arg Gly Val
                            565                 570                 575
```

-continued

Glu Gly Ala Tyr Ser Asp Asn Pro Ile Ile Arg His Ala Ser Ile Ala
            580                 585                 590

Asn Lys Trp Lys Thr Ile His Leu Ile Met His Ser Gly Met Asn Ala
            595                 600                 605

Thr Thr Ile His Phe Asn Leu Thr Phe Gln Asn Thr Asn Asp Glu Glu
            610                 615                 620

Phe Lys Met Gln Ile Thr Val Glu Val Asp Thr Arg Glu Gly Pro Lys
625                 630                 635                 640

Leu Asn Ser Thr Ala Gln Lys Gly Tyr Glu Asn Leu Val Ser Pro Ile
            645                 650                 655

Thr Leu Leu Pro Glu Ala Glu Ile Leu Phe Gly Asp Ile Pro Lys Glu
            660                 665                 670

Lys Arg Phe Pro Lys Phe Lys Arg His Asp Val Asn Ser Thr Arg Arg
            675                 680                 685

Ala Gln Glu Glu Val Lys Ile Pro Leu Val Asn Ile Ser Leu Leu Pro
            690                 695                 700

Lys Asp Ala Gln Leu Ser Leu Asn Thr Leu Asp Leu Gln Leu Glu His
705                 710                 715                 720

Gly Asp Ile Thr Leu Lys Gly Tyr Asn Leu Ser Lys Ser Ala Leu Leu
            725                 730                 735

Arg Ser Phe Leu Met Asn Ser Gln His Ala Lys Ile Lys Asn Gln Ala
            740                 745                 750

Ile Ile Thr Asp Glu Thr Asn Asp Ser Leu Val Ala Pro Gln Glu Lys
            755                 760                 765

Gln Val His Lys Ser Ile Leu Pro Asn Ser Leu Gly Val Ser Glu Arg
            770                 775                 780

Leu Gln Arg Leu Thr Phe Pro Ala Val Ser Val Lys Val Asn Gly His
785                 790                 795                 800

Asp Gln Gly Gln Asn Pro Pro Leu Asp Leu Glu Thr Thr Ala Arg Phe
            805                 810                 815

Arg Val Glu Thr His Thr Gln Lys Thr Ile Gly Gly Asn Val Thr Lys
            820                 825                 830

Glu Lys Pro Pro Ser Leu Ile Val Pro Leu Glu Ser Gln Met Thr Lys
            835                 840                 845

Glu Lys Lys Ile Thr Gly Lys Glu Lys Glu Asn Ser Arg Met Glu Glu
            850                 855                 860

Asn Ala Glu Asn His Ile Gly Val Thr Glu Val Leu Leu Gly Arg Lys
865                 870                 875                 880

Leu Gln His Tyr Thr Asp Ser Tyr Leu Gly Phe Leu Pro Trp Glu Lys
            885                 890                 895

Lys Lys Tyr Phe Gln Asp Leu Leu Asp Glu Glu Glu Ser Leu Lys Thr
            900                 905                 910

Gln Leu Ala Tyr Phe Thr Asp Ser Lys Asn Thr Gly Arg Gln Leu Lys
            915                 920                 925

Asp Thr Phe Ala Asp Ser Leu Arg Tyr Val Asn Lys Ile Leu Asn Ser
            930                 935                 940

Lys Phe Gly Phe Thr Ser Arg Lys Val Pro Ala His Met Pro His Met
945                 950                 955                 960

Ile Asp Arg Ile Val Met Gln Glu Leu Gln Asp Met Phe Pro Glu Glu
            965                 970                 975

Phe Asp Lys Thr Ser His Lys Val Arg His Ser Glu Asp Met Gln
            980                 985                 990

```
Phe Ala Phe Ser Tyr Phe Tyr Tyr Leu Met Ser Ala Val Gln Pro Leu
        995                 1000                1005

Asn Ile Ser Gln Val Phe Asp Glu Val Asp Thr Asp Gln Ser Gly
   1010                1015                1020

Val Leu Ser Asp Arg Glu Ile Arg Thr Leu Ala Thr Arg Ile His
   1025                1030                1035

Glu Leu Pro Leu Ser Leu Gln Asp Leu Thr Gly Leu Glu His Met
   1040                1045                1050

Leu Ile Asn Cys Ser Lys Met Leu Pro Ala Asp Ile Thr Gln Leu
   1055                1060                1065

Asn Asn Ile Pro Pro Thr Gln Glu Ser Tyr Tyr Asp Pro Asn Leu
   1070                1075                1080

Pro Pro Val Thr Lys Ser Leu Val Thr Asn Cys Lys Pro Val Thr
   1085                1090                1095

Asp Lys Ile His Lys Ala Tyr Lys Asp Lys Asn Lys Tyr Arg Phe
   1100                1105                1110

Glu Ile Met Gly Glu Glu Ile Ala Phe Lys Met Ile Arg Thr
   1115                1120                1125

Asn Val Ser His Val Val Gly Gln Leu Asp Asp Ile Arg Lys Asn
   1130                1135                1140

Pro Arg Lys Phe Val Cys Leu Asn Asp Asn Ile Asp His Asn His
   1145                1150                1155

Lys Asp Ala Gln Thr Val Lys Ala Val Leu Arg Asp Phe Tyr Glu
   1160                1165                1170

Ser Met Phe Pro Ile Pro Ser Gln Phe Glu Leu Pro Arg Glu Tyr
   1175                1180                1185

Arg Asn Arg Phe Leu His Met His Glu Leu Gln Glu Trp Arg Ala
   1190                1195                1200

Tyr Arg Asp Lys Leu Lys Phe Trp Thr His Cys Val Leu Ala Thr
   1205                1210                1215

Leu Ile Met Phe Thr Ile Phe Ser Phe Phe Ala Glu Gln Leu Ile
   1220                1225                1230

Ala Leu Lys Arg Lys Ile Phe Pro Arg Arg Arg Ile His Lys Glu
   1235                1240                1245

Ala Ser Pro Asn Arg Ile Arg Val
   1250                1255

<210> SEQ ID NO 17
<211> LENGTH: 305
<212> TYPE: PRT
<213> ORGANISM: Homo sapiens

<400> SEQUENCE: 17

Met Ala Ala Gly Leu Ala Arg Leu Leu Leu Leu Gly Leu Ser Ala
 1               5                  10                  15

Gly Gly Pro Ala Pro Ala Gly Ala Ala Lys Met Lys Val Val Glu Glu
                 20                  25                  30

Pro Asn Ala Phe Gly Val Asn Asn Pro Phe Leu Pro Gln Ala Ser Arg
       35                  40                  45

Leu Gln Ala Lys Arg Asp Pro Ser Pro Val Ser Gly Pro Val His Leu
   50                  55                  60

Phe Arg Leu Ser Gly Lys Cys Phe Ser Leu Val Glu Ser Thr Tyr Lys
65                  70                  75                  80

Tyr Glu Phe Cys Pro Phe His Asn Val Thr Gln His Glu Gln Thr Phe
                85                  90                  95
```

```
Arg Trp Asn Ala Tyr Ser Gly Ile Leu Gly Ile Trp His Glu Trp Glu
            100                 105                 110

Ile Ala Asn Asn Thr Phe Thr Gly Met Trp Met Arg Asp Gly Asp Ala
        115                 120                 125

Cys Arg Ser Arg Ser Arg Gln Ser Lys Val Glu Leu Ala Cys Gly Lys
    130                 135                 140

Ser Asn Arg Leu Ala His Val Ser Glu Pro Ser Thr Cys Val Tyr Ala
145                 150                 155                 160

Leu Thr Phe Glu Thr Pro Leu Val Cys His Pro His Ala Leu Leu Val
                165                 170                 175

Tyr Pro Thr Leu Pro Glu Ala Leu Gln Arg Gln Trp Asp Gln Val Glu
            180                 185                 190

Gln Asp Leu Ala Asp Glu Leu Ile Thr Pro Gln Gly His Glu Lys Leu
        195                 200                 205

Leu Arg Thr Leu Phe Glu Asp Ala Gly Tyr Leu Lys Thr Pro Glu Glu
    210                 215                 220

Asn Glu Pro Thr Gln Leu Glu Gly Gly Pro Asp Ser Leu Gly Phe Glu
225                 230                 235                 240

Thr Leu Glu Asn Cys Arg Lys Ala His Lys Glu Leu Ser Lys Glu Ile
                245                 250                 255

Lys Arg Leu Lys Gly Leu Leu Thr Gln His Gly Ile Pro Tyr Thr Arg
            260                 265                 270

Pro Thr Glu Thr Ser Asn Leu Glu His Leu Gly His Glu Thr Pro Arg
        275                 280                 285

Ala Lys Ser Pro Glu Gln Leu Arg Gly Asp Pro Gly Leu Arg Gly Ser
    290                 295                 300

Leu
305

<210> SEQ ID NO 18
<211> LENGTH: 920
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Met Glu Ala Val Ala Val Ala Ala Val Gly Val Leu Leu Leu Ala
1               5                   10                  15

Gly Ala Gly Gly Ala Ala Gly Asp Glu Ala Arg Glu Ala Ala Val
            20                  25                  30

Arg Ala Leu Val Ala Arg Leu Leu Gly Pro Gly Pro Ala Ala Asp Phe
        35                  40                  45

Ser Val Ser Val Glu Arg Ala Leu Ala Ala Lys Pro Gly Leu Asp Thr
    50                  55                  60

Tyr Ser Leu Gly Gly Gly Gly Ala Ala Arg Val Arg Val Arg Gly Ser
65                  70                  75                  80

Thr Gly Val Ala Ala Ala Ala Gly Leu His Arg Tyr Leu Arg Asp Phe
                85                  90                  95

Cys Gly Cys His Val Ala Trp Ser Gly Ser Gln Leu Arg Leu Pro Arg
            100                 105                 110

Pro Leu Pro Ala Val Pro Gly Glu Leu Thr Glu Ala Thr Pro Asn Arg
        115                 120                 125
```

-continued

Tyr Arg Tyr Tyr Gln Asn Val Cys Thr Gln Ser Tyr Ser Phe Val Trp
        130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
                165                 170                 175

Arg Val Tyr Leu Ala Leu Gly Leu Thr Gln Ala Glu Ile Asn Glu Phe
            180                 185                 190

Phe Thr Gly Pro Ala Phe Leu Ala Trp Gly Arg Met Gly Asn Leu His
        195                 200                 205

Thr Trp Asp Gly Pro Leu Pro Pro Ser Trp His Ile Lys Gln Leu Tyr
210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
            260                 265                 270

Cys Ser Tyr Ser Cys Ser Phe Leu Leu Ala Pro Glu Asp Pro Ile Phe
        275                 280                 285

Pro Ile Ile Gly Ser Leu Phe Leu Arg Glu Leu Ile Lys Glu Phe Gly
290                 295                 300

Thr Asp His Ile Tyr Gly Ala Asp Thr Phe Asn Glu Met Gln Pro Pro
305                 310                 315                 320

Ser Ser Glu Pro Ser Tyr Leu Ala Ala Thr Thr Ala Val Tyr Glu
                325                 330                 335

Ala Met Thr Ala Val Asp Thr Glu Ala Val Trp Leu Leu Gln Gly Trp
            340                 345                 350

Leu Phe Gln His Gln Pro Gln Phe Trp Gly Pro Ala Gln Ile Arg Ala
        355                 360                 365

Val Leu Gly Ala Val Pro Arg Gly Arg Leu Leu Val Leu Asp Leu Phe
370                 375                 380

Ala Glu Ser Gln Pro Val Tyr Thr Arg Thr Ala Ser Phe Gln Gly Gln
385                 390                 395                 400

Pro Phe Ile Trp Cys Met Leu His Asn Phe Gly Gly Asn His Gly Leu
                405                 410                 415

Phe Gly Ala Leu Glu Ala Val Asn Gly Gly Pro Glu Ala Ala Arg Leu
            420                 425                 430

Phe Pro Asn Ser Thr Met Val Gly Thr Gly Met Ala Pro Glu Gly Ile
        435                 440                 445

Ser Gln Asn Glu Val Val Tyr Ser Leu Met Ala Glu Leu Gly Trp Arg
450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
        515                 520                 525

Ile Trp Tyr Asn Arg Ser Asp Val Phe Glu Ala Trp Arg Leu Leu Leu
530                 535                 540

Thr Ser Ala Pro Ser Leu Ala Thr Ser Pro Ala Phe Arg Tyr Asp Leu

```
            545                 550                 555                 560
Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Pro Ala Leu Asp Glu
        595                 600                 605

Val Leu Ala Ser Asp Ser Arg Phe Leu Leu Gly Ser Trp Leu Glu Gln
610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
        675                 680                 685

Gly Ile Pro Phe Gln Gln His Gln Phe Asp Lys Asn Val Phe Gln Leu
    690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp Gly Ala Pro Gly Gly Gly Gly Gly Ala
            740                 745                 750

Ala Ala Ala Ala Gly Gly Gly Gly Ala Pro Gly Gly Gly Gly
        755                 760                 765

Gly Ala Ala Ala Ala Gly Gly Gly Gly Ala Pro Gly Gly
    770                 775                 780

Gly Gly Gly Ala Ala Ala Ala Gly Gly Gly Gly Gly Ala Pro
785                 790                 795                 800

Asp Gly Gly Phe Cys Glu Val Cys Lys Lys Leu Val Gly Tyr Leu Asp
                805                 810                 815

Arg Asn Leu Glu Lys Asn Ser Thr Lys Gln Glu Ile Leu Ala Ala Leu
            820                 825                 830

Glu Lys Gly Cys Ser Phe Leu Pro Asp Pro Tyr Gln Lys Gln Cys Asp
        835                 840                 845

Gln Phe Val Ala Glu Tyr Glu Pro Val Leu Ile Glu Ile Leu Val Glu
    850                 855                 860

Val Met Asp Pro Ser Phe Val Cys Leu Lys Ile Gly Ala Cys Pro Ser
865                 870                 875                 880

Ala His Lys Pro Leu Leu Gly Thr Glu Lys Cys Ile Trp Gly Pro Ser
                885                 890                 895

Tyr Trp Cys Gln Asn Thr Glu Thr Ala Ala Gln Cys Asn Ala Val Glu
            900                 905                 910

His Cys Lys Arg His Val Trp Asn
        915                 920

<210> SEQ ID NO 19
<211> LENGTH: 980
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 19

```
Met Glu Ala Val Ala Val Ala Ala Val Gly Val Leu Leu Leu Ala
1               5                  10                  15

Gly Ala Gly Gly Ala Ala Gly Asp Glu Ala Arg Glu Ala Ala Val
                20                  25                  30

Arg Ala Leu Val Ala Arg Leu Leu Gly Pro Gly Pro Ala Ala Asp Phe
                35                  40                  45

Ser Val Ser Val Glu Arg Ala Leu Ala Ala Lys Pro Gly Leu Asp Thr
                50                  55                  60

Tyr Ser Leu Gly Gly Gly Ala Ala Arg Val Arg Val Arg Gly Ser
65                  70                  75                  80

Thr Gly Val Ala Ala Ala Gly Leu His Arg Tyr Leu Arg Asp Phe
                    85                  90                  95

Cys Gly Cys His Val Ala Trp Ser Gly Ser Gln Leu Arg Leu Pro Arg
                    100                 105                 110

Pro Leu Pro Ala Val Pro Gly Glu Leu Thr Glu Ala Thr Pro Asn Arg
                    115                 120                 125

Tyr Arg Tyr Tyr Gln Asn Val Cys Thr Gln Ser Tyr Ser Phe Val Trp
                    130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
                    165                 170                 175

Arg Val Tyr Leu Ala Leu Gly Leu Thr Gln Ala Glu Ile Asn Glu Phe
                    180                 185                 190

Phe Thr Gly Pro Ala Phe Leu Ala Trp Gly Arg Met Gly Asn Leu His
                    195                 200                 205

Thr Trp Asp Gly Pro Leu Pro Pro Ser Trp His Ile Lys Gln Leu Tyr
                    210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                    245                 250                 255

Phe Pro Gln Val Asn Val Thr Lys Met Gly Ser Trp Gly His Phe Asn
                    260                 265                 270

Cys Ser Tyr Ser Cys Ser Phe Leu Leu Ala Pro Glu Asp Pro Ile Phe
                    275                 280                 285

Pro Ile Ile Gly Ser Leu Phe Leu Arg Glu Leu Ile Lys Glu Phe Gly
                    290                 295                 300

Thr Asp His Ile Tyr Gly Ala Asp Thr Phe Asn Glu Met Gln Pro Pro
305                 310                 315                 320

Ser Ser Glu Pro Ser Tyr Leu Ala Ala Thr Thr Ala Val Tyr Glu
                    325                 330                 335

Ala Met Thr Ala Val Asp Thr Glu Ala Val Trp Leu Leu Gln Gly Trp
                    340                 345                 350

Leu Phe Gln His Gln Pro Gln Phe Trp Gly Pro Ala Gln Ile Arg Ala
                    355                 360                 365

Val Leu Gly Ala Val Pro Arg Gly Arg Leu Leu Val Leu Asp Leu Phe
                    370                 375                 380

Ala Glu Ser Gln Pro Val Tyr Thr Arg Thr Ala Ser Phe Gln Gly Gln
385                 390                 395                 400
```

```
Pro Phe Ile Trp Cys Met Leu His Asn Phe Gly Gly Asn His Gly Leu
                405                 410                 415

Phe Gly Ala Leu Glu Ala Val Asn Gly Gly Pro Glu Ala Ala Arg Leu
            420                 425                 430

Phe Pro Asn Ser Thr Met Val Gly Thr Gly Met Ala Pro Glu Gly Ile
            435                 440                 445

Ser Gln Asn Glu Val Val Tyr Ser Leu Met Ala Glu Leu Gly Trp Arg
        450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
            500                 505                 510

Asn Arg Ser Pro Leu Val Arg Pro Ser Leu Gln Met Asn Thr Ser
            515                 520                 525

Ile Trp Tyr Asn Arg Ser Asp Val Phe Glu Ala Trp Arg Leu Leu Leu
        530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
        595                 600                 605

Val Leu Ala Ser Asp Ser Arg Phe Leu Leu Gly Ser Trp Leu Glu Gln
610                 615                 620

Ala Arg Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
        675                 680                 685

Gly Ile Pro Phe Gln Gln His Gln Phe Asp Lys Asn Val Phe Gln Leu
        690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp Gly Ala Pro Gly Gly Gly Gly Gly Ala
            740                 745                 750

Ala Ala Ala Ala Gly Gly Gly Gly Gly Ala Pro Gly Gly Gly
        755                 760                 765

Gly Ala Ala Ala Ala Gly Gly Gly Gly Gly Ala Pro Gly Gly
        770                 775                 780

Gly Gly Gly Ala Ala Ala Ala Gly Gly Gly Gly Gly Ala Pro
785                 790                 795                 800

Ser Pro Leu Pro Ile Thr Pro Val Asn Ala Thr Cys Ala Ile Arg His
                805                 810                 815

Pro Cys His Asn Asn Leu Met Asn Ala Ile Arg Ala Gln Leu Ala Ala
```

```
                    820                 825                 830
Leu Asn Gly Ser Ala Asn Ala Leu Phe Ile Leu Tyr Tyr Thr Ala Gln
            835                 840                 845
Gly Glu Pro Phe Pro Asn Asn Leu Asp Lys Leu Cys Gly Pro Asn Val
            850                 855                 860
Thr Asp Phe Pro Pro Phe His Ala Asn Gly Thr Glu Lys Ala Lys Leu
865                 870                 875                 880
Val Glu Leu Tyr Arg Ile Val Val Tyr Leu Gly Thr Ser Leu Gly Asn
            885                 890                 895
Ile Thr Arg Asp Gln Lys Ile Leu Asn Pro Ser Ala Leu Ser Leu His
            900                 905                 910
Ser Lys Leu Asn Ala Thr Ala Asp Ile Leu Arg Gly Leu Leu Ser Asn
            915                 920                 925
Val Leu Cys Arg Leu Cys Ser Lys Tyr His Val Gly His Val Asp Val
            930                 935                 940
Thr Tyr Gly Pro Asp Thr Ser Gly Lys Asp Val Ala Gln Lys Ala Lys
945                 950                 955                 960
Leu Gly Cys Gln Leu Leu Gly Lys Tyr Lys Gln Ile Ile Ala Val Leu
            965                 970                 975
Ala Gln Ala Phe
            980

<210> SEQ ID NO 20
<211> LENGTH: 985
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Met Glu Ala Val Ala Val Ala Ala Val Gly Val Leu Leu Leu Ala
1               5                  10                  15
Gly Ala Gly Gly Ala Ala Gly Asp Glu Ala Arg Glu Ala Ala Ala Val
            20                  25                  30
Arg Ala Leu Val Ala Arg Leu Leu Gly Pro Gly Pro Ala Ala Asp Phe
            35                  40                  45
Ser Val Ser Val Glu Arg Ala Leu Ala Ala Lys Pro Gly Leu Asp Thr
    50                  55                  60
Tyr Ser Leu Gly Gly Gly Gly Ala Ala Arg Val Arg Val Arg Gly Ser
65                  70                  75                  80
Thr Gly Val Ala Ala Ala Ala Gly Leu His Arg Tyr Leu Arg Asp Phe
                85                  90                  95
Cys Gly Cys His Val Ala Trp Ser Gly Ser Gln Leu Arg Leu Pro Arg
            100                 105                 110
Pro Leu Pro Ala Val Pro Gly Glu Leu Thr Glu Ala Thr Pro Asn Arg
            115                 120                 125
Tyr Arg Tyr Tyr Gln Asn Val Cys Thr Gln Ser Tyr Ser Phe Val Trp
            130                 135                 140
Trp Asp Trp Ala Arg Trp Glu Arg Glu Ile Asp Trp Met Ala Leu Asn
145                 150                 155                 160
Gly Ile Asn Leu Ala Leu Ala Trp Ser Gly Gln Glu Ala Ile Trp Gln
                165                 170                 175
Arg Val Tyr Leu Ala Leu Gly Leu Thr Gln Ala Glu Ile Asn Glu Phe
            180                 185                 190
```

```
Phe Thr Gly Pro Ala Phe Leu Ala Trp Gly Arg Met Gly Asn Leu His
    195                 200                 205

Thr Trp Asp Gly Pro Leu Pro Pro Ser Trp His Ile Lys Gln Leu Tyr
    210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
                260                 265                 270

Cys Ser Tyr Ser Cys Ser Phe Leu Leu Ala Pro Glu Asp Pro Ile Phe
            275                 280                 285

Pro Ile Ile Gly Ser Leu Phe Leu Arg Glu Leu Ile Lys Glu Phe Gly
            290                 295                 300

Thr Asp His Ile Tyr Gly Ala Asp Thr Phe Asn Glu Met Gln Pro Pro
305                 310                 315                 320

Ser Ser Glu Pro Ser Tyr Leu Ala Ala Thr Thr Ala Val Tyr Glu
                325                 330                 335

Ala Met Thr Ala Val Asp Thr Glu Ala Val Trp Leu Leu Gln Gly Trp
            340                 345                 350

Leu Phe Gln His Gln Pro Gln Phe Trp Gly Pro Ala Gln Ile Arg Ala
            355                 360                 365

Val Leu Gly Ala Val Pro Arg Gly Arg Leu Leu Val Leu Asp Leu Phe
            370                 375                 380

Ala Glu Ser Gln Pro Val Tyr Thr Arg Thr Ala Ser Phe Gln Gly Gln
385                 390                 395                 400

Pro Phe Ile Trp Cys Met Leu His Asn Phe Gly Gly Asn His Gly Leu
                405                 410                 415

Phe Gly Ala Leu Glu Ala Val Asn Gly Gly Pro Glu Ala Ala Arg Leu
            420                 425                 430

Phe Pro Asn Ser Thr Met Val Gly Thr Gly Met Ala Pro Glu Gly Ile
            435                 440                 445

Ser Gln Asn Glu Val Val Tyr Ser Leu Met Ala Glu Leu Gly Trp Arg
            450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
            515                 520                 525

Ile Trp Tyr Asn Arg Ser Asp Val Phe Glu Ala Trp Arg Leu Leu Leu
            530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
            595                 600                 605
```

```
Val Leu Ala Ser Asp Ser Arg Phe Leu Leu Gly Ser Trp Leu Glu Gln
610                 615                 620
Ala Arg Ala Ala Ala Val Ser Glu Ala Glu Ala Asp Phe Tyr Glu Gln
625                 630                 635                 640
Asn Ser Arg Tyr Gln Leu Thr Leu Trp Gly Pro Glu Gly Asn Ile Leu
            645                 650                 655
Asp Tyr Ala Asn Lys Gln Leu Ala Gly Leu Val Ala Asn Tyr Tyr Thr
            660                 665                 670
Pro Arg Trp Arg Leu Phe Leu Glu Ala Leu Val Asp Ser Val Ala Gln
        675                 680                 685
Gly Ile Pro Phe Gln Gln His Gln Phe Asp Lys Asn Val Phe Gln Leu
690                 695                 700
Glu Gln Ala Phe Val Leu Ser Lys Gln Arg Tyr Pro Ser Gln Pro Arg
705                 710                 715                 720
Gly Asp Thr Val Asp Leu Ala Lys Lys Ile Phe Leu Lys Tyr Tyr Pro
            725                 730                 735
Arg Trp Val Ala Gly Ser Trp Gly Ala Pro Gly Gly Gly Gly Gly Ala
            740                 745                 750
Ala Ala Ala Ala Gly Gly Gly Gly Gly Ala Pro Gly Gly Gly Gly
        755                 760                 765
Gly Ala Ala Ala Ala Gly Gly Gly Gly Gly Ala Pro Gly Gly
770                 775                 780
Gly Gly Gly Ala Ala Ala Ala Gly Gly Gly Gly Gly Ala Pro
785                 790                 795                 800
Arg Gly Gly Arg Asp His Gly Asp Trp Asp Glu Ala Ser Arg Leu Pro
            805                 810                 815
Pro Leu Pro Pro Arg Glu Asp Ala Ala Arg Val Ala Arg Phe Val Thr
        820                 825                 830
His Val Ser Asp Trp Gly Ala Leu Ala Thr Ile Ser Thr Leu Glu Ala
            835                 840                 845
Val Arg Gly Arg Pro Phe Ala Asp Val Leu Ser Leu Ser Asp Gly Pro
        850                 855                 860
Pro Gly Ala Gly Ser Gly Val Pro Tyr Phe Tyr Leu Ser Pro Leu Gln
865                 870                 875                 880
Leu Ser Val Ser Asn Leu Gln Glu Asn Pro Tyr Ala Thr Leu Thr Met
            885                 890                 895
Thr Leu Ala Gln Thr Asn Phe Cys Lys Lys His Gly Phe Pro Leu Cys
            900                 905                 910
Val His Ile Met Leu Ser Gly Thr Val Thr Lys Val Asn Glu Thr Glu
        915                 920                 925
Met Asp Ile Ala Lys His Ser Leu Phe Ile Arg His Pro Glu Met Lys
930                 935                 940
Thr Trp Pro Ser Ser His Asn Trp Phe Phe Ala Lys Leu Asn Ile Thr
945                 950                 955                 960
Asn Ile Trp Val Leu Asp Tyr Phe Gly Gly Pro Lys Ile Val Thr Pro
            965                 970                 975
Glu Glu Tyr Tyr Asn Val Thr Val Gln
            980                 985

<210> SEQ ID NO 21
<211> LENGTH: 860
<212> TYPE: PRT
<213> ORGANISM: Artificial Sequence
<220> FEATURE:
<221> NAME/KEY: source
```

<223> OTHER INFORMATION: /note="Description of Artificial Sequence: Synthetic polypeptide"

<400> SEQUENCE: 21

```
Met Glu Ala Val Ala Val Ala Ala Val Gly Val Leu Leu Leu Ala
1               5                   10                  15

Gly Ala Gly Gly Ala Ala Gly Asp Glu Ala Arg Glu Ala Ala Val
                20                  25                  30

Arg Ala Leu Val Ala Arg Leu Leu Gly Pro Gly Pro Ala Ala Asp Phe
                35                  40                  45

Ser Val Ser Val Glu Arg Ala Leu Ala Ala Lys Pro Gly Leu Asp Thr
50                  55                  60

Tyr Ser Leu Gly Gly Gly Ala Ala Arg Val Arg Val Arg Gly Ser
65                  70                  75                  80

Thr Gly Val Ala Ala Ala Gly Leu His Arg Tyr Leu Arg Asp Phe
                85                  90                  95

Cys Gly Cys His Val Ala Trp Ser Gly Ser Gln Leu Arg Leu Pro Arg
                100                 105                 110

Pro Leu Pro Ala Val Pro Gly Glu Leu Thr Glu Ala Thr Pro Asn Arg
                115                 120                 125

Tyr Arg Tyr Tyr Gln Asn Val Cys Thr Gln Ser Tyr Ser Phe Val Trp
                130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
                165                 170                 175

Arg Val Tyr Leu Ala Leu Gly Leu Thr Gln Ala Glu Ile Asn Glu Phe
                180                 185                 190

Phe Thr Gly Pro Ala Phe Leu Ala Trp Gly Arg Met Gly Asn Leu His
                195                 200                 205

Thr Trp Asp Gly Pro Leu Pro Pro Ser Trp His Ile Lys Gln Leu Tyr
210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
                260                 265                 270

Cys Ser Tyr Ser Cys Ser Phe Leu Leu Ala Pro Glu Asp Pro Ile Phe
                275                 280                 285

Pro Ile Ile Gly Ser Leu Phe Leu Arg Glu Leu Ile Lys Glu Phe Gly
                290                 295                 300

Thr Asp His Ile Tyr Gly Ala Asp Thr Phe Asn Glu Met Gln Pro Pro
305                 310                 315                 320

Ser Ser Glu Pro Ser Tyr Leu Ala Ala Ala Thr Thr Ala Val Tyr Glu
                325                 330                 335

Ala Met Thr Ala Val Asp Thr Glu Ala Val Trp Leu Leu Gln Gly Trp
                340                 345                 350

Leu Phe Gln His Gln Pro Gln Phe Trp Gly Pro Ala Gln Ile Arg Ala
                355                 360                 365

Val Leu Gly Ala Val Pro Arg Gly Arg Leu Leu Val Leu Asp Leu Phe
                370                 375                 380

Ala Glu Ser Gln Pro Val Tyr Thr Arg Thr Ala Ser Phe Gln Gly Gln
385                 390                 395                 400
```

```
Pro Phe Ile Trp Cys Met Leu His Asn Phe Gly Gly Asn His Gly Leu
            405                 410                 415

Phe Gly Ala Leu Glu Ala Val Asn Gly Gly Pro Glu Ala Ala Arg Leu
        420                 425                 430

Phe Pro Asn Ser Thr Met Val Gly Thr Gly Met Ala Pro Glu Gly Ile
        435                 440                 445

Ser Gln Asn Glu Val Val Tyr Ser Leu Met Ala Glu Leu Gly Trp Arg
    450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
        515                 520                 525

Ile Trp Tyr Asn Arg Ser Asp Val Phe Glu Ala Trp Arg Leu Leu Leu
    530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
        595                 600                 605

Val Leu Ala Ser Asp Ser Arg Phe Leu Leu Gly Ser Trp Leu Glu Gln
    610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
        675                 680                 685

Gly Ile Pro Phe Gln Gln His Gln Phe Asp Lys Asn Val Phe Gln Leu
    690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp Gly Ala Pro Gly Gly Gly Gly Gly Ala
            740                 745                 750

Ala Ala Ala Ala Gly Gly Gly Gly Ala Pro Gly Gly Gly Gly
        755                 760                 765

Gly Ala Ala Ala Ala Gly Gly Gly Gly Ala Pro Gly Gly
        770                 775                 780

Gly Gly Gly Ala Ala Ala Ala Gly Gly Gly Gly Gly Ala Pro
785                 790                 795                 800

Leu Cys Gly Gly Glu Leu Val Asp Thr Leu Gln Phe Val Cys Gly Asp
                805                 810                 815
```

```
Arg Gly Phe Tyr Phe Ser Arg Pro Ala Ser Arg Val Ser Arg Arg Ser
            820                 825                 830

Arg Gly Ile Val Glu Glu Cys Cys Phe Arg Ser Cys Asp Leu Ala Leu
        835                 840                 845

Leu Glu Thr Tyr Cys Ala Thr Pro Ala Lys Ser Glu
    850                 855                 860

<210> SEQ ID NO 22
<211> LENGTH: 60
<212> TYPE: PRT
<213> ORGANISM: Homo sapiens

<400> SEQUENCE: 22

Leu Cys Gly Gly Glu Leu Val Asp Thr Leu Gln Phe Val Cys Gly Asp
1               5                   10                  15

Arg Gly Phe Tyr Phe Ser Arg Pro Ala Ser Arg Val Ser Arg Arg Ser
            20                  25                  30

Arg Gly Ile Val Glu Glu Cys Cys Phe Arg Ser Cys Asp Leu Ala Leu
        35                  40                  45

Leu Glu Thr Tyr Cys Ala Thr Pro Ala Lys Ser Glu
    50                  55                  60

<210> SEQ ID NO 23
<211> LENGTH: 897
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Asp Glu Ala Arg Glu Ala Ala Val Arg Ala Leu Val Ala Arg Leu
1               5                   10                  15

Leu Gly Pro Gly Pro Ala Ala Asp Phe Ser Val Ser Val Glu Arg Ala
            20                  25                  30

Leu Ala Ala Lys Pro Gly Leu Asp Thr Tyr Ser Leu Gly Gly Gly Gly
        35                  40                  45

Ala Ala Arg Val Arg Val Arg Gly Ser Thr Gly Val Ala Ala Ala Ala
    50                  55                  60

Gly Leu His Arg Tyr Leu Arg Asp Phe Cys Gly Cys His Val Ala Trp
65                  70                  75                  80

Ser Gly Ser Gln Leu Arg Leu Pro Arg Pro Leu Pro Ala Val Pro Gly
            85                  90                  95

Glu Leu Thr Glu Ala Thr Pro Asn Arg Tyr Arg Tyr Gln Asn Val
            100                 105                 110

Cys Thr Gln Ser Tyr Ser Phe Val Trp Trp Asp Trp Ala Arg Trp Glu
        115                 120                 125

Arg Glu Ile Asp Trp Met Ala Leu Asn Gly Ile Asn Leu Ala Leu Ala
    130                 135                 140

Trp Ser Gly Gln Glu Ala Ile Trp Gln Arg Val Tyr Leu Ala Leu Gly
145                 150                 155                 160

Leu Thr Gln Ala Glu Ile Asn Glu Phe Phe Thr Gly Pro Ala Phe Leu
            165                 170                 175

Ala Trp Gly Arg Met Gly Asn Leu His Thr Trp Asp Gly Pro Leu Pro
        180                 185                 190

Pro Ser Trp His Ile Lys Gln Leu Tyr Leu Gln His Arg Val Leu Asp
    195                 200                 205
```

-continued

```
Gln Met Arg Ser Phe Gly Met Thr Pro Val Leu Pro Ala Phe Ala Gly
    210                 215                 220

His Val Pro Glu Ala Val Thr Arg Val Phe Pro Gln Val Asn Val Thr
225                 230                 235                 240

Lys Met Gly Ser Trp Gly His Phe Asn Cys Ser Tyr Ser Cys Ser Phe
                245                 250                 255

Leu Leu Ala Pro Glu Asp Pro Ile Phe Pro Ile Ile Gly Ser Leu Phe
            260                 265                 270

Leu Arg Glu Leu Ile Lys Glu Phe Gly Thr Asp His Ile Tyr Gly Ala
        275                 280                 285

Asp Thr Phe Asn Glu Met Gln Pro Pro Ser Ser Glu Pro Ser Tyr Leu
    290                 295                 300

Ala Ala Ala Thr Thr Ala Val Tyr Glu Ala Met Thr Ala Val Asp Thr
305                 310                 315                 320

Glu Ala Val Trp Leu Leu Gln Gly Trp Leu Phe Gln His Gln Pro Gln
                325                 330                 335

Phe Trp Gly Pro Ala Gln Ile Arg Ala Val Leu Gly Ala Val Pro Arg
            340                 345                 350

Gly Arg Leu Leu Val Leu Asp Leu Phe Ala Glu Ser Gln Pro Val Tyr
        355                 360                 365

Thr Arg Thr Ala Ser Phe Gln Gly Gln Pro Phe Ile Trp Cys Met Leu
    370                 375                 380

His Asn Phe Gly Gly Asn His Gly Leu Phe Gly Ala Leu Glu Ala Val
385                 390                 395                 400

Asn Gly Gly Pro Glu Ala Ala Arg Leu Phe Pro Asn Ser Thr Met Val
                405                 410                 415

Gly Thr Gly Met Ala Pro Glu Gly Ile Ser Gln Asn Glu Val Val Tyr
            420                 425                 430

Ser Leu Met Ala Glu Leu Gly Trp Arg Lys Asp Pro Val Pro Asp Leu
        435                 440                 445

Ala Ala Trp Val Thr Ser Phe Ala Ala Arg Arg Tyr Gly Val Ser His
    450                 455                 460

Pro Asp Ala Gly Ala Ala Trp Arg Leu Leu Arg Ser Val Tyr Asn
465                 470                 475                 480

Cys Ser Gly Glu Ala Cys Arg Gly His Asn Arg Ser Pro Leu Val Arg
                485                 490                 495

Arg Pro Ser Leu Gln Met Asn Thr Ser Ile Trp Tyr Asn Arg Ser Asp
            500                 505                 510

Val Phe Glu Ala Trp Arg Leu Leu Leu Thr Ser Ala Pro Ser Leu Ala
        515                 520                 525

Thr Ser Pro Ala Phe Arg Tyr Asp Leu Leu Asp Leu Thr Arg Gln Ala
    530                 535                 540

Val Gln Glu Leu Val Ser Leu Tyr Tyr Glu Glu Ala Arg Ser Ala Tyr
545                 550                 555                 560

Leu Ser Lys Glu Leu Ala Ser Leu Leu Arg Ala Gly Gly Val Leu Ala
                565                 570                 575

Tyr Glu Leu Leu Pro Ala Leu Asp Glu Val Leu Ala Ser Asp Ser Arg
            580                 585                 590

Phe Leu Leu Gly Ser Trp Leu Glu Gln Ala Arg Ala Ala Ala Val Ser
        595                 600                 605

Glu Ala Glu Ala Asp Phe Tyr Glu Gln Asn Ser Arg Tyr Gln Leu Thr
    610                 615                 620
```

```
Leu Trp Gly Pro Glu Gly Asn Ile Leu Asp Tyr Ala Asn Lys Gln Leu
625                 630                 635                 640

Ala Gly Leu Val Ala Asn Tyr Tyr Thr Pro Arg Trp Arg Leu Phe Leu
            645                 650                 655

Glu Ala Leu Val Asp Ser Val Ala Gln Gly Ile Pro Phe Gln Gln His
            660                 665                 670

Gln Phe Asp Lys Asn Val Phe Gln Leu Glu Gln Ala Phe Val Leu Ser
            675                 680                 685

Lys Gln Arg Tyr Pro Ser Gln Pro Arg Gly Asp Thr Val Asp Leu Ala
            690                 695                 700

Lys Lys Ile Phe Leu Lys Tyr Tyr Pro Arg Trp Val Ala Gly Ser Trp
705                 710                 715                 720

Gly Ala Pro Gly Gly Gly Gly Ala Ala Ala Ala Gly Gly Gly
            725                 730                 735

Gly Gly Gly Ala Pro Gly Gly Gly Gly Ala Ala Ala Ala Gly
            740                 745                 750

Gly Gly Gly Gly Ala Pro Gly Gly Gly Gly Ala Ala Ala
            755                 760                 765

Ala Gly Gly Gly Gly Ala Pro Asp Gly Gly Phe Cys Glu Val
770                 775                 780

Cys Lys Lys Leu Val Gly Tyr Leu Asp Arg Asn Leu Glu Lys Asn Ser
785                 790                 795                 800

Thr Lys Gln Glu Ile Leu Ala Ala Leu Glu Lys Gly Cys Ser Phe Leu
            805                 810                 815

Pro Asp Pro Tyr Gln Lys Gln Cys Asp Gln Phe Val Ala Glu Tyr Glu
            820                 825                 830

Pro Val Leu Ile Glu Ile Leu Val Glu Val Met Asp Pro Ser Phe Val
            835                 840                 845

Cys Leu Lys Ile Gly Ala Cys Pro Ser Ala His Lys Pro Leu Leu Gly
            850                 855                 860

Thr Glu Lys Cys Ile Trp Gly Pro Ser Tyr Trp Cys Gln Asn Thr Glu
865                 870                 875                 880

Thr Ala Ala Gln Cys Asn Ala Val Glu His Cys Lys Arg His Val Trp
            885                 890                 895

Asn

<210> SEQ ID NO 24
<211> LENGTH: 957
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Asp Glu Ala Arg Glu Ala Ala Val Arg Ala Leu Val Ala Arg Leu
1               5                   10                  15

Leu Gly Pro Gly Pro Ala Ala Asp Phe Ser Val Ser Val Glu Arg Ala
            20                  25                  30

Leu Ala Ala Lys Pro Gly Leu Asp Thr Tyr Ser Leu Gly Gly Gly Gly
            35                  40                  45

Ala Ala Arg Val Arg Val Arg Gly Ser Thr Gly Val Ala Ala Ala Ala
            50                  55                  60

Gly Leu His Arg Tyr Leu Arg Asp Phe Cys Gly Cys His Val Ala Trp
65                  70                  75                  80
```

```
Ser Gly Ser Gln Leu Arg Leu Pro Arg Pro Leu Pro Ala Val Pro Gly
             85                  90                  95

Glu Leu Thr Glu Ala Thr Pro Asn Arg Tyr Arg Tyr Gln Asn Val
        100                 105                 110

Cys Thr Gln Ser Tyr Ser Phe Val Trp Trp Asp Trp Ala Arg Trp Glu
            115                 120                 125

Arg Glu Ile Asp Trp Met Ala Leu Asn Gly Ile Asn Leu Ala Leu Ala
    130                 135                 140

Trp Ser Gly Gln Glu Ala Ile Trp Gln Arg Val Tyr Leu Ala Leu Gly
145                 150                 155                 160

Leu Thr Gln Ala Glu Ile Asn Glu Phe Phe Thr Gly Pro Ala Phe Leu
                165                 170                 175

Ala Trp Gly Arg Met Gly Asn Leu His Thr Trp Asp Gly Pro Leu Pro
            180                 185                 190

Pro Ser Trp His Ile Lys Gln Leu Tyr Leu Gln His Arg Val Leu Asp
            195                 200                 205

Gln Met Arg Ser Phe Gly Met Thr Pro Val Leu Pro Ala Phe Ala Gly
    210                 215                 220

His Val Pro Glu Ala Val Thr Arg Val Phe Pro Gln Val Asn Val Thr
225                 230                 235                 240

Lys Met Gly Ser Trp Gly His Phe Asn Cys Ser Tyr Ser Cys Ser Phe
                245                 250                 255

Leu Leu Ala Pro Glu Asp Pro Ile Phe Pro Ile Ile Gly Ser Leu Phe
            260                 265                 270

Leu Arg Glu Leu Ile Lys Glu Phe Gly Thr Asp His Ile Tyr Gly Ala
    275                 280                 285

Asp Thr Phe Asn Glu Met Gln Pro Pro Ser Ser Glu Pro Ser Tyr Leu
290                 295                 300

Ala Ala Ala Thr Thr Ala Val Tyr Glu Ala Met Thr Ala Val Asp Thr
305                 310                 315                 320

Glu Ala Val Trp Leu Leu Gln Gly Trp Leu Phe Gln His Gln Pro Gln
                325                 330                 335

Phe Trp Gly Pro Ala Gln Ile Arg Ala Val Leu Gly Ala Val Pro Arg
            340                 345                 350

Gly Arg Leu Leu Val Leu Asp Leu Phe Ala Glu Ser Gln Pro Val Tyr
            355                 360                 365

Thr Arg Thr Ala Ser Phe Gln Gly Gln Pro Phe Ile Trp Cys Met Leu
    370                 375                 380

His Asn Phe Gly Gly Asn His Gly Leu Phe Gly Ala Leu Glu Ala Val
385                 390                 395                 400

Asn Gly Gly Pro Glu Ala Ala Arg Leu Phe Pro Asn Ser Thr Met Val
                405                 410                 415

Gly Thr Gly Met Ala Pro Glu Gly Ile Ser Gln Asn Glu Val Val Tyr
            420                 425                 430

Ser Leu Met Ala Glu Leu Gly Trp Arg Lys Asp Pro Val Pro Asp Leu
            435                 440                 445

Ala Ala Trp Val Thr Ser Phe Ala Ala Arg Arg Tyr Gly Val Ser His
450                 455                 460

Pro Asp Ala Gly Ala Ala Trp Arg Leu Leu Leu Arg Ser Val Tyr Asn
465                 470                 475                 480

Cys Ser Gly Glu Ala Cys Arg Gly His Asn Arg Ser Pro Leu Val Arg
                485                 490                 495
```

```
Arg Pro Ser Leu Gln Met Asn Thr Ser Ile Trp Tyr Asn Arg Ser Asp
            500                 505                 510

Val Phe Glu Ala Trp Arg Leu Leu Leu Thr Ser Ala Pro Ser Leu Ala
        515                 520                 525

Thr Ser Pro Ala Phe Arg Tyr Asp Leu Leu Asp Leu Thr Arg Gln Ala
    530                 535                 540

Val Gln Glu Leu Val Ser Leu Tyr Tyr Glu Glu Ala Arg Ser Ala Tyr
545                 550                 555                 560

Leu Ser Lys Glu Leu Ala Ser Leu Leu Arg Ala Gly Gly Val Leu Ala
                565                 570                 575

Tyr Glu Leu Leu Pro Ala Leu Asp Glu Val Leu Ala Ser Asp Ser Arg
            580                 585                 590

Phe Leu Leu Gly Ser Trp Leu Glu Gln Ala Arg Ala Ala Ala Val Ser
        595                 600                 605

Glu Ala Glu Ala Asp Phe Tyr Glu Gln Asn Ser Arg Tyr Gln Leu Thr
    610                 615                 620

Leu Trp Gly Pro Glu Gly Asn Ile Leu Asp Tyr Ala Asn Lys Gln Leu
625                 630                 635                 640

Ala Gly Leu Val Ala Asn Tyr Tyr Thr Pro Arg Trp Arg Leu Phe Leu
                645                 650                 655

Glu Ala Leu Val Asp Ser Val Ala Gln Gly Ile Pro Phe Gln Gln His
            660                 665                 670

Gln Phe Asp Lys Asn Val Phe Gln Leu Glu Gln Ala Phe Val Leu Ser
        675                 680                 685

Lys Gln Arg Tyr Pro Ser Gln Pro Arg Gly Asp Thr Val Asp Leu Ala
    690                 695                 700

Lys Lys Ile Phe Leu Lys Tyr Tyr Pro Arg Trp Val Ala Gly Ser Trp
705                 710                 715                 720

Gly Ala Pro Gly Gly Gly Gly Ala Ala Ala Ala Gly Gly
                725                 730                 735

Gly Gly Gly Ala Pro Gly Gly Gly Gly Ala Ala Ala Ala Gly
            740                 745                 750

Gly Gly Gly Gly Ala Pro Gly Gly Gly Gly Ala Ala Ala Ala
        755                 760                 765

Ala Gly Gly Gly Gly Gly Ala Pro Ser Pro Leu Pro Ile Thr Pro
    770                 775                 780

Val Asn Ala Thr Cys Ala Ile Arg His Pro Cys His Asn Asn Leu Met
785                 790                 795                 800

Asn Ala Ile Arg Ala Gln Leu Ala Leu Asn Gly Ser Ala Asn Ala
                805                 810                 815

Leu Phe Ile Leu Tyr Tyr Thr Ala Gln Gly Glu Pro Phe Pro Asn Asn
            820                 825                 830

Leu Asp Lys Leu Cys Gly Pro Asn Val Thr Asp Phe Pro Pro Phe His
        835                 840                 845

Ala Asn Gly Thr Glu Lys Ala Lys Leu Val Glu Leu Tyr Arg Ile Val
    850                 855                 860

Val Tyr Leu Gly Thr Ser Leu Gly Asn Ile Thr Arg Asp Gln Lys Ile
865                 870                 875                 880

Leu Asn Pro Ser Ala Leu Ser Leu His Ser Lys Leu Asn Ala Thr Ala
                885                 890                 895

Asp Ile Leu Arg Gly Leu Leu Ser Asn Val Leu Cys Arg Leu Cys Ser
            900                 905                 910

Lys Tyr His Val Gly His Val Asp Val Thr Tyr Gly Pro Asp Thr Ser
```

```
                915                 920                 925
Gly Lys Asp Val Ala Gln Lys Ala Lys Leu Gly Cys Gln Leu Leu Gly
    930                 935                 940
Lys Tyr Lys Gln Ile Ile Ala Val Leu Ala Gln Ala Phe
945                 950                 955

<210> SEQ ID NO 25
<211> LENGTH: 962
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Asp Glu Ala Arg Glu Ala Ala Val Arg Ala Leu Val Ala Arg Leu
1               5                   10                  15

Leu Gly Pro Gly Pro Ala Ala Asp Phe Ser Val Ser Val Glu Arg Ala
            20                  25                  30

Leu Ala Ala Lys Pro Gly Leu Asp Thr Tyr Ser Leu Gly Gly Gly Gly
                35                  40                  45

Ala Ala Arg Val Arg Val Arg Gly Ser Thr Gly Val Ala Ala Ala Ala
    50                  55                  60

Gly Leu His Arg Tyr Leu Arg Asp Phe Cys Gly Cys His Val Ala Trp
65                  70                  75                  80

Ser Gly Ser Gln Leu Arg Leu Pro Arg Pro Leu Pro Ala Val Pro Gly
                85                  90                  95

Glu Leu Thr Glu Ala Thr Pro Asn Arg Tyr Arg Tyr Gln Asn Val
            100                 105                 110

Cys Thr Gln Ser Tyr Ser Phe Val Trp Trp Asp Trp Ala Arg Trp Glu
                115                 120                 125

Arg Glu Ile Asp Trp Met Ala Leu Asn Gly Ile Asn Leu Ala Leu Ala
    130                 135                 140

Trp Ser Gly Gln Glu Ala Ile Trp Gln Arg Val Tyr Leu Ala Leu Gly
145                 150                 155                 160

Leu Thr Gln Ala Glu Ile Asn Glu Phe Phe Thr Gly Pro Ala Phe Leu
                165                 170                 175

Ala Trp Gly Arg Met Gly Asn Leu His Thr Trp Asp Gly Pro Leu Pro
            180                 185                 190

Pro Ser Trp His Ile Lys Gln Leu Tyr Leu Gln His Arg Val Leu Asp
                195                 200                 205

Gln Met Arg Ser Phe Gly Met Thr Pro Val Leu Pro Ala Phe Ala Gly
    210                 215                 220

His Val Pro Glu Ala Val Thr Arg Val Phe Pro Gln Val Asn Val Thr
225                 230                 235                 240

Lys Met Gly Ser Trp Gly His Phe Asn Cys Ser Tyr Ser Cys Ser Phe
                245                 250                 255

Leu Leu Ala Pro Glu Asp Pro Ile Phe Pro Ile Ile Gly Ser Leu Phe
            260                 265                 270

Leu Arg Glu Leu Ile Lys Glu Phe Gly Thr Asp His Ile Tyr Gly Ala
        275                 280                 285

Asp Thr Phe Asn Glu Met Gln Pro Pro Ser Ser Glu Pro Ser Tyr Leu
    290                 295                 300

Ala Ala Ala Thr Thr Ala Val Tyr Glu Ala Met Thr Ala Val Asp Thr
305                 310                 315                 320
```

```
Glu Ala Val Trp Leu Leu Gln Gly Trp Leu Phe Gln His Gln Pro Gln
                325                 330                 335

Phe Trp Gly Pro Ala Gln Ile Arg Ala Val Leu Gly Ala Val Pro Arg
                340                 345                 350

Gly Arg Leu Leu Val Leu Asp Leu Phe Ala Glu Ser Gln Pro Val Tyr
                355                 360                 365

Thr Arg Thr Ala Ser Phe Gln Gly Gln Pro Phe Ile Trp Cys Met Leu
    370                 375                 380

His Asn Phe Gly Gly Asn His Gly Leu Phe Gly Ala Leu Glu Ala Val
385                 390                 395                 400

Asn Gly Gly Pro Glu Ala Ala Arg Leu Phe Pro Asn Ser Thr Met Val
                405                 410                 415

Gly Thr Gly Met Ala Pro Glu Gly Ile Ser Gln Asn Glu Val Val Tyr
                420                 425                 430

Ser Leu Met Ala Glu Leu Gly Trp Arg Lys Asp Pro Val Pro Asp Leu
            435                 440                 445

Ala Ala Trp Val Thr Ser Phe Ala Arg Arg Tyr Gly Val Ser His
        450                 455                 460

Pro Asp Ala Gly Ala Ala Trp Arg Leu Leu Arg Ser Val Tyr Asn
465                 470                 475                 480

Cys Ser Gly Glu Ala Cys Arg Gly His Asn Arg Ser Pro Leu Val Arg
                485                 490                 495

Arg Pro Ser Leu Gln Met Asn Thr Ser Ile Trp Tyr Asn Arg Ser Asp
                500                 505                 510

Val Phe Glu Ala Trp Arg Leu Leu Thr Ser Ala Pro Ser Leu Ala
            515                 520                 525

Thr Ser Pro Ala Phe Arg Tyr Asp Leu Leu Asp Leu Thr Arg Gln Ala
            530                 535                 540

Val Gln Glu Leu Val Ser Leu Tyr Tyr Glu Glu Ala Arg Ser Ala Tyr
545                 550                 555                 560

Leu Ser Lys Glu Leu Ala Ser Leu Leu Arg Ala Gly Val Leu Ala
                565                 570                 575

Tyr Glu Leu Leu Pro Ala Leu Asp Glu Val Leu Ala Ser Asp Ser Arg
            580                 585                 590

Phe Leu Leu Gly Ser Trp Leu Glu Gln Ala Arg Ala Ala Ala Val Ser
            595                 600                 605

Glu Ala Glu Ala Asp Phe Tyr Glu Gln Asn Ser Arg Tyr Gln Leu Thr
610                 615                 620

Leu Trp Gly Pro Glu Gly Asn Ile Leu Asp Tyr Ala Asn Lys Gln Leu
625                 630                 635                 640

Ala Gly Leu Val Ala Asn Tyr Tyr Thr Pro Arg Trp Arg Leu Phe Leu
                645                 650                 655

Glu Ala Leu Val Asp Ser Val Ala Gln Gly Ile Pro Phe Gln Gln His
                660                 665                 670

Gln Phe Asp Lys Asn Val Phe Gln Leu Glu Gln Ala Phe Val Leu Ser
            675                 680                 685

Lys Gln Arg Tyr Pro Ser Gln Pro Arg Gly Asp Thr Val Asp Leu Ala
            690                 695                 700

Lys Lys Ile Phe Leu Lys Tyr Tyr Pro Arg Trp Val Ala Gly Ser Trp
705                 710                 715                 720

Gly Ala Pro Gly Gly Gly Gly Ala Ala Ala Ala Gly Gly
                725                 730                 735
```

Gly Gly Gly Ala Pro Gly Gly Gly Gly Ala Ala Ala Ala Gly
            740                 745                 750

Gly Gly Gly Gly Gly Ala Pro Gly Gly Gly Gly Ala Ala Ala
            755                 760                 765

Ala Gly Gly Gly Gly Gly Ala Pro Arg Gly Gly Arg Asp His Gly
            770                 775                 780

Asp Trp Asp Glu Ala Ser Arg Leu Pro Pro Leu Pro Pro Arg Glu Asp
785                 790                 795                 800

Ala Ala Arg Val Ala Arg Phe Val Thr His Val Ser Asp Trp Gly Ala
                805                 810                 815

Leu Ala Thr Ile Ser Thr Leu Glu Ala Val Arg Gly Arg Pro Phe Ala
                820                 825                 830

Asp Val Leu Ser Leu Ser Asp Gly Pro Pro Gly Ala Gly Ser Gly Val
                835                 840                 845

Pro Tyr Phe Tyr Leu Ser Pro Leu Gln Leu Ser Val Ser Asn Leu Gln
                850                 855                 860

Glu Asn Pro Tyr Ala Thr Leu Thr Met Thr Leu Ala Gln Thr Asn Phe
865                 870                 875                 880

Cys Lys Lys His Gly Phe Pro Leu Cys Val His Ile Met Leu Ser Gly
                885                 890                 895

Thr Val Thr Lys Val Asn Glu Thr Glu Met Asp Ile Ala Lys His Ser
                900                 905                 910

Leu Phe Ile Arg His Pro Glu Met Lys Thr Trp Pro Ser Ser His Asn
                915                 920                 925

Trp Phe Phe Ala Lys Leu Asn Ile Thr Asn Ile Trp Val Leu Asp Tyr
                930                 935                 940

Phe Gly Gly Pro Lys Ile Val Thr Pro Glu Glu Tyr Tyr Asn Val Thr
945                 950                 955                 960

Val Gln

```
<210> SEQ ID NO 26
<211> LENGTH: 837
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 26

Asp Glu Ala Arg Glu Ala Ala Val Arg Ala Leu Val Ala Arg Leu
1               5                   10                  15

Leu Gly Pro Gly Pro Ala Ala Asp Phe Ser Val Ser Val Glu Arg Ala
                20                  25                  30

Leu Ala Ala Lys Pro Gly Leu Asp Thr Tyr Ser Leu Gly Gly Gly
            35                  40                  45

Ala Ala Arg Val Arg Val Arg Gly Ser Thr Gly Val Ala Ala Ala
            50                  55                  60

Gly Leu His Arg Tyr Leu Arg Asp Phe Cys Gly Cys His Val Ala Trp
65                  70                  75                  80

Ser Gly Ser Gln Leu Arg Leu Pro Arg Pro Leu Pro Ala Val Pro Gly
                85                  90                  95

Glu Leu Thr Glu Ala Thr Pro Asn Arg Tyr Arg Tyr Gln Asn Val
            100                 105                 110

Cys Thr Gln Ser Tyr Ser Phe Val Trp Trp Asp Trp Ala Arg Trp Glu
                115                 120                 125

-continued

```
Arg Glu Ile Asp Trp Met Ala Leu Asn Gly Ile Asn Leu Ala Leu Ala
    130                 135                 140

Trp Ser Gln Glu Ala Ile Trp Gln Arg Val Tyr Leu Ala Leu Gly
145                 150                 155                 160

Leu Thr Gln Ala Glu Ile Asn Glu Phe Phe Thr Gly Pro Ala Phe Leu
                165                 170                 175

Ala Trp Gly Arg Met Gly Asn Leu His Thr Trp Asp Gly Pro Leu Pro
                180                 185                 190

Pro Ser Trp His Ile Lys Gln Leu Tyr Leu Gln His Arg Val Leu Asp
        195                 200                 205

Gln Met Arg Ser Phe Gly Met Thr Pro Val Leu Pro Ala Phe Ala Gly
    210                 215                 220

His Val Pro Glu Ala Val Thr Arg Val Phe Pro Gln Val Asn Val Thr
225                 230                 235                 240

Lys Met Gly Ser Trp Gly His Phe Asn Cys Ser Tyr Ser Cys Ser Phe
                245                 250                 255

Leu Leu Ala Pro Glu Asp Pro Ile Phe Pro Ile Ile Gly Ser Leu Phe
                260                 265                 270

Leu Arg Glu Leu Ile Lys Glu Phe Gly Thr Asp His Ile Tyr Gly Ala
        275                 280                 285

Asp Thr Phe Asn Glu Met Gln Pro Pro Ser Ser Glu Pro Ser Tyr Leu
    290                 295                 300

Ala Ala Ala Thr Thr Ala Val Tyr Glu Ala Met Thr Ala Val Asp Thr
305                 310                 315                 320

Glu Ala Val Trp Leu Leu Gln Gly Trp Leu Phe Gln His Gln Pro Gln
                325                 330                 335

Phe Trp Gly Pro Ala Gln Ile Arg Ala Val Leu Gly Ala Val Pro Arg
                340                 345                 350

Gly Arg Leu Leu Val Leu Asp Leu Phe Ala Glu Ser Gln Pro Val Tyr
        355                 360                 365

Thr Arg Thr Ala Ser Phe Gln Gly Gln Pro Phe Ile Trp Cys Met Leu
    370                 375                 380

His Asn Phe Gly Gly Asn His Gly Leu Phe Gly Ala Leu Glu Ala Val
385                 390                 395                 400

Asn Gly Gly Pro Glu Ala Ala Arg Leu Phe Pro Asn Ser Thr Met Val
                405                 410                 415

Gly Thr Gly Met Ala Pro Glu Gly Ile Ser Gln Asn Glu Val Val Tyr
                420                 425                 430

Ser Leu Met Ala Glu Leu Gly Trp Arg Lys Asp Pro Val Pro Asp Leu
        435                 440                 445

Ala Ala Trp Val Thr Ser Phe Ala Ala Arg Arg Tyr Gly Val Ser His
450                 455                 460

Pro Asp Ala Gly Ala Ala Trp Arg Leu Leu Leu Arg Ser Val Tyr Asn
465                 470                 475                 480

Cys Ser Gly Glu Ala Cys Arg Gly His Asn Arg Ser Pro Leu Val Arg
                485                 490                 495

Arg Pro Ser Leu Gln Met Asn Thr Ser Ile Trp Tyr Asn Arg Ser Asp
            500                 505                 510

Val Phe Glu Ala Trp Arg Leu Leu Leu Thr Ser Ala Pro Ser Leu Ala
        515                 520                 525

Thr Ser Pro Ala Phe Arg Tyr Asp Leu Leu Asp Leu Thr Arg Gln Ala
    530                 535                 540
```

| | | | | | | | | | | | | | | | |
|---|---|---|---|---|---|---|---|---|---|---|---|---|---|---|---|
|Val|Gln|Glu|Leu|Val|Ser|Leu|Tyr|Tyr|Glu|Glu|Ala|Arg|Ser|Ala|Tyr|
|545| | | | |550| | | | |555| | | | |560|

| | | | | | | | | | | | | | | | |
|---|---|---|---|---|---|---|---|---|---|---|---|---|---|---|---|
|Leu|Ser|Lys|Glu|Leu|Ala|Ser|Leu|Leu|Arg|Ala|Gly|Gly|Val|Leu|Ala|
| | | | | |565| | | | |570| | | | |575|

| | | | | | | | | | | | | | | | |
|---|---|---|---|---|---|---|---|---|---|---|---|---|---|---|---|
|Tyr|Glu|Leu|Leu|Pro|Ala|Leu|Asp|Glu|Val|Leu|Ala|Ser|Asp|Ser|Arg|
| | | | |580| | | | |585| | | | |590| |

| | | | | | | | | | | | | | | | |
|---|---|---|---|---|---|---|---|---|---|---|---|---|---|---|---|
|Phe|Leu|Leu|Gly|Ser|Trp|Leu|Glu|Gln|Ala|Arg|Ala|Ala|Ala|Val|Ser|
| | | |595| | | | |600| | | | |605| | |

| | | | | | | | | | | | | | | | |
|---|---|---|---|---|---|---|---|---|---|---|---|---|---|---|---|
|Glu|Ala|Glu|Ala|Asp|Phe|Tyr|Glu|Gln|Asn|Ser|Arg|Tyr|Gln|Leu|Thr|
| | |610| | | | |615| | | | |620| | | |

| | | | | | | | | | | | | | | | |
|---|---|---|---|---|---|---|---|---|---|---|---|---|---|---|---|
|Leu|Trp|Gly|Pro|Glu|Gly|Asn|Ile|Leu|Asp|Tyr|Ala|Asn|Lys|Gln|Leu|
|625| | | | |630| | | | |635| | | | |640|

| | | | | | | | | | | | | | | | |
|---|---|---|---|---|---|---|---|---|---|---|---|---|---|---|---|
|Ala|Gly|Leu|Val|Ala|Asn|Tyr|Tyr|Thr|Pro|Arg|Trp|Arg|Leu|Phe|Leu|
| | | | |645| | | | |650| | | | |655| |

| | | | | | | | | | | | | | | | |
|---|---|---|---|---|---|---|---|---|---|---|---|---|---|---|---|
|Glu|Ala|Leu|Val|Asp|Ser|Val|Ala|Gln|Gly|Ile|Pro|Phe|Gln|Gln|His|
| | | |660| | | | |665| | | | |670| | |

| | | | | | | | | | | | | | | | |
|---|---|---|---|---|---|---|---|---|---|---|---|---|---|---|---|
|Gln|Phe|Asp|Lys|Asn|Val|Phe|Gln|Leu|Glu|Gln|Ala|Phe|Val|Leu|Ser|
| | |675| | | | |680| | | | |685| | | |

| | | | | | | | | | | | | | | | |
|---|---|---|---|---|---|---|---|---|---|---|---|---|---|---|---|
|Lys|Gln|Arg|Tyr|Pro|Ser|Gln|Pro|Arg|Gly|Asp|Thr|Val|Asp|Leu|Ala|
| |690| | | | |695| | | | |700| | | | |

| | | | | | | | | | | | | | | | |
|---|---|---|---|---|---|---|---|---|---|---|---|---|---|---|---|
|Lys|Lys|Ile|Phe|Leu|Lys|Tyr|Tyr|Pro|Arg|Trp|Val|Ala|Gly|Ser|Trp|
|705| | | | |710| | | | |715| | | | |720|

| | | | | | | | | | | | | | | | |
|---|---|---|---|---|---|---|---|---|---|---|---|---|---|---|---|
|Gly|Ala|Pro|Gly|Gly|Gly|Gly|Ala|Ala|Ala|Ala|Gly|Gly|Gly|Gly|Gly|
| | | | |725| | | | |730| | | | |735| |

| | | | | | | | | | | | | | | | |
|---|---|---|---|---|---|---|---|---|---|---|---|---|---|---|---|
|Gly|Gly|Gly|Ala|Pro|Gly|Gly|Gly|Gly|Ala|Ala|Ala|Ala|Gly|Gly|Gly|
| | | |740| | | | |745| | | | |750| | |

| | | | | | | | | | | | | | | | |
|---|---|---|---|---|---|---|---|---|---|---|---|---|---|---|---|
|Gly|Gly|Gly|Gly|Gly|Ala|Pro|Gly|Gly|Gly|Gly|Ala|Ala|Ala|Ala|Ala|
| | |755| | | | |760| | | | |765| | | |

| | | | | | | | | | | | | | | | |
|---|---|---|---|---|---|---|---|---|---|---|---|---|---|---|---|
|Ala|Gly|Gly|Gly|Gly|Gly|Ala|Pro|Leu|Cys|Gly|Gly|Glu|Leu|Val|
|770| | | | |775| | | | |780| | | | | |

| | | | | | | | | | | | | | | | |
|---|---|---|---|---|---|---|---|---|---|---|---|---|---|---|---|
|Asp|Thr|Leu|Gln|Phe|Val|Cys|Gly|Asp|Arg|Gly|Phe|Tyr|Phe|Ser|Arg|
|785| | | | |790| | | | |795| | | | |800|

| | | | | | | | | | | | | | | | |
|---|---|---|---|---|---|---|---|---|---|---|---|---|---|---|---|
|Pro|Ala|Ser|Arg|Val|Ser|Arg|Arg|Ser|Arg|Gly|Ile|Val|Glu|Glu|Cys|
| | | | |805| | | | |810| | | | |815| |

| | | | | | | | | | | | | | | | |
|---|---|---|---|---|---|---|---|---|---|---|---|---|---|---|---|
|Cys|Phe|Arg|Ser|Cys|Asp|Leu|Ala|Leu|Leu|Glu|Thr|Tyr|Cys|Ala|Thr|
| | | |820| | | | |825| | | | |830| | |

| | | | |
|---|---|---|---|
|Pro|Ala|Lys|Ser|Glu|
| | | |835|

```
<210> SEQ ID NO 27
<211> LENGTH: 3771
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27
atgctgttca agctcctgca gagacagacc tataccctgcc tgtcccacag gtatgggctc      60
tacgtgtgct tcttgggcgt cgttgtcacc atcgtctccg ccttccagtt cggagaggtg     120
gttctggaat ggagccgaga tcaataccat gttttgtttg attcctatag agacaatatt     180
gctggaaagt cctttcagaa tcggctttgt ctgcccatgc cgattgacgt tgtttacacc     240
tgggtgaatg gcacagatct tgaactactg aaggaactac agcaggtcag agaacagatg     300
```

-continued

```
gaggaggagc agaaagcaat gagagaaatc cttgggaaaa acacaacgga acctactaag      360
aagagtgaga agcagttaga gtgtttgcta acacactgca ttaaggtgcc aatgcttgtc      420
ctggacccag ccctgccagc aacatcacc  ctgaaggacc tgccatctct ttatccttct      480
tttcattctg ccagtgacat tttcaatgtt gcaaaaccaa aaaacccttc taccaatgtc      540
tcagttgttg tttttgacag tactaaggat gttgaagatg cccactctgg actgcttaaa      600
ggaaatagca gacagacagt atggagggc  tacttgacaa cagataaaga agtccctgga      660
ttagtgctaa tgcaagattt ggctttcctg agtggatttc caccaacatt caaggaaaca      720
aatcaactaa aaacaaaatt gccagaaaat ctttcctcta aagtcaaact gttgcagttg      780
tattcagagg ccagtgtagc gcttctaaaa ctgaataacc ccaaggattt tcaagaattg      840
aataagcaaa ctaagaagaa catgaccatt gatggaaaag aactgaccat aagtcctgca      900
tatttattat gggatctgag cgccatcagc cagtctaagc aggatgaaga catctctgcc      960
agtcgttttg aagataacga agaactgagg tactcattgc gatctatcga gaggcatgca     1020
ccatgggttc ggaatatttt cattgtcacc aacgggcaga ttccatcctg gctgaacctt     1080
gacaatcctc gagtgacaat agtaacacac caggatgttt ttcgaaattt gagccacttg     1140 cctacctta  gttcacctgc tattgaaagt cacattcatc gcatcgaagg gctgtcccag     1200
aagtttattt acctaaatga tgatgtcatg tttgggaagg atgtctggcc agatgatttt     1260
tacagtcact ccaaaggcca gaaggttat  ttgacatggc ctgtgccaaa ctgtgccgag     1320
ggctgcccag gttcctggat taaggatggc tattgtgaca aggcttgtaa taattcagcc     1380
tgcgattggg atggtgggga ttgctctgga aacagtggag ggagtcgcta tattgcagga     1440
ggtggaggta ctgggagtat tggagttgga cagccctggc agtttggtgg aggaataaac     1500
agtgtctctt actgtaatca gggatgtgcg aattcctggc tcgctgataa gttctgtgac     1560
caagcatgca atgtcttgtc ctgtgggttt gatgctggcg actgtgggca agatcatttt     1620
catgaattgt ataaagtgat ccttctccca aaccagactc actatattat tccaaaaggt     1680
gaatgcctgc cttatttcag ctttgcagaa gtagccaaaa gaggagttga aggtgcctat     1740
agtgacaatc caataattcg acatgcttct attgccaaca agtggaaaac catccacctc     1800
ataatgcaca gtggaatgaa tgccaccaca atacatttta atctcacgtt tcaaaataca     1860
aacgatgaag agttcaaaat gcagataaca gtggaggtgg acacaaggga gggaccaaaa     1920
ctgaattcta cagcccagaa gggttacgaa aatttagtta gtcccataac acttcttcca     1980
gaggcggaaa tccttttga  ggatattccc aaagaaaaac gcttcccgaa gtttaagaga     2040
catgatgtta actcaacaag gagagcccag gaagaggtga aaattcccct ggtaaatatt     2100
tcactccttc caaaagacgc ccagttgagt ctcaatacct tggatttgca actggaacat     2160
ggagacatca ctttgaaagg atacaatttg tccaagtcag ccttgctgag atcatttctg     2220
atgaactcac agcatgctaa aataaaaaat caagctataa taacagatga aacaaatgac     2280
agtttggtgg ctccacagga aaaacaggtt cataaaagca tcttgccaaa cagcttagga     2340
gtgtctgaaa gattgcagag gttgactttt cctgcagtga gtgtaaaagt gaatggtcat     2400
gaccagggtc agaatccacc cctggacttg agaccacag  caagatttag agtggaaact     2460
cacacccaaa aaaccatagg cggaaatgtg acaaagaaa  agcccccatc tctgattgtt     2520
ccactggaaa gccagatgac aaaagaaaag aaaatcacag ggaaagaaaa agagaacagt     2580
agaatggagg aaaatgctga aaatcacata ggcgttactg aagtgttact tggaagaaag     2640
ctgcagcatt acacagatag ttacttgggc ttttttgccat gggagaaaaa aaagtatttc     2700
```

-continued

```
caagatcttc tcgacgaaga agagtcattg aagacacaat tggcatactt cactgatagc    2760
aaaaatactg ggaggcaact aaaagataca tttgcagatt ccctcagata tgtaaataaa    2820
attctaaata gcaagtttgg attcacatcg cggaaagtcc ctgctcacat gcctcacatg    2880
attgaccgga ttgttatgca agaactgcaa gatatgttcc ctgaagaatt tgacaagacg    2940
tcatttcaca aagtgcgcca ttctgaggat atgcagtttg ccttctctta tttttattat    3000
ctcatgagtg cagtgcagcc actgaatata tctcaagtct tgatgaagt tgatacagat     3060 caatctggtg tcttgtctga cagagaaatc cgaacactgg ctaccagaat tcacgaactg    3120
ccgttaagtt tgcaggattt gacaggtctg gaacacatgc taataaattg ctcaaaaatg    3180
cttcctgctg atatcacgca gctaaataat attccaccaa ctcaggaatc ctactatgat    3240
cccaacctgc caccggtcac taaaagtcta gtaacaaact gtaaaccagt aactgacaaa    3300
atccacaaag catataagga caaaaacaaa tataggtttg aaatcatggg agaagaagaa    3360 atcgcttta aaatgattcg taccaacgtt tctcatgtgg ttggccagtt ggatgacata    3420
agaaaaaacc ctaggaagtt tgtttgcctg aatgacaaca ttgaccacaa tcataaagat    3480
gctcagacag tgaaggctgt tctcagggac ttctatgaat ccatgttccc catacctccc    3540
caatttgaac tgccaagaga gtatcgaaac cgtttccttc atatgcatga gctgcaggaa    3600
tggagggctt atcgagacaa attgaagttt tggacccatt gtgtactagc aacattgatt    3660
atgtttacta tattctcatt tttgctgag cagttaattg cacttaagcg gaagatattt     3720
cccagaagga ggatacacaa agaagctagt cccaatcgaa tcagagtata g             3771
```

<210> SEQ ID NO 28
<211> LENGTH: 1256
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 28

```
Met Leu Phe Lys Leu Leu Gln Arg Gln Thr Tyr Thr Cys Leu Ser His
1               5                   10                  15

Arg Tyr Gly Leu Tyr Val Cys Phe Leu Gly Val Val Thr Ile Val
            20                  25                  30

Ser Ala Phe Gln Phe Gly Glu Val Val Leu Glu Trp Ser Arg Asp Gln
        35                  40                  45

Tyr His Val Leu Phe Asp Ser Tyr Arg Asp Asn Ile Ala Gly Lys Ser
    50                  55                  60

Phe Gln Asn Arg Leu Cys Leu Pro Met Pro Ile Asp Val Val Tyr Thr
65                  70                  75                  80

Trp Val Asn Gly Thr Asp Leu Glu Leu Leu Lys Glu Leu Gln Gln Val
                85                  90                  95

Arg Glu Gln Met Glu Glu Glu Gln Lys Ala Met Arg Glu Ile Leu Gly
            100                 105                 110

Lys Asn Thr Thr Glu Pro Thr Lys Lys Ser Glu Lys Gln Leu Glu Cys
        115                 120                 125

Leu Leu Thr His Cys Ile Lys Val Pro Met Leu Val Leu Asp Pro Ala
    130                 135                 140

Leu Pro Ala Asn Ile Thr Leu Lys Asp Leu Pro Ser Leu Tyr Pro Ser
145                 150                 155                 160
```

```
Phe His Ser Ala Ser Asp Ile Phe Asn Val Ala Lys Pro Lys Asn Pro
                165                 170                 175
Ser Thr Asn Val Ser Val Val Phe Asp Ser Thr Lys Asp Val Glu
            180                 185                 190
Asp Ala His Ser Gly Leu Leu Lys Gly Asn Ser Arg Gln Thr Val Trp
            195                 200                 205
Arg Gly Tyr Leu Thr Thr Asp Lys Glu Val Pro Gly Leu Val Leu Met
210                 215                 220
Gln Asp Leu Ala Phe Leu Ser Gly Phe Pro Thr Phe Lys Glu Thr
225                 230                 235                 240
Asn Gln Leu Lys Thr Lys Leu Pro Glu Asn Leu Ser Ser Lys Val Lys
                245                 250                 255
Leu Leu Gln Leu Tyr Ser Glu Ala Ser Val Ala Leu Leu Lys Leu Asn
                260                 265                 270
Asn Pro Lys Asp Phe Gln Glu Leu Asn Lys Gln Thr Lys Lys Asn Met
            275                 280                 285
Thr Ile Asp Gly Lys Glu Leu Thr Ile Ser Pro Ala Tyr Leu Leu Trp
            290                 295                 300
Asp Leu Ser Ala Ile Ser Gln Ser Lys Gln Asp Glu Asp Ile Ser Ala
305                 310                 315                 320
Ser Arg Phe Glu Asp Asn Glu Glu Leu Arg Tyr Ser Leu Arg Ser Ile
                325                 330                 335
Glu Arg His Ala Pro Trp Val Arg Asn Ile Phe Ile Val Thr Asn Gly
                340                 345                 350
Gln Ile Pro Ser Trp Leu Asn Leu Asp Asn Pro Arg Val Thr Ile Val
            355                 360                 365
Thr His Gln Asp Val Phe Arg Asn Leu Ser His Leu Pro Thr Phe Ser
            370                 375                 380
Ser Pro Ala Ile Glu Ser His Ile His Arg Ile Glu Gly Leu Ser Gln
385                 390                 395                 400
Lys Phe Ile Tyr Leu Asn Asp Asp Val Met Phe Gly Lys Asp Val Trp
                405                 410                 415
Pro Asp Asp Phe Tyr Ser His Ser Lys Gly Gln Lys Val Tyr Leu Thr
            420                 425                 430
Trp Pro Val Pro Asn Cys Ala Glu Gly Cys Pro Gly Ser Trp Ile Lys
            435                 440                 445
Asp Gly Tyr Cys Asp Lys Ala Cys Asn Asn Ser Ala Cys Asp Trp Asp
450                 455                 460
Gly Gly Asp Cys Ser Gly Asn Ser Gly Gly Ser Arg Tyr Ile Ala Gly
465                 470                 475                 480
Gly Gly Gly Thr Gly Ser Ile Gly Val Gly Gln Pro Trp Gln Phe Gly
                485                 490                 495
Gly Gly Ile Asn Ser Val Ser Tyr Cys Asn Gln Gly Cys Ala Asn Ser
            500                 505                 510
Trp Leu Ala Asp Lys Phe Cys Asp Gln Ala Cys Asn Val Leu Ser Cys
            515                 520                 525
Gly Phe Asp Ala Gly Asp Cys Gly Gln Asp His Phe His Glu Leu Tyr
530                 535                 540
Lys Val Ile Leu Leu Pro Asn Gln Thr His Tyr Ile Ile Pro Lys Gly
545                 550                 555                 560
Glu Cys Leu Pro Tyr Phe Ser Phe Ala Glu Val Ala Lys Arg Gly Val
                565                 570                 575
Glu Gly Ala Tyr Ser Asp Asn Pro Ile Ile Arg His Ala Ser Ile Ala
```

```
                580                 585                 590
Asn Lys Trp Lys Thr Ile His Leu Ile Met His Ser Gly Met Asn Ala
            595                 600                 605

Thr Thr Ile His Phe Asn Leu Thr Phe Gln Asn Thr Asn Asp Glu Glu
610                 615                 620

Phe Lys Met Gln Ile Thr Val Glu Val Asp Thr Arg Glu Gly Pro Lys
625                 630                 635                 640

Leu Asn Ser Thr Ala Gln Lys Gly Tyr Glu Asn Leu Val Ser Pro Ile
            645                 650                 655

Thr Leu Leu Pro Glu Ala Glu Ile Leu Phe Glu Asp Ile Pro Lys Glu
                660                 665                 670

Lys Arg Phe Pro Lys Phe Lys Arg His Asp Val Asn Ser Thr Arg Arg
            675                 680                 685

Ala Gln Glu Glu Val Lys Ile Pro Leu Val Asn Ile Ser Leu Leu Pro
                690                 695                 700

Lys Asp Ala Gln Leu Ser Leu Asn Thr Leu Asp Leu Gln Leu Glu His
705                 710                 715                 720

Gly Asp Ile Thr Leu Lys Gly Tyr Asn Leu Ser Lys Ser Ala Leu Leu
                725                 730                 735

Arg Ser Phe Leu Met Asn Ser Gln His Ala Lys Ile Lys Asn Gln Ala
                740                 745                 750

Ile Ile Thr Asp Glu Thr Asn Asp Ser Leu Val Ala Pro Gln Glu Lys
                755                 760                 765

Gln Val His Lys Ser Ile Leu Pro Asn Ser Leu Gly Val Ser Glu Arg
            770                 775                 780

Leu Gln Arg Leu Thr Phe Pro Ala Val Ser Val Lys Val Asn Gly His
785                 790                 795                 800

Asp Gln Gly Gln Asn Pro Pro Leu Asp Leu Glu Thr Thr Ala Arg Phe
                805                 810                 815

Arg Val Glu Thr His Thr Gln Lys Thr Ile Gly Gly Asn Val Thr Lys
                820                 825                 830

Glu Lys Pro Pro Ser Leu Ile Val Pro Leu Glu Ser Gln Met Thr Lys
            835                 840                 845

Glu Lys Lys Ile Thr Gly Lys Glu Lys Glu Asn Ser Arg Met Glu Glu
850                 855                 860

Asn Ala Glu Asn His Ile Gly Val Thr Glu Val Leu Leu Gly Arg Lys
865                 870                 875                 880

Leu Gln His Tyr Thr Asp Ser Tyr Leu Gly Phe Leu Pro Trp Glu Lys
                885                 890                 895

Lys Lys Tyr Phe Gln Asp Leu Leu Asp Glu Glu Ser Leu Lys Thr
            900                 905                 910

Gln Leu Ala Tyr Phe Thr Asp Ser Lys Asn Thr Gly Arg Gln Leu Lys
                915                 920                 925

Asp Thr Phe Ala Asp Ser Leu Arg Tyr Val Asn Lys Ile Leu Asn Ser
            930                 935                 940

Lys Phe Gly Phe Thr Ser Arg Lys Val Pro Ala His Met Pro His Met
945                 950                 955                 960

Ile Asp Arg Ile Val Met Gln Glu Leu Gln Asp Met Phe Pro Glu Glu
                965                 970                 975

Phe Asp Lys Thr Ser Phe His Lys Val Arg His Ser Glu Asp Met Gln
            980                 985                 990

Phe Ala Phe Ser Tyr Phe Tyr Tyr Leu Met Ser Ala Val Gln Pro Leu
            995                 1000                1005
```

Asn Ile Ser Gln Val Phe Asp Glu Val Asp Thr Asp Gln Ser Gly
1010                1015                1020

Val Leu Ser Asp Arg Glu Ile Arg Thr Leu Ala Thr Arg Ile His
1025                1030                1035

Glu Leu Pro Leu Ser Leu Gln Asp Leu Thr Gly Leu Glu His Met
1040                1045                1050

Leu Ile Asn Cys Ser Lys Met Leu Pro Ala Asp Ile Thr Gln Leu
1055                1060                1065

Asn Asn Ile Pro Pro Thr Gln Glu Ser Tyr Tyr Asp Pro Asn Leu
1070                1075                1080

Pro Pro Val Thr Lys Ser Leu Val Thr Asn Cys Lys Pro Val Thr
1085                1090                1095

Asp Lys Ile His Lys Ala Tyr Lys Asp Lys Asn Lys Tyr Arg Phe
1100                1105                1110

Glu Ile Met Gly Glu Glu Glu Ile Ala Phe Lys Met Ile Arg Thr
1115                1120                1125

Asn Val Ser His Val Val Gly Gln Leu Asp Asp Ile Arg Lys Asn
1130                1135                1140

Pro Arg Lys Phe Val Cys Leu Asn Asp Asn Ile Asp His Asn His
1145                1150                1155

Lys Asp Ala Gln Thr Val Lys Ala Val Leu Arg Asp Phe Tyr Glu
1160                1165                1170

Ser Met Phe Pro Ile Pro Ser Gln Phe Glu Leu Pro Arg Glu Tyr
1175                1180                1185

Arg Asn Arg Phe Leu His Met His Glu Leu Gln Glu Trp Arg Ala
1190                1195                1200

Tyr Arg Asp Lys Leu Lys Phe Trp Thr His Cys Val Leu Ala Thr
1205                1210                1215

Leu Ile Met Phe Thr Ile Phe Ser Phe Phe Ala Glu Gln Leu Ile
1220                1225                1230

Ala Leu Lys Arg Lys Ile Phe Pro Arg Arg Ile His Lys Glu
1235                1240                1245

Ala Ser Pro Asn Arg Ile Arg Val
1250                1255

<210> SEQ ID NO 29
<211> LENGTH: 918
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 29
atggcggcgg ggctggcgcg gctcctgttg ctcctcgggc tctcggccgg cgggcccgcg      60
ccggcaggtg cagcgaagat gaaggtggtg gaggagccca acgcgtttgg ggtgaacaac     120
ccgttcttgc ctcaggccag tcgcctccag gccaagaggg atccttcacc cgtgtctgga     180
cccgtgcatc tcttccgact ctcgggcaag tgcttcagcc tggtggagtc cacgtacaag     240
tatgagttct gcccgttcca caacgtgacc cagcacgagc agaccttccg ctggaacgcc     300
tacagtggga tcctcggcat ctggcacgag tgggagatcg ccaacaacac cttcacgggc     360
atgtggatga gggacggtga cgcctgccgt tcccggagcc ggcagagcaa ggtggagctg     420
gcgtgtggaa aaagcaaccg gctggcccat gtgtccgagc cgagcacctg cgtctacgcg     480

```
ctgacgttcg agaccccct cgtctgccac ccccacgcct tgctagtgta cccaaccctg    540
ccagaggccc tgcagcggca gtgggaccag gtagagcagg acctggccga tgagctgatc   600 acccccagg gccatgagaa gttgctgagg acactttttg aggatgctgg ctacttaaag    660
accccagaag aaaatgaacc cacccagctg gagggaggtc ctgacagctt ggggtttgag   720
accctggaaa actgcaggaa ggctcataaa gaactctcaa aggagatcaa aaggctgaaa   780
ggtttgctca cccagcacgg catcccctac acgaggccca cagaaacttc caacttggag   840
cacttgggcc acgagacgcc cagagccaag tctccagagc agctgcgggg tgacccagga   900
ctgcgtggga gtttgtga                                                 918
```

```
<210> SEQ ID NO 30
<211> LENGTH: 305
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Met Ala Ala Gly Leu Ala Arg Leu Leu Leu Leu Gly Leu Ser Ala
1               5                   10                  15

Gly Gly Pro Ala Pro Ala Gly Ala Ala Lys Met Lys Val Val Glu Glu
                20                  25                  30

Pro Asn Ala Phe Gly Val Asn Asn Pro Phe Leu Pro Gln Ala Ser Arg
            35                  40                  45

Leu Gln Ala Lys Arg Asp Pro Ser Pro Val Ser Gly Pro Val His Leu
        50                  55                  60

Phe Arg Leu Ser Gly Lys Cys Phe Ser Leu Val Glu Ser Thr Tyr Lys
65                  70                  75                  80

Tyr Glu Phe Cys Pro Phe His Asn Val Thr Gln His Glu Gln Thr Phe
                85                  90                  95

Arg Trp Asn Ala Tyr Ser Gly Ile Leu Gly Ile Trp His Glu Trp Glu
            100                 105                 110

Ile Ala Asn Asn Thr Phe Thr Gly Met Trp Met Arg Asp Gly Asp Ala
        115                 120                 125

Cys Arg Ser Arg Ser Arg Gln Ser Lys Val Glu Leu Ala Cys Gly Lys
    130                 135                 140

Ser Asn Arg Leu Ala His Val Ser Glu Pro Ser Thr Cys Val Tyr Ala
145                 150                 155                 160

Leu Thr Phe Glu Thr Pro Leu Val Cys His Pro His Ala Leu Leu Val
                165                 170                 175

Tyr Pro Thr Leu Pro Glu Ala Leu Gln Arg Gln Trp Asp Gln Val Glu
            180                 185                 190

Gln Asp Leu Ala Asp Glu Leu Ile Thr Pro Gln Gly His Glu Lys Leu
        195                 200                 205

Leu Arg Thr Leu Phe Glu Asp Ala Gly Tyr Leu Lys Thr Pro Glu Glu
    210                 215                 220

Asn Glu Pro Thr Gln Leu Glu Gly Gly Pro Asp Ser Leu Gly Phe Glu
225                 230                 235                 240

Thr Leu Glu Asn Cys Arg Lys Ala His Lys Glu Leu Ser Lys Glu Ile
                245                 250                 255

Lys Arg Leu Lys Gly Leu Leu Thr Gln His Gly Ile Pro Tyr Thr Arg
            260                 265                 270
```

```
Pro Thr Glu Thr Ser Asn Leu Glu His Leu Gly His Glu Thr Pro Arg
        275                 280                 285

Ala Lys Ser Pro Glu Gln Leu Arg Gly Asp Pro Gly Leu Arg Gly Ser
    290                 295                 300

Leu
305
```

MANNOSE-6-PHOSPHATE BEARING PEPTIDES FUSED TO LYSOSOMAL ENZYMES

CROSS-REFERENCE TO RELATED APPLICATIONS

This application is a 35 U.S.C. § 371 National Stage Application of International Application No. PCT/US2015/044713, filed Aug. 11, 2015, which claims priority to U.S. Provisional Application 62/036,082 filed on Aug. 11, 2014, the disclosure of which is hereby incorporated by reference in its entirety.

BACKGROUND

More than forty lysosomal storage diseases are caused, directly or indirectly, by the absence or deficiency of one or more lysosomal enzymes. Sanfilippo syndrome, or mucopolysaccharidosis III (MPS III), is one such disease. It is a rare genetic disorder characterized by the deficiency of enzymes involved in the degradation of glycosaminoglycans (GAG).

Four distinct forms of MPS III, designated MPS IIIA, B, C, and D, have been identified. Each is characterized by the absence or deficiency of a different lysosomal enzyme. Mucopolysaccharidosis type IIIB (MPS IIIB; Sanfilippo B disease) is an autosomal recessive disorder that is caused by a deficiency of the enzyme alpha-N-acetyl-glucosaminidase (Naglu), resulting in the accumulation of heparan sulfate in lysosomes of particularly neurons and glial cells in the brain, with additional lysosomal accumulation of heparan sulfate elsewhere. MPS IIIB manifests itself primarily in the brain.

Enzyme replacement therapy (ERT) has been used to deliver enzymes for the treatment of various lysosomal storage diseases. Normally, lysosomal enzymes are synthesized in the cytosol and then traverse the endoplasmic reticulum (ER), where they are glycosylated with N-linked, high mannose type carbohydrates. In the Golgi apparatus, high mannose carbohydrates on glycoproteins are then modified by a series of glycotransferases to become mature N-glycan; one of the modifications is the addition of mannose-6-phosphate (M6P). Proteins carrying this modification are then targeted to the lysosome via binding of the M6P moiety to the cation-independent mannose-6-phosphate receptor (CI-MPR). Efficacy of enzyme replacement therapy is critically dependent on proper lysosomal targeting of the replacement enzyme. However, recombinantly produced Naglu protein is characterized by a dramatic lack of M6P phosphorylation, making lysosomal targeting of this enzyme and its effective use for ERT very difficult.

Therefore, there remains a need to develop alternative methods for lysosomal targeting to ensure effective enzyme replacement therapy.

SUMMARY

The present invention provides a targeted therapeutic including a lysosomal enzyme and a lysosomal targeting moiety, wherein the lysosomal targeting moiety is a peptide containing at least one N-linked glycosylation site.

In some embodiments, the peptide contains N-linked glycosylation. In some embodiments, the peptide contains N-linked glycosylation containing a M6P group.

In some embodiments, the lysosomal enzyme is selected from Table 2. In some embodiments, lysosomal enzyme is an N-Acetylglucosaminidase (Naglu) protein. In some embodiments, the Naglu protein includes an amino acid sequence at least 80%, 90% or 95% identical to SEQ ID NO.: 1. In some embodiments, the Naglu protein includes an amino acid sequence identical to SEQ ID NO.: 1.

In some embodiments, the lysosomal targeting moiety is a peptide selected from the group consisting of prosaposin, leukemia inhibitory factor, cellular repressor of E1A-stimulate genes, and fragments thereof. In some embodiments, the peptide includes a sequence at least 80%, 90% or 95% identical to SEQ ID NO. 4, 6, or 9. In some embodiments, the peptide includes a sequence identical to SEQ ID NO. 4, 6, or 9.

In some embodiments, the targeted therapeutic is a fusion protein. In some embodiments, the lysosomal targeting moiety is fused to the N-terminus of the lysosomal enzyme. In some embodiments, the lysosomal targeting moiety is fused to the C-terminus of the lysosomal enzyme. In some embodiments, the lysosomal targeting moiety and the lysosomal enzyme is fused via a linker. In some embodiments, the linker comprises a sequence of GAPGGGGGAAAAAGGGGGGAPGGGGGAAAAAGG GGGGAPGGGGGAAAAAGGGGG GAP (SEQ ID NO.: 15). In some embodiments, the fusion protein is at least 80% or 95% identical to the amino acid sequence of SEQ ID NO. 18, 19 or 20. In some embodiments, the fusion protein is identical to the amino acid sequence of SEQ ID NO. 18, 19 or 20.

In some embodiments, the targeted therapeutic is a fusion protein. In some embodiments, the lysosomal targeting moiety is fused to the N-terminus of the lysosomal enzyme. In some embodiments, the lysosomal targeting moiety is fused to the C-terminus of the lysosomal enzyme. In some embodiments, the lysosomal targeting moiety and the lysosomal enzyme are fused via a linker. In some embodiments, the linker comprises a sequence of GAPGGGGGAAAAAGGGGGGAPGGGGGAAAAAGG GGGGAPGGGGGAAAAAGGGGG GAP (SEQ ID NO.: 15). In some embodiments, the fusion protein is at least 80% or 95% identical to the amino acid sequence of SEQ ID NO. 23, 24 or 25. In some embodiments, the fusion protein is identical to the amino acid sequence of SEQ ID NO. 23, 24 or 25.

In one aspect, the present invention provides a nucleic acid encoding any of the fusion proteins disclosed herein. In one aspect, the present invention provides a vector including any one of the nucleic acids disclosed herein, and a host cell including said vector. In some embodiments, the host cell is selected from a bacterial, yeast, insect, mammalian, or human cell. In some embodiments, the cell is a CHO cell line.

In some embodiments, the host cell co-expresses N-acetylglucosamine-1-phosphoTransferase (GNPT). In some embodiments, the host cell includes an exogenous nucleic acid encoding GNPT. In some embodiments, the host cell has activated expression of endogenous GNPT.

In one aspect, the present invention provides a method for producing a targeted therapeutic fusion protein, comprising culturing cells comprising a nucleic acid encoding a fusion protein described herein, wherein the cells co-express N-acetylglucosamine-1-phosphoTransferase (GNPT), and recovering the fusion protein produced by the cells.

In one aspect, the present invention provides a pharmaceutical composition including any of the targeted therapeutics described herein, and a pharmaceutical acceptable carrier. In one aspect, the present invention provides a method of treating a lysosomal storage disease by administering to a subject in need of treatment any of the pharmaceutical compositions described herein. In some embodiments, the lysosomal storage disease is Sanfilippo syndrome type B. In some embodiments, the pharmaceutical composition is administered intravenously, subcutaneously, intrathecally and/or combinations thereof.

BRIEF DESCRIPTION OF THE FIGURES

FIG. 9 shows quantification of M6P monosaccharide derived from Naglu-SapDC and Naglu-LIF by PAD-HPLC. M6P content of I2S was used as a control.

DEFINITIONS

Figure 1:
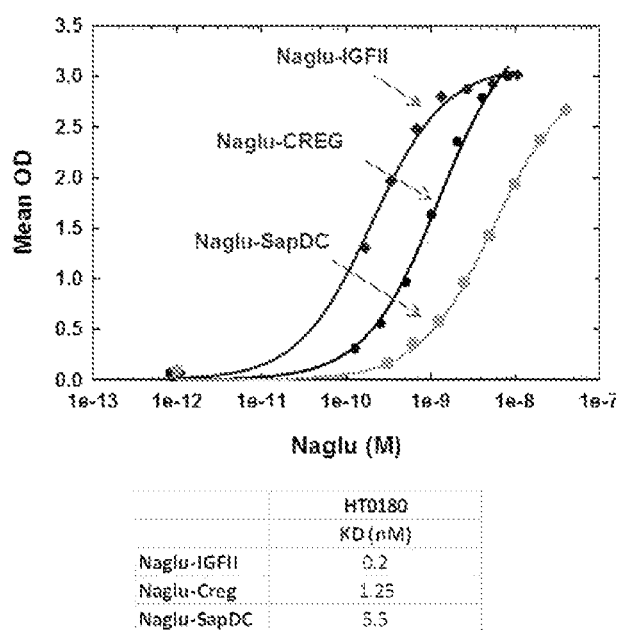
FIG. 1 shows an M6P receptor in vitro binding assay for Naglu-IGFII, Naglu-CREG and Naglu-SapDC fusion proteins.

In order for the present invention to be more readily understood, certain terms are first defined below. Additional definitions for the following terms and other terms are set forth throughout the specification.

Alpha-N-acetyl-glucosaminidase: As used herein, the term "alpha-N-acetyl-glucosaminidase" refers to enzymes capable of hydrolyzing terminal non-reducing N-acetyl-D-glucosamine residues in N-acetyl-alpha-D-glucosaminides. Alpha-N-acetyl-glucosaminidase is also known as alpha-acetyl-glucosaminidase, N-acetyl-alpha-D-glucosaminidase, N-acetyl-alpha-glucosaminidase and alpha-D-2-acetamido-2-deoxyglucosidase.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Amelioration: As used herein, the term "amelioration" is meant the prevention, reduction or palliation of a state, or improvement of the state of a subject. Amelioration includes, but does not require complete recovery or complete prevention of a disease condition. In some embodiments, amelioration includes increasing levels of relevant protein or its activity that is deficient in relevant disease tissues.

Amino acid: As used herein, term "amino acid," in its broadest sense, refers to any compound and/or substance that can be incorporated into a polypeptide chain. In some embodiments, an amino acid has the general structure $H_2N$—$C(H)(R)$—$COOH$. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Biologically active: As used herein, the phrase "biologically active" (or biological activity) refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Cation-independent mannose-6-phosphate receptor (CI-M6PR): As used herein, the term "cation-independent mannose-6-phosphate receptor (CI-M6PR)" refers to a cellular receptor that binds mannose-6-phosphate (M6P) tags on acid hydrolase (e.g., alpha-N-acetyl-glucosaminidase) precursors in the Golgi apparatus that are destined for transport to the lysosome. In addition to mannose-6-phosphates, the CI-M6PR also binds certain proteins, including IGF-II. The CI-M6PR is also known as "CI-MPR", "M6P/IGF-II receptor", "CI-MPR/IGF-II receptor", "CD222", "MPR300", "IGF-II receptor" or "IGF2 Receptor." These terms and abbreviations thereof are used interchangeably herein.

Diluent: As used herein, the term "diluent" refers to a pharmaceutically acceptable (e.g., safe and non-toxic for administration to a human) diluting substance useful for the preparation of a reconstituted formulation. Exemplary diluents include sterile water, bacteriostatic water for injection (BWFI), a pH buffered solution (e.g. phosphate-buffered saline), sterile saline solution, Ringer's solution or dextrose solution.

Enzyme replacement therapy (ERT): As used herein, the term "enzyme replacement therapy (ERT)" refers to any therapeutic strategy that corrects an enzyme deficiency by providing the missing enzyme. In some embodiments, the missing enzyme is provided by intrathecal administration. In some embodiments, the missing enzyme is provided by infusing into bloodsteam. Once administered, enzyme is taken up by cells and transported to the lysosome, where the enzyme acts to eliminate material that has accumulated in the lysosomes due to the enzyme deficiency. Typically, for lysosomal enzyme replacement therapy to be effective, the therapeutic enzyme is delivered to lysosomes in the appropriate cells in target tissues where the storage defect is manifest.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein. In this application, the terms "expression" and "production," and grammatical equivalents, are used inter-changeably.

Glycan: As is known in the art and used herein "glycans" are sugars. Glycans can be monomers or polymers of sugar residues, but typically contain at least three sugars, and can be linear or branched. A glycan may include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6'sulfo N-acetylglucosamine, etc). The term "glycan" includes homo and heteropolymers of sugar residues. The term "glycan" also encompasses a glycan component of a glycoconjugate (e.g., of a glycoprotein, glycolipid, proteoglycan, etc.). The term also encompasses free glycans, including glycans that have been cleaved or otherwise released from a glycoconjugate.

Glycoconjugate: The term "glycoconjugate", as used herein, encompasses all molecules in which at least one sugar moiety is covalently linked to at least one other moiety. The term specifically encompasses all biomolecules with covalently attached sugar moieties, including for example N-linked glycoproteins, O-linked glycoproteins, glycolipids, proteoglycans, etc.

Glycoprotein: As used herein, the term "glycoprotein" refers to a protein that contains a peptide backbone covalently linked to one or more sugar moieties (i.e., glycans). As is understood by those skilled in the art, the peptide backbone typically comprises a linear chain of amino acid residues. In certain embodiments, the peptide backbone spans the cell membrane, such that it comprises a transmembrane portion, as well as an extracellular portion and/or an intracellular portion. In certain embodiments, a peptide backbone of a glycoprotein that spans the cell membrane comprises an intracellular portion, a transmembrane portion, and an extracellular portion. The sugar moiety(ies) may be in the form of monosaccharides, disaccharides, oligosaccharides, and/or polysaccharides. The sugar moiety(ies) may comprise a single unbranched chain of sugar residues or may comprise one or more branched chains. In certain embodiments, sugar moieties may include sulfate and/or phosphate groups. Alternatively or additionally, sugar moieties may include acetyl, glycolyl, propyl or other alkyl modifications. Alternatively or additionally, sugar moieties may be modified by diacetylation. In certain embodiments, glycoproteins contain O-linked sugar moieties; in certain embodiments, glycoproteins contain N-linked sugar moieties. In certain embodiments, the sugar moiety is specifically a N-linked glycan containing a mannose-6-phosphate residue. In certain embodiments, methods disclosed herein comprise a step of analyzing therapeutic glycoproteins, liberated fragments (e.g., glycopeptides) of cell surface glycoproteins, cell surface glycans attached to cell surface glycoproteins, peptide backbones of cell surface glycoproteins, fragments of such glycoproteins, glycans and/or peptide backbones, and combinations thereof for their glycosylation pattern and/or level of M6P phoshorylation.

High mannose: As used herein, the term "high mannose" is used herein to describe proteins (e.g., Naglu) containing one or more Man9(GlcNAc)2, Man8(GlcNAc)2, Man7(GlcNAc)2, Man6(GlcNAc)2, and/or Man5(GlcNAc)2 N-linked oligosaccharides, or combinations thereof.

Homology: As used herein, the term "homology" (or the corresponding adjective "homogous") refers to the overall relatedness of polymeric molecules, e.g., of nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Identity: As used herein, the term "identity" refers to the overall relatedness of polymeric molecules, e.g., of nucleic acid molecules (e.g., DNA molecules and/or RNA molecules) and/or of polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Intrathecal administration: As used herein, the term "intrathecal administration" or "intrathecal injection" refers to an injection into the spinal canal (intrathecal space surrounding the spinal cord). Various techniques may be used including, without limitation, lateral cerebroventricular injection through a burrhole or cisternal or lumbar puncture or the like. In some embodiments, "intrathecal administration" or "intrathecal delivery" according to the present invention refers to IT administration or delivery via the lumbar area or region, i.e., lumbar IT administration or delivery. As used herein, the term "lumbar region" or "lumbar area" refers to the area between the third and fourth lumbar (lower back) vertebrae and, more inclusively, the L2-S1 region of the spine.

Linker: As used herein, the term "linker" refers to, in a fusion protein, an amino acid sequence other than that appearing at a particular position in the natural protein and is generally designed to be flexible or to interpose a structure, such as an a-helix, between two protein moieties. A linker is also referred to as a spacer.

Lysosomal enzyme: As used herein, the term "lysosomal enzyme" refers to any enzyme that is capable of reducing accumulated materials in mammalian lysosomes or that can rescue or ameliorate one or more lysosomal storage disease symptoms. Lysosomal enzymes suitable for the invention include both wild-type or modified lysosomal enzymes and can be produced using recombinant and synthetic methods or purified from nature sources. Exemplary lysosomal enzymes are listed in Table 1.

Lysosomal enzyme deficiency: As used herein, "lysosomal enzyme deficiency" refers to a group of genetic disorders that result from deficiency in at least one of the enzymes that are required to break macromolecules (e.g., enzyme substrates) down to peptides, amino acids, monosaccharides, nucleic acids and fatty acids in lysosomes. As a result, individuals suffering from lysosomal enzyme deficiencies have accumulated materials in various tissues (e.g., CNS, liver, spleen, gut, blood vessel walls and other organs).

Lysosomal Storage Disease: As used herein, the term "lysosomal storage disease" refers to any disease resulting from the deficiency of one or more lysosomal enzymes necessary for metabolizing natural macromolecules. These diseases typically result in the accumulation of un-degraded molecules in the lysosomes, resulting in increased numbers of storage granules (also termed storage vesicles).

messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions.

Moiety: As used herein, the term "moiety" refers to a part or functional group of a molecule (e.g., a glycan or a protein). The "moiety" is used interchangeably with the term "residue" herein.

N-acetylglucosamine-1-phosphotransferase (GNPT) protein: As used herein, the term N-acetylglucosamine-1-phosphotransferase (GNPT) protein refers to enzymes capable of catalyzing the transfer of N-acetylglucosamine-1-phosphate from UDP-GlcNAc to mannose residues on lysosomal hydrolases (e.g., alpha-N-acetyl-glucosaminidase).

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre and post natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Protein: As used herein, the term "protein" of "therapeutic protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain l-amino acids, d-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Recombinant: As used herein, the term "recombinant" refers to DNA molecules, peptides, proteins or cells that are generated using recombinant DNA technology, as the term is commonly understood by the person gaving ordinary skill in the art.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to a an amount greater than 80%, 85%, 90%, 95%, 96%, 97%, 98%, 99% of the total amount.

Target tissues: As used herein, the term "target tissues" refers to any tissue that is affected by the lysosomal storage disease to be treated or any tissue in which the deficient lysosomal enzyme is normally expressed. In some embodiments, target tissues include those tissues in which there is a detectable or abnormally high amount of enzyme substrate, for example stored in the cellular lysosomes of the tissue, in patients suffering from or susceptible to the lysosomal storage disease. In some embodiments, target tissues include those tissues that display disease-associated pathology, symptom, or feature. In some embodiments, target tissues include those tissues in which the deficient lysosomal enzyme is normally expressed at an elevated level. As used herein, a target tissue may be a brain target tissue, a spinal cord target tissue and/or a peripheral target tissue. Exemplary target tissues are described in detail below.

Therapeutic Glycoprotein: As used herein, the term "Therapeutic Glycoprotein" refers to any glycoprotein that can act to replace at least in part the deficient or missing enzyme in a disease to be treated. In some embodiments, the term therapeutic glycoprotein, refers to lysosomal proteins (e.g., acid hydrolase) which may be localized, transported, processed and/or resides in the lysosome of the cell. In some embodiments, a therapeutic glycoprotein refers to a glycoprotein with enzyme activity (e.g., lysosomal enzyme) which can act to replace at least in part the deficient or missing lysosomal enzyme in a lysosomal storage disease to be treated. In some embodiments, a therapeutic glycoprotein is capable of reducing accumulated materials in mammalian lysosomes or that can rescue or ameliorate one or more lysosomal storage disease symptoms. Therapeutic glycoproteins suitable for the invention include both wild-type, modified or protein fusion of a lysosomal enzymes and can be produced using recombinant methods.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treatment: As used herein, the term "treatment" (also "treat" or "treating") refers to any administration of a therapeutic (e.g., lysosomal enzyme) that partially or completely alleviates, ameliorates, relieves, inhibits, delays onset of, reduces severity of and/or reduces incidence of one or more symptoms or features of a particular disease, disorder, and/or condition (e.g., Hunters syndrome, Sanfilippo B syndrome). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

DETAILED DESCRIPTION

The present invention provides targeted therapeutics containing a lysosomal enzyme and a lysosomal targeting moiety containing a N-linked glycosylation site, as well as methods of making the same and using the same for effective enzyme replacement therapy of lysosomal storage diseases.

In some embodiments, the present invention provides a lysosomal targeting moiety that is a peptide containing N-linked glycosylation containing a M6P group. In some embodiments, the present invention provides a targeted therapeutic wherein the lysosomal enzyme and the lysosomal targeting moiety are fused via a linker. In some embodiments, the present invention provides vectors including a nucleic acid encoding a targeted therapeutic, as well as host cells containing the same and co-expressing GNPT. In some embodiments, the lysosomal enzyme is Naglu.

Various aspects of the invention are described in further detail in the following subsections. The use of subsections is not meant to limit the invention. Each subsection may apply to any aspect of the invention. In this application, the use of "or" means "and/or" unless stated otherwise.

Therapeutic Lysosomal Enzymes—Naglu Protein

The present inventors discovered unexpectedly that lysosomal enzymes could be targeted to the lysosome by connecting them to a targeting moiety containing a N-linked glycosylation site. The present invention provides targeted therapeutics containing a lysosomal enzyme and a lysosomal targeting moiety containing a N-linked glycosylation site. In some embodiments, a suitable therapeutic lysosomal enzyme in the context of the present invention is recombinant human Naglu protein. Alpha-N-acetyl-glucosaminidase (Naglu) aids in the stepwise degradation of the heparan sulfate in lysosomes by removing GlcNAc (N-acetyl-glucosamine) from the non-reducing end of this glycosaminoglycan. A lack of Naglu leads to incomplete breakdown of heparan sulfate and the subsequent accumulation in lysosomes of the incomplete breakdown products. The absence of Naglu causes the fatal neurodegenerative disease Sanfilippo Type III B.

A suitable Naglu protein according to the present invention can be any molecule that can substitute for naturally-occurring Naglu protein activity or rescue one or more phenotypes or symptoms associated with Naglu-deficiency. In some embodiments, a Naglu protein suitable for the invention is a polypeptide having an N-terminus and a C-terminus and an amino acid sequence substantially similar or identical to the mature human Naglu protein.

Typically, human Naglu is produced as a precursor molecule that is processed to a mature form. This process generally occurs by removing the 23 amino acid signal peptide as the protein enters the endoplasmic reticulum. Typically, the precursor form is also referred to as full-length precursor or full-length Naglu protein, which contains 743 amino acids. The N-terminal 23 amino acids are cleaved as the precursor protein enters the endoplasmic reticulum, resulting in a mature form. Thus, it is contemplated that the N-terminal 23 amino acids are generally not required for Naglu protein activity. However, the use of the full-length precursor of the Naglu protein is also contemplated within the scope of the instant invention. The amino acid sequences of the mature form (SEQ ID NO:1) and full-length precursor (SEQ ID NO:2) of a typical wild-type or naturally-occurring human Naglu protein are shown in Table 1 below.

TABLE 1

| Mature and Full-length Precursor Naglu Protein | |
|---|---|
| Mature Form of Naglu | DEAREAAAVRALVARLLGPGPAADFSVSVERALAAKPGLDTYSLGGGGAARVRV RGSTGVAAAAGLHRYLRDFCGCHVAWSGSQLRLPRPLPAVPGELTEATPNRYRY YQNVCTQSYSFVWWDWARWEREIDWMALNGINLALAWSGQEAIWQRVYLALGLT QAEINEFFTGPAFLAWGRMGNLHTWDGPLPPSWHIKQLYLQHRVLDQMRSFGMT PVLPAFAGHVPEAVTRVFPQVNVTKMGSWGHFNCSYSCSFLLAPEDPIFPIIGS LFLRELIKEFGTDHIYGADTFNEMQPPSSEPSYLAAATTAVYEAMTAVDTEAVW LLQGWLFQHQPQFWGPAQIRAVLGAVPRGRLLVLDLFAESQPVYTRTASFQGQP FIWCMLHNFGGNHGLFGALEAVNGGPEAARLFPNSTMVGTGMAPEGISQNEVVY SLMAELGWRKDPVPDLAAWVTSFAARRYGVSHPDAGAAWRLLLRSVYNCSGEAC RGHNRSPLVRRPSLQMNTSIWYNRSDVFEAWRLLLTSAPSLATSPAFRYDLLDL TRQAVQELVSLYYEEARSAYLSKELASLLRAGGVLAYELLPALDEVLASDSRFL LGSWLEQARAAAVSEAEADFYEQNSRYQLTLWGPEGNILDYANKQLAGLVANYY TPRWRLFLEALVDSVAQGIPFQQHQFDKNVFQLEQAFVLSKQRYPSQPRGDTVD LAKKIFLKYYPRWVAGSW (SEQ ID NO.: 1) |
| Full-Length Precursor/Full-Length Naglu Protein | MEAVAVAAAVGVLLLAGAGGAAGDEAREAAAVRALVARLLGPGPAADFSVSVER ALAAKPGLDTYSLGGGGAARVRVRGSTGVAAAAGLHRYLRDFCGCHVAWSGSQL RLPRPLPAVPGELTEATPNRYRYYQNVCTQSYSFVWWDWARWEREIDWMALNGI NLALAWSGQEAIWQRVYLALGLTQAEINEFFTGPAFLAWGRMGNLHTWDGPLPP SWHIKQLYLQHRVLDQMRSFGMTPVLPAFAGHVPEAVTRVFPQVNVTKMGSWGH FNCSYSCSFLLAPEDPIFPIIGSLFLRELIKEFGTDHIYGADTFNEMQPPSSEP SYLAAATTAVYEAMTAVDTEAVWLLQGWLFQHQPQFWGPAQIRAVLGAVPRGRL LVLDLFAESQPVYTRTASFQGQPFIWCMLHNFGGNHGLFGALEAVNGGPEAARL FPNSTMVGTGMAPEGISQNEVVYSLMAELGWRKDPVPDLAAWVTSFAARRYGVS HPDAGAAWRLLLRSVYNCSGEACRGHNRSPLVRRPSLQMNTSIWYNRSDVFEAW RLLLTSAPSLATSPAFRYDLLDLTRQAVQELVSLYYEEARSAYLSKELASLLRA GGVLAYELLPALDEVLASDSRFLLGSWLEQARAAAVSEAEADFYEQNSRYQLTL WGPEGNILDYANKQLAGLVANYYTPRWRLFLEALVDSVAQGIPFQQHQFDKNVF QLEQAFVLSKQRYPSQPRGDTVDLAKKIFLKYYPRWVAGSW (SEQ ID NO.: 2) |

Thus, in some embodiments, Naglu protein suitable for the present invention is mature human Naglu protein (SEQ ID NO:1). In some embodiments, a suitable Naglu protein may be a homologue or an orthologue of the mature human Naglu protein from a different species (e.g., mouse, rat, sheep, pig, dog, etc.). In other embodiments, a suitable Naglu protein may be a functional variant of the mature human Naglu protein. A functional variant of the mature human Naglu protein may be a modified mature human Naglu protein containing one or more amino acid substitutions, deletions, and/or insertions as compared to a wild-type or naturally-occurring Naglu protein (e.g., SEQ ID NO:1), while substantially retaining the biological activity of Naglu protein. Thus, in some embodiments, a Naglu protein suitable for the present invention is substantially homologous to mature human Naglu protein (SEQ ID NO:1). In some embodiments, a Naglu protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1. In some embodiments, a Naglu protein suitable for the present invention is substantially identical to mature human Naglu protein (SEQ ID NO:1). In some embodiments, a Naglu protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1. In some embodiments, a Naglu protein suitable for the present invention contains a fragment or a portion of mature human Naglu protein.

Alternatively, a Naglu protein suitable for the present invention is full-length Naglu protein. In some embodiments, a Naglu protein suitable may be a homologue or an orthologue of full-length human Naglu protein from a different species (e.g. mouse, rat, sheep, pig, dog, etc.). In some embodiments, a suitable Naglu protein may be a functional variant of the full-length human Naglu protein containing one or more amino acid substitutions, deletions, and/or insertions as compared to a wild-type or naturally-occurring full-length Naglu protein (e.g., SEQ ID NO:2), while retaining substantial Naglu protein activity. Thus, In some embodiments, Naglu protein suitable for the present invention is substantially homologous to full-length human Naglu protein (SEQ ID NO:2). In some embodiments, a Naglu protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:2. In some embodiments, a Naglu protein suitable for the present invention is substantially identical to SEQ ID NO:2. In some embodiments, a Naglu protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:2. In some embodiments, a Naglu protein suitable for the present invention contains a fragment or a portion of full-length human Naglu protein. As used herein, a full-length Naglu protein typically contains signal peptide sequence.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids* Res. 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999; all of the foregoing of which are incorporated herein by reference. In addition to identifying homologous sequences, the programs mentioned above typically provide an indication of the degree of homology. In some embodiments, two sequences are considered to be substantially homologous if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are homologous over a relevant stretch of residues. In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues.

The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., Nucleic Acids Res. 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Alternative Therapeutic Lysosomal Enzymes

The present inventors discovered unexpectedly that lysosomal enzymes could be targeted to the lysosome by connecting them to a targeting moiety containing a N-linked glycosylation site. Thus, the present invention provides targeted therapeutics containing a lysosomal enzyme and a lysosomal targeting moiety containing a N-linked glycosylation site. A suitable therapeutic lysosomal enzyme in the context of the present invention is any protein which has been shown to play a role in the development or treatment of a lysosomal storage disease, in particular those lysosomal storage diseases having CNS etiology and/or symptoms, including, but not limited to, aspartylglucosaminuria, cholesterol ester storage disease, Wolman disease, cystinosis, Danon disease, Fabry disease, Farber lipogranulomatosis, Farber disease, fucosidosis, galactosialidosis types I/II, Gaucher disease types I/II/III, globoid cell leukodystrophy, Krabbe disease, glycogen storage disease II, Pompe disease, GM1-gangliosidosis types I/II/III, GM2-gangliosidosis type I, Tay Sachs disease, GM2-gangliosidosis type II, Sandhoff disease, GM2-gangliosidosis, α-mannosidosis types I/II, .beta.-mannosidosis, metachromatic leukodystrophy, mucolipidosis type I, sialidosis types I/II, mucolipidosis types II/III, I-cell disease, mucolipidosis type IIIC pseudo-Hurler polydystrophy, mucopolysaccharidosis type I, mucopolysaccharidosis type II, mucopolysaccharidosis type IIIA, Sanfilippo syndrome, mucopolysaccharidosis type IIIB, mucopolysaccharidosis type IIIC, mucopolysaccharidosis type HID, mucopolysaccharidosis type IVA, Morquio syndrome, mucopolysaccharidosis type IVB, mucopolysaccharidosis type VI, mucopolysaccharidosis type VII, Sly syndrome, mucopolysaccharidosis type IX, multiple sulfatase deficiency, neuronal ceroid lipofuscinosis, CLN1 Batten disease, CLN2 Batten diseae, Niemann-Pick disease types A/B, Niemann-Pick disease type C1, Niemann-Pick disease type C2, pycnodysostosis, Schindler disease types I/II, Gaucher disease and sialic acid storage disease.

A detailed review of the genetic etiology, clinical manifestations, and molecular biology of lysosomal storage diseases are detailed in Scriver et al., eds., The Metabolic and Molecular Basis of Inherited Disease, 7.sup.th Ed., Vol. II, McGraw Hill, (1995). The enzymes deficient in the above diseases are generally known to those of skill in the art; some of these are exemplified in Table 2 below:

TABLE 2

Proteins Associated with Lysosomal Storage Disease

| Disease Name | Enzyme Deficiency | Substance Stored |
|---|---|---|
| Pompe Disease | Acid-a1,4-Glucosidase | Glycogen $\alpha$-1-4 linked Oligosaccharides |
| GM1 Gangliodsidosis | $\beta$-Galactosidase | $GM_1$ Gangliosides |
| Tay-Sachs Disease | $\beta$-Hexosaminidase A | $GM_2$ Ganglioside |
| GM2 Gangliosidosis: AB Variant | $GM_2$ Activator Protein | $GM_2$ Ganglioside |
| Sandhoff Disease | $\beta$-Hexosaminidase A&B | $GM_2$ Ganglioside |
| Fabry Disease | $\alpha$-Galactosidase A | Globosides |
| Gaucher Disease | Glucocerebrosidase | Glucosylceramide |
| Metachromatic Leukodystrophy | Arylsulfatase A | Sulphatides |
| Krabbe Disease | Galactosylceramidase | Galactocerebroside |
| Niemann Pick, Types A & B | Acid Sphingomyelinase | Sphingomyelin |
| Niemann-Pick, Type C | Cholesterol Esterification Defect | Sphingomyelin |
| Niemann-Pick, Type D | Unknown | Sphingomyelin |
| Farber Disease | Acid Ceramidase | Ceramide |
| Wolman Disease | Acid Lipase | Cholesteryl Esters |
| Hurler Syndrome (MPS IH) | $\alpha$-L-Iduronidase | Heparan & Dermatan Sulfates |
| Scheie Syndrome (MPS IS) | $\alpha$-L-Iduronidase | Heparan & Dermatan, Sulfates |
| Hurler-Scheie (MPS IH/S) | $\alpha$-L-Iduronidase | Heparan & Dermatan Sulfates |
| Hunter Syndrome (MPS II) | Iduronate Sulfatase | Heparan & Dermatan Sulfates |
| Sanfilippo A (MPS IIIA) | Heparan N-Sulfatase | Heparan Sulfate |
| Sanfilippo B (MPS IIIB) | $\alpha$-N-Acetylglucosaminidase | Heparan Sulfate |
| Sanfilippo C (MPS IIIC) | Acetyl-CoA-Glucosaminide Acetyltransferase | Heparan Sulfate |
| Sanfilippo D (MPS IIID) | N-Acetylglucosamine-6-Sulfatase | Heparan Sulfate |
| Morquio B (MPS IVB) | $\beta$-Galactosidase | Keratan Sulfate |
| Maroteaux-Lamy (MPS VI) | Arylsulfatase B | Dermatan Sulfate |
| Sly Syndrome (MPS VII) | $\beta$-Glucuronidase | |
| $\alpha$-Mannosidosis | $\alpha$-Mannosidase | Mannose/Oligosaccharides |
| $\alpha$-Mannosidosis | $\beta$-mannosidase | Mannose/Oligosaccharides |
| Fucosidosis | $\alpha$-L-Fucosidase | Fucosyl/Oligosaccharides |
| Aspartylglucosaminuria | N-Aspartyl-$\beta$-Glucosaminidase | Aspartylglucosamine Asparagines |
| Sialidosis (Mucolipidosis I) | $\alpha$-Neuraminidase | Sialyloligosaccharides |
| Galactosialidosis (Goldberg Syndrome) | Lysosomal Protective Protein Deficiency | Sialyloligosaccharides |
| Schindler Disease | $\alpha$-N-Acetyl-Galactosaminidase | |
| Mucolipidosis II (I-Cell Disease) | N-Acetylglucosamine-1-Phosphotransferase | Heparan Sulfate |
| Mucolipidosis III (Pseudo-Hurler Polydystrophy) | Same as ML II | |
| Cystinosis | Cystine Transport Protein | Free Cystine |
| Salla Disease | Sialic Acid Transport Protein | Free Sialic Acid and Glucuronic Acid |
| Infantile Sialic Acid Storage Disease | Sialic Acid Transport Protein | Free Sialic Acid and Glucuronic Acid |
| Infantile Neuronal Ceroid Lipofuscinosis | Palmitoyl-Protein Thioesterase | Lipofuscins |
| Mucolipidosis IV | Unknown | Gangliosides & Hyaluronic Acid |
| Prosaposin | Saposins A, B, C or D | |

In some embodiments, a therapeutic lysosomal enzyme suitable for the present invention is the human wildtype protein. In some embodiments, a therapeutic lysosomal enzyme may be a homologue or an orthologue of the human wildtype protein from a different species (e.g., mouse, rat, sheep, pig, dog, etc.). In other embodiments, a therapeutic lysosomal enzyme suitable for the present invention may be a functional variant of the human wildtype protein. A functional variant of the human wildtype protein may be a modified human wildtype protein containing one or more amino acid substitutions, deletions, and/or insertions as compared to a wild-type or naturally-occurring protein, while substantially retaining the biological activity of the human wildtype protein. Thus, in some embodiments, a therapeutic lysosomal enzyme suitable for the present invention is substantially homologous to the human wildtype protein. In some embodiments, a therapeutic lysosomal enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to the human wildtype protein. In some embodiments, a therapeutic lysosomal enzyme suitable for the present invention is substantially identical to the human wildtype protein. In some embodiments, a therapeutic lysosomal enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to the human wildtype protein. In some embodiments, a therapeutic lysosomal enzyme suitable for the present invention contains a fragment or a portion of the human wildtype protein.

Lysosomal Targeting Moiety

The present inventors discovered unexpectedly that lysosomal enzymes could be targeted to the lysosome by connecting them to a targeting moiety containing a N-linked glycosylation site. Thus, the present invention provides targeted therapeutics containing a lysosomal enzyme and a lysosomal targeting moiety containing a N-linked glycosylation site.

The present invention contemplates that any peptide may be used within the scope of the present invention as long as it has a N-linked glycosylation site. N-linked glycosylation sites may be predicted by computer algorithms and software, many of which are generally known in the art. Alternatively, N-linked glycosylation may be determined experimentally using any one of the many assays generally known in the art. Non-limiting examples of such assays are provided in the Examples section herein.

Suitable targeting moieties may be derived from proteins or peptides including, but not limited to, IGF-I, Kif, ApoE, TAT, RAP, p97, Plasminogen, Leukemia Inhibitory Factor Peptide (LIF), Cellular Repressor of E1A-Stimulated Genes Peptide (CREG), Human Sortlin-1 Propeptide (SPP), Human Prosaposin peptide (SapDC) and Progranulin. In some embodiments, a lysosomal targeting moiety is any protein, peptide, or fragment thereof that binds the CI-M6PR, in a mannose-6-phosphate-dependent manner. In some embodiments, a lysosomal targeting moiety is any protein, peptide, or fragment thereof that binds directly to a region, domain and/or extracellular portion of CI-M6PR. In some embodiments, a lysosomal targeting moiety is any protein, peptide, or fragment thereof that binds directly to a region, domain and/or extracellular portion of CI-M6PR via a M6P residue.

In some embodiments, a lysosomal targeting moiety is derived from human Prosaposin (SEQ ID NO:3). In some embodiments, the lysosomal targeting moiety is a Prosaposin sequence of a wild-type or naturally-occurring human Prosaposin protein. In some embodiments, an amino acid sequence comprising the C terminal region and D functional domain of Prosaposin is used (SEQ ID NO:4)

TABLE 3

Human Prosaposin

| | |
|---|---|
| Human Prosaposin | MYALFLLASLLGAALAGPVLGLKECTRGSAVWCQNVKTASDCGAVKHCLQTVWN KPTVKSLPCDICKDVVTAAGDMLKDNATEEEILVYLEKTCDWLPKPNMSASCKE IVDSYLPVILDIIKGEMSRPGEVCSALNLCESLQKHLAELNHQKQLESNKIPEL DMTEVVAPFMANIPLLLYPQDGPRSKPQPKDNGDVCQDCIQMVTDIQTAVRTNS TFVQALVEHVKEECDRLGPGMADICKNYISQYSEIAIQMMMHMQPKEICALVGF CDEVKEMPMQTLVPAKVASKNVIPALELVEPIKKHEVPAKSDVYCEVCEFLVKE VTKLIDNNKTEKEILDAFDKMCSKLPKSLSEECQEVVDTYGSSILSILLEEVSP ELVCSMLHLCSGTRLPALTVHVTQPKDGGFCEVCKKLVGYLDRNLEKNSTKQEI LAALEKGCSFLPDPYQKQCDQFVAEYEPVLIEILVEVMDPSFVCLKIGACPSAH KPLL GTEKCIWGPSYWCQNTETAAQCNAVEHCKRHVWN (SEQ ID NO: 3) |
| Human Prosaposin Peptide (SapDC) | DGGFCEVCKKLVGYLDRNLEKNSTKQEILAALEKGCSFLPDPYQKQCDQFVAEY EPVLIEILVEVMDPSFVCLKIGACPSAHKPLLGTEKCIWGPSYWCQNTETAAQC NAVEHCKRHVWN (SEQ ID NO: 4) |

In some embodiments, a lysosomal targeting moiety is a modified human Prosaposin sequence containing amino acid substitutions, insertions or deletions. In some embodiments, a lysosomal targeting moiety has a sequence at least 50%, 55%, 60%, 65%, 70%, 75%, 80%, 85%, 90%, 95%, 98%, or 99% identical to the sequence of human Prosaposin (SEQ ID NO:3). In some embodiments, a lysosomal targeting moiety is a fragment of human Prosaposin. In some embodiments, a lysosomal targeting moiety is a modified human Prosaposin DC peptide (SapDC) sequence containing amino acid substitutions, insertions or deletions. In some embodiments, a lysosomal targeting moiety has a sequence at least 50%, 55%, 60%, 65%, 70%, 75%, 80%, 85%, 90%, 95%, 98%, or 99% identical to SapDC (SEQ ID NO:4). In some embodiments, a lysosomal targeting moiety is a fragment of SapDC. In some embodiments, a lysosomal targeting moiety contains human Prosaposin (SEQ ID NO:3) or SapDC (SEQ ID NO:4) that has one or more N-terminal, C-terminal or internal deletions. In some embodiments, a lysosomal targeting moiety is a modified human Prosaposin or SapDC peptide that has diminished binding affinity for receptors.

In some embodiments, a lysosomal targeting moiety is derived from human Leukemia inhibitory Factor (SEQ ID NO:5). In some embodiments, the lysosomal targeting moiety is a Leukemia inhibitory Factor sequence of a wild-type or naturally-occurring human Leukemia inhibitory Factor protein. In some embodiments, an amino acid sequence comprises the signal peptide, glycosylation sites, helices A, B, C and/or D of the 4 helix bundle and combinations thereof, of Leukemia Inhibitory Factor. In some embodiments, an amino acid peptide sequence comprising the signal peptide, glycosylation sites, helices A, B, C and D of the 4 helix bundle and various mutations (LIF) is used (SEQ ID NO:6).

In some embodiments, a lysosomal targeting moiety is derived from human Cellular Repressor of E1A-stimulated Genes protein (SEQ ID NO:7). In some embodiments, the lysosomal targeting moiety is a Cellular Repressor of E1A-stimulated Genes sequence of a wild-type or naturally-occurring human Cellular Repressor of E1A-stimulated

TABLE 4

Human Leukemia Inhibitory Factor

| | |
|---|---|
| Human Leukemia Inhibitory Factor | MKVLAAGVVPLLLVLHWKHGAGSPLPITPVNATCAIRHPCHNNLMNQIRSQLAQL NGSANALFILYYTAQGEPFPNNLDKLCGPNVTDFPPFHANGTEKAKLVELYRIVV YLGTSLGNITRDQKILNPSALSLHSKLNATADILRGLLSNVLCRLCSKYHVGHVD VTYGPDTSGKDVFQKKKLGCQLLGKYKQIIAVLAQAF (SEQ ID NO: 5) |
| Human Leukemia Inhibitory Factor Peptide | SPLPITPVNATCAIRHPCHNNLMN{A}IR{A}QLA{A}L(N)GSANALFILYYTA QGEPFPNNLDKLCGP(N)VTDFPPPHA(N)GTEKAKLVELYRIVVYLGTSLG(N) ITRDQKILNPSALSLHSKL(N)ATADILRGLLSNVLCRLCSKYHVGHVDVTYGPD TSGKDV[[A]]QK[[A]]KLGCQLLGKYKQIIAVLAQAF (SEQ ID NO: 6) |

Sites within LIF Sequence
  (N)—denotes glycosylation sites
  { }—denotes mutations made to alter recognition of the receptor gp130; [[ ]]—denotes mutations made to alter recognition of the receptor for Leukemia Inhibitory Factor In some embodiments, a lysosomal targeting moiety is a modified human Leukemia inhibitory Factor sequence containing amino acid substitutions, insertions or deletions. In some embodiments, a lysosomal targeting moiety has a sequence at least 50%, 55%, 60%, 65%, 70%, 75%, 80%, 85%, 90%, 95%, 98%, or 99% identical to the sequence of Leukemia inhibitory Factor (SEQ ID NO:5). In some embodiments, a lysosomal targeting moiety is a fragment of human Leukemia inhibitory Factor. In some embodiments, a lysosomal targeting moiety is a modified human LIF sequence (SEQ ID NO:6) containing amino acid substitutions, insertions or deletions. In some embodiments, a lysosomal targeting moiety has a sequence at least 50%, 55%, 60%, 65%, 70%, 75%, 80%, 85%, 90%, 95%, 98%, or 99% identical to LIF (SEQ ID NO:6). In some embodiments, a lysosomal targeting moiety is a fragment of LIF. In some embodiments, a lysosomal targeting moiety contains human Leukemia inhibitory Factor (SEQ ID NO:5) or LIF (SEQ ID NO:6) that has one or more N-terminal, C-terminal or internal deletions. In some embodiments, a lysosomal targeting moiety is a modified human Leukemia inhibitory Factor or LIF peptide that has diminished binding affinity for the LIF receptor and/or alternative binding proteins, such as but not limited to, pg 130.

Genes protein.

In some embodiments, an amino acid sequence not comprising the sequence of the signal peptide of Cellular Repressor of E1A-stimulated Genes, and not comprising the internal peptide of the sequence DPQS (SEQ ID NO:8) of Cellular Repressor of E1A-stimulated Genes is used, resulting in Human Repressor of E1-stimulated Genes Peptide (CREG) (SEQ ID NO:9), is used.

TABLE 5

Human Repressor of E1-stimulated Genes

| | |
|---|---|
| Human Cellular Repressor of E1-stimulated Genes | MAGLSRGSARALLAALLASTLLALLVSPARGRGGRDHGDWDEASRLPPLPPRED AARVARFVTHVSDWGALATISTLEAVRGRPFADVLSLSDGPPGAGSGVPYFYLS PLQLSVSNLQENPYATLTMTLAQTNFCKKHGFDPQSPLCVHIMLSGTVTKVNET EMDIAKHSLFIRHPEMKTWPSSHNWFFAKLNITNIWVLDYFGGPKIVTPEEYYN VTVQ (SEQ ID NO: 7) |
| Human Cellular Repressor of E1-stimulated Genes Peptide (CREG) | RGGRDHGDWDEASRLPPLPPREDAARVARFVTHVSDWGALATISTLEAVRGRPF ADVLSLSDGPPGAGSGVPYFYLSPLQLSVSNLQENPYATLTMTLAQTNFCKKHG FPLCVHIMLSGTVTKVNETEMDIAKHSLFIRHPEMKTWPSSHNWFFAKLNITNI WVLDYFGGPKIVTPEEYYNVTVQ (SEQ ID NO: 9) |

In some embodiments, a lysosomal targeting moiety is a modified human Cellular Repressor of E1A-stimulated Genes sequence containing amino acid substitutions, insertions or deletions. In some embodiments, a lysosomal targeting moiety has a sequence at least 50%, 55%, 60%, 65%, 70%, 75%, 80%, 85%, 90%, 95%, 98%, or 99% identical to the sequence of human Cellular Repressor of E1A-stimulated Genes (SEQ ID NO:7). In some embodiments, a lysosomal targeting moiety is a fragment of human Cellular Repressor of E1A-stimulated Genes. In some embodiments, a lysosomal targeting moiety is a modified human Cellular Repressor of E1A-stimulated Genes sequence containing amino acid substitutions, insertions or deletions. In some embodiments, a lysosomal targeting moiety has a sequence at least 50%, 55%, 60%, 65%, 70%, 75%, 80%, 85%, 90%, 95%, 98%, or 99% identical to human Cellular Repressor of E1A-stimulated Genes Peptide (CREG) (SEQ ID NO:9). In some embodiments, a lysosomal targeting moiety is a fragment of CREG. In some embodiments, a lysosomal targeting moiety contains human Cellular Repressor of E1A-stimulated Genes (SEQ ID NO:7) or CREG (SEQ ID NO:9) that has one or more N-terminal, C-terminal or internal deletions. In some embodiments, a lysosomal targeting moiety is a modified human Cellular Repressor of E1A-stimulated Genes or CREG that has diminished binding affinity for receptors.

Various additional lysosomal targeting moieties are known in the art and can be used to practice the present invention. For example, certain peptide-based lysosomal targeting moieties are described in U.S. Pat. Nos. 7,396,811, 7,560,424, and 7,629,309; U.S. Application Publication Nos. 2003-0082176, 2004-0006008, 2003-0072761, 20040005309, 2005-0281805, 2005-0244400, and international publications WO 03/032913, WO 03/032727, WO 02/087510, WO 03/102583, WO 2005/078077, WO/2009/137721, the entire disclosures of which are incorporated herein by reference.

In some embodiments, a lysosomal targeting moiety is any polypeptide that is M6P phosphorylated by the cell. In some embodiments, the polypeptide is capable of binding to the CI-M6PR. In some embodiments, the polypeptide is an amino acid sequence found within a protein selected from the group consisting of Cathepsin B, Cathepsin D, Cathepsin L, Beta-Glucuroidase, Beta-Mannosidase, Alpha-Fucosidase, Beta-Hexosaminidase, Arylsulfatase, Beta-Galactosidase, Phosphomannan, Latent TGFbeta, Leukemia Inhibitory Factor, Proliferin, Prorenin, Herpes Simplex Virus, PI-LLC cleaved GPI anchor, Retinoic Acid, IGFII, Plasminogen, Thyroglobulin, TGFbetaR-V, CD87, GTP-binding Proteins (Gi-1, Gi-2 and Gi-3), HA-I Adaptin, HA-II Adaptin and combinations thereof. In some embodiments, the amino acid sequence includes a domain, fragment, region or segment of one or more proteins selected from the group consisting of Cathepsin B, Cathepsin D, Cathepsin L, Beta-Glucuroidase, Beta-Mannosidase, Alpha-Fucosidase, Beta-Hexosaminidase, Arylsulfatase, Beta-Galactosidase, Phosphomannan, Latent TGFbeta, Leukemia Inhibitory Factor, Proliferin, Prorenin, Herpes Simplex Virus, PI-LLC cleaved GPI anchor, Retinoic Acid, IGFII, Plasminogen, Thyroglobulin, TGFbetaR-V, CD87, GTP-binding Proteins (Gi-1, Gi-2 and Gi-3), HA-I Adaptin, HA-II Adaptin and combinations thereof. In some embodiments, the polypeptide is produced synthetically. In some embodiments, the polypeptide is produced recombinantely. Both approaches are widely used in the art and described, for example, in Sambrook et al., Molecular Cloning: A Laboratory Manual, Cold Spring Harbor Laboratory Press (2001).

Linking the Lysosomal Targeting Moiety with the Lysosomal Enzyme—Fusion Proteins The lysosomal targeting moiety may be coupled to the lysosomal enzyme in any of the ways generally known in the art. Non-limiting examples include creating a fusion protein by genetic means or by chemical coupling. In some embodiments, the lysosomal targeting moiety is fused to the N-terminus of the lysosomal enzyme, and in other embodiments the lysosomal targeting moiety is fused to the C-terminus of the lysosomal enzyme. In some embodiments, the lysosomal targeting moiety is located internally, i.e., within the lysosomal enzyme polypeptide. Creating fusion proteins is standard in the art described in detail in Sambrook et al., Molecular Cloning: A Laboratory Manual, Cold Spring Harbor Laboratory Press (2001). It is contemplated that within the scope of the invention more than one lysosomal targeting moiety may be coupled with a suitable lysosomal enzyme.

In some embodiments of the present invention, the targeted therapeutic is a fusion protein. A fusion protein is a polypeptide that is generated from two or more smaller polypeptides. Fusion proteins may be made by recombinant DNA technology, which is standard in the art and described in detail in Sambrook et al.

Non-limiting examples of fusion proteins within the scope of the present invention are disclosed in the Examples section herein. In some embodiments, the fusion proteins have one of the following amino acid sequences: SEQ ID NO: 23, 24, 25 or 26. In some embodiments, the fusion protein is at least 70, 75, 80, 85, 90, 95 or 100% identical to any one of these sequences.

Linker or Spacer

A lysosomal targeting moiety may be fused to the N-terminus or C-terminus of a suitable lysosomal enzyme polypeptide, or inserted internally. The lysosomal targeting moiety may be fused directly to the lysosomal enzyme polypeptide or may be separated from the lysosomal enzyme polypeptide by a linker or a spacer. An amino acid linker or spacer is generally designed to be flexible or to interpose a structure, such as an alpha-helix, between the two protein moieties. A linker or spacer may be relatively short, such as a poly "GAG" sequence GGGGGAAAAGGGG (SEQ ID NO:10), a "GAP" sequence of GAP (SEQ ID NO:11), a "PolyGP" sequence of GGGGGP (SEQ ID NO:12), or can be longer, such as, for example, 10-50 (e.g., 10-20, 10-25, 10-30, 10-35, 10-40, 10-45, 10-50) amino acids in length. In some embodiments, various short linker sequences can be present in tandem repeats. For example, a suitable linker may contain the "GAG" amino acid sequence of GGGGGAAAAGGGG (SEQ ID NO:10) present in tandem repeats. In some embodiments, such as linker may further contain one or more "GAP" sequences, that frames the "GAG" sequence of GGGGGAAAAGGGG (SEQ ID NO:10). For example, in some embodiments a GAG2 linker may be used, which contains two tandem "GAG" repeats, each framed by a "GAP" sequence, such as GAPGGGGGAAAAGGGGGAPGGGGGAAAAGGGGG AP (SEQ ID NO:13). In some embodiments a GAG3 linker may be used, which contains three tandem "GAG" repeats, each framed by two "GAP" sequences, such as GAPGGGGGAAAAGGGGGAPGGGGGAAAAAGG GGGGAPGGGGGAAAAAGGGGG GAP (SEQ ID NO:14). In some embodiments, a suitable linker or spacer may contain a sequence at least 50%, 55%, 60%, 65%, 70%, 75%, 80%, 85%, 90%, 95%, 98%, or 99% identical to the sequence of SEQ ID NO:14.

In some embodiments, a suitable linker or spacer may contain the following sequence: GAPGGGGGAAAAGGGGGAPGGGGGAAAAAGG GGGGAPGGGGGAAAAAGGGGG GAP (SEQ ID NO.: 15). In some embodiments, a suitable linker or spacer may contain a sequence at least 50%, 55%, 60%, 65%, 70%, 75%, 80%, 85%, 90%, 95%, 98%, or 99% identical to the sequence of SEQ ID NO:15.

Vectors

In one aspect, the invention provides a nucleic acid encoding any of the fusion proteins disclosed herein. In one aspect, the present invention provides a vector including said nucleic acid. The term nucleic acid is described in detail in the definition section herein. Vectors for expression of the proteins described herein and/or other components of the invention include plasmid vectors, as well as double or single-stranded RNA or DNA viral vectors. Vectors may be introduced directly into cells as DNA or through indirect use of phages and viruses. Vectors are commonly known in th art and described in detail in Sambrook et al., Molecular Cloning: A Laboratory Manual, Cold Spring Harbor Laboratory Press (2001).

Host Cells

In one aspect, the present invention provides a host cell including a vector. Suitable host cells can be derived from a variety of organisms, including, but not limited to, mammals, plants, birds (e.g., avian systems), insects, yeast, and bacteria. In some embodiments, host cells are mammalian cells. Any mammalian cell susceptible to cell culture, and to expression of polypeptides, may be utilized in accordance with the present invention as a host cell. Non-limiting examples of mammalian cells that may be used in accordance with the present invention include human embryonic kidney 293 cells (HEK293), HeLa cells; BALB/c mouse myeloma line (NSO/l, ECACC No: 85110503); human retinoblasts (PER.C6 (CruCell, Leiden, The Netherlands)); monkey kidney CV1 line transformed by SV40 (COS-7, ATCC CRL 1651); human fibrosarcomacell line (e.g., HT-1080); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells +/−DHFR (CHO, Urlaub and Chasin, Proc. Natl. Acad. Sci. USA, 77:4216 (1980)); mouse sertoli cells (TM4, Mather, Biol. Reprod., 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); MRC 5 cells; FS4 cells; a human hepatoma line (Hep G2), Chinese hamster ovary cells (CHO cells), human cell line CAP and AGELHN, and Glycotope's panel.

In some embodiments, host cells are non-mammalian cells. Suitable non-mammalian cells include prokaryotes, archae, yeast and other eukaryotic cells. Non-limiting examples of non-mammalian host cells suitable for the present invention include yeast cells and cell lines derived from *Pichia pastoris, Pichia methanolica, Pichia angusta, Schizosacccharomyces pombe, Saccharomyces cerevisiae*, and *Yarrowia lipolytica*; insect cells and cell lines derived from *Sodoptera frugiperda, Trichoplusis ni, Drosophila melanogaster* and *Manduca sexta*; and cells and cell lines derived from *Escherichia coli, Salmonella typhimurium, Bacillus subtilis, Bacillus licheniformis, Bacteroides fragilis, Clostridia perfringens, Clostridia difficile*; and amphibian cells and cell lines derived *Xenopus Laevis*.

GNPT

In some embodiments of the present invention, the host cell co-expresses GNPT. Typically, therapeutic glycoproteins, such as lysosomal enzymes, are heavily influenced by a post-translational modification in order to ensure proper function. As described throughout the specification, lysosomal proteins belong to a class of enzymes known as acid hydrolases and are synthesized as soluble or membrane-integrated glycoproteins at the rough endoplasmic reticulum. The N-linked oligosaccharides of the soluble lysosomal enzymes are modified along the transit to and through the Golgi complex to expose mannose-6-phosphate (M6P) recognition markers. These M6P recognition markers are recognized in the trans-Golgi network (TGN) by cation mannose-6-phosphate receptors (CI-M6PR), which results in clustering and packaging into AP1-clathrin-coated vesicles. After fusion with endosomes, the receptors release their ligands, delivering the lysosmal enzymes to a newly formed lysosome. In the event lysosomal proteins fail to bind M6P receptors in the trans-Golgi network, such as in the case of I-cell disease in which there is a deficiency in the phosphotrasferase, the proteins are secreted from the cell resulting in excessive amount of lysomal enzymes in body fluids such as plasma, cerebrospinal fluid, tears and urine. Since cation mannose-6-phosphate receptors are important for the recycling and retrograde movement of lysosomal enzymes to and from the cell surface, the CI-M6PR can serve as an important target for lysosmal-mediated cellular delivery of a therapeutic glycoprotein in enzyme replacement therapy.

Given the cellular importance of protein targeting, modification of N-linked oligosaccharides to expose mannose-6-phosphate recognition tags, as in the case of lysosomal enzymes, is tightly regulated. The M6P residues are generated in a two-step process. First, N-acetylglucosamine 1-phosphate is attached to the C6-hydroxyl group of mannose, followed by removal of N-acetylglucosamine. The first reaction is catalyzed by the UDP-GlcNAc:lysosomal enzyme N-acetylgucosamine-1-phosphotransferase (GNPT), while the second is by an alpha-N-acetylglucosaminidase. GNPT enzyme is a hexameric complex containing three distinct subunits (α, β, γ). The lysosomal protein binds within the active cleft of the molecule, where the enzyme catalyzes the addition of N-acetylglucosamine 1-phosphate to the protein; making use of uridine diphosphate N-acetylglucosamine (UDP-GlcNAc) as the molecular substrate.

The ability of a therapeutic glycoprotein (i.e., lysosomal enzyme) to traffic in and out of the cell is typically positively correlated with its level of M6P phosphorylation. For example, the glycosylation level of one or more therapeutic glycoproteins (i.e. -lysosomal enzymes) and their ability to traffic may vary based on their level of M6P phosphorylation (mono- or bis-phosphorylation).

In some embodiments, a GNPT enzyme suitable for the present invention is human GNPT protein (SEQ ID NO:16 and/or 17). In some embodiments, a suitable GNPT enzyme may be a homologue or an ortholog of mature human GNPT protein. For example, a homologue or an ortholog of mature human GNPT protein may be a modified mature human GNPT protein containing one or more amino acid substitutions, deletions, and/or insertions as compared to a wild-type or naturally-occurring GNPT protein (e.g., SEQ ID NO:16 and/or 17), while retaining substantial GNPT protein activity. Thus, in some embodiments, a GNPT enzyme suitable for the present invention is substantially homologous to human GNPT protein (SEQ ID NO:16 and/or 17). In some embodiments, a GNPT enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:16 and/or 17. In some embodiments, a GNPT enzyme suitable for the present invention is substantially identical to mature human GNPT protein (SEQ ID NO:16 and/or 17). In some embodiments, a GNPT enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:16 and/or 17. In some embodiments, a GNPT enzyme suitable for the present invention contains a fragment or a portion of mature human GNPT protein.

TABLE 6

Human GNPT Protein

| | |
|---|---|
| Human N-acetylgucosamine-1-phosphotransferase (Alpha and Beta subunits) *Underlined Region -TGRQLK- is alpha/beta cleavage site | MLFKLLQRQTYTCLSHRYGLYVCFLGVVVTIVSAFQFGEVVLEWSRDQYHVLFD SYRDNIAGKSFQNRLCLPMPIDVVYTWVNGTDLELLKELQQVREQMEEEQKAMR EILGKNTTEPTKKSEKQLECLLTHCIKVPMLVLDPALPANITLKDLPSLYPSFH SASDIFNVAKPKNPSTNVSVVVFDSTKDVEDAHSGLLKGNSRQTVWRGYLTTDK EVPGLVLMQDLAFLSGFPPTFKETNQLKTKLPENLSSKVKLLQLYSEASVALLK LNNPKDFQELNKQTKKNMTIDGKELTISPAYLLWDLSAISQSKQDEDISASRFE DNEELRYSLRSIERHAPWVRNIFIVTNGQIPSWLNLDNPRVTIVTHQDVFRNLS HLPTFSSPAIESHIHRIEGLSQKFIYLNDDVMFGKDVWPDDFYSHSKGQKVYLT WPVPNCAEGCPGSWIKDGYCDKACNNSACDWDGGDCSGNSGGSRYIAGGGGTGS IGVGQPWQFGGGINSVSYCNQGCANSWLADKFCDQACNVLSCGFDAGDCGQDHF HELYKVILLPNQTHYTIPKGECLPYFSFAEVAKRGVEGAYSDNPIIRHASIANK WKTIHLIMHSGMNATTIHFNLTFQNTNDEEFKMQITVEVDTREGPKLNSTAQKG YENLVSPITLLPEAEILFEDIPKEKRFPKFKRHDVNSTRRAQEEVKIPLVNISL LPKDAQLSLNTLDLQLEHGDITLKGYNLSKSALLRSFLMNSQHAKIKNQATITD ETNDSLVAPQEKQVHKSILPNSLGVSERLQRLTFPAVSVKVNGHDQGQNPPLDL ETTARFRVETHTQKTIGGNVTKEKPPSLIVPLESQMTKEKKITGKEKENSRMEE NAENHIGVTEVLLGRKLQHYTDSYLGFLPWEKKKYFQDLLDEEESLKTQLAYFT DSKN<u>TGRQLK</u>DTFADSLRYVNKILNSKFGFTSRKVPAHMPHMIDRIVMQELQDM FPEEFDKTSFHKVRHSEDMQFAFSYFYYLMSAVQPLNISQVFDEVDTDQSGVLS DREIRTLATRIHELPLSLQDLTGLEHMLINCSKMLPADITQLNNIPPTQESYYD PNLPPVTKSLVTNCKPVTDKIHKAYKDKNKYRFEIMGEEETAFKMIRTNVSHVV GQLDDIRKNPRKFVCLNDNIDHNHKDAQTVKAVLRDFYESMFPIPSQFEL<u>P</u>REY RNRFLHMHELQEWRAYRDKLKFWTHCVLATLIMFTIFSFFAEQLIALKRKIFPR RRIHKEASPNRIRV (SEQ ID NO: 16) |
| Human N-acetylgucosamine-1-phosphotransferase (Gamma Subunit) | MAAGLARLLLLLGLSAGGPAPAGAAKMKVVEEPNAFGVNNPFLPQASRLQAKRD PSPVSGPVHLFRLSGKCFSLVESTYKYEFCPFHNVTQHEQTFRWNAYSGILGIW HEWEIANNTFTGMWMRDGDACRSRSRQSKVELACGKSNRLAHVSEPSTCVYALT FETPLVCHPHALLVYPTLPEALQRQWDQVEQDLADELITPQGHEKLLRTLFEDA GYLKTPEENEPTQLEGGPDSLGFETLENCRKAHKELSKEIKRLKGLLTQHGIPY TRPTETSNLEHLGHETPRAKSPEQLRGDPGLRGSL (SEQ ID NO: 17) |

Overexpression of enzymes, including GNPT, in host cells and tissue culture is routine and described in detail in Sambrook et al.

Culture Conditions

The present invention provides a method of producing recombinant targeted therapeutic glycoproteins using a GNPT cell culture system. In some embodiments, the cell culture system is used for microscale production of a therapeutic glycoprotein. In some embodiments, the cellular culture system is used for large scale production. In some embodiments the therapeutic glycoprotein produced is a recombinant lysosomal enzyme. Typical large-scale procedures for producing a recombinant polypeptide of interest include batch cultures and fed-batch cultures. Batch culture processes traditionally comprise inoculating a large-scale production culture with a seed culture of a particular cell density, growing the cells under conditions (e.g., suitable culture medium, pH, and temperature) conducive to cell growth, viability, and/or productivity, harvesting the culture when the cells reach a specified cell density, and purifying the expressed polypeptide. Fed-batch culture procedures include an additional step or steps of supplementing the batch culture with nutrients and other components that are consumed during the growth of the cells. In some embodiments, a large-scale production method according to the present invention uses a fed-batch culture system.

Bioreactors

The invention also provides bioreactors that are useful for producing recombinant therapeutic glycoproteins. Bioreactors may be perfusion, batch, fed-batch, repeated batch, or continuous (e.g. a continuous stirred-tank reactor models), for example. Typically, the bioreactors comprise at least one vessel designed and are configured to house medium (e.g., a chemically defined nutrient medium). The vessel also typically comprises at least one inlet designed and configured to flow fresh nutrient medium into the vessel. The vessel also typically comprises at least one outlet designed and configured to flow waste medium out of the vessel. In some embodiments, the vessel may further comprise at least one filter designed and configured to minimize the extent to which isolated cells in the vessel are passed out through the at least one outlet with waste medium. The bioreactor may also be fitted with one or more other components designed to maintain conditions suitable for cell growth. For example, the bioreactor may be fitted with one or more circulation or mixing devices designed and configured to circulate or mix the nutrient medium within the vessel. Typically, the isolated cells that are engineered to express recombinant therapeutic glycoproteins are suspended in the nutrient medium. Therefore, in some cases, the circulation device ensures that the isolated cells remain in suspension in the nutrient medium. In some cases, the cells are attached to a substrate. In some cases, the cells are attached to one or more substrates (e.g., microbeads) that are suspended in the nutrient medium. The bioreactor may comprise one or more ports for obtaining a sample of the cell suspension from the vessel. The bioreactor may be configured with one or more components for monitoring and/or controlling conditions of the culture, including conditions such as gas content (e.g., air, oxygen, nitrogen, carbon dioxide), flow rates, temperature, pH and dissolved oxygen levels, and agitation speed/circulation rate.

Vessels of any appropriate size may be used in the bioreactors. Typically, the vessel size is suitable for satisfying the production demands of manufacturing recombinant I2S. In some embodiments, the vessel is designed and configured to contain up to 1 L, up to 10 L, up to 100 L, up to 500 L, up to 1000 L, up to 1500 L, up to 2000 L, or more of the nutrient medium. In some embodiments, the volume of the production bioreactor is at least 10 L, at least 50 L, 100 L, at least 200 L, at least 250 L, at least 500 L, at least 1000 L, at least 1500 L, at least 2000 L, at least 2500 L, at least 5000 L, at least 8000 L, at least 10,000 L, or at least 12,000 L, or more, or any volume in between. The production bioreactor may be constructed of any material that is conducive to cell growth and viability that does not interfere with expression or stability or activity of the produced therapeutic glycoprotein. Exemplary material may include, but not be limited to, glass, plastic, or metal.

In some embodiments, cells may be cultured in a chemically defined medium that is housed in a vessel of a bioreactor. The culture methods often involve perfusing fresh nutrient medium into the vessel through the at least one inlet and bleeding waste nutrient medium out from vessel through the at least one outlet. Bleeding is performed at a rate of up to about 0.1 vessel volume per day, about 0.2 vessel volume per day, about 0.3 vessel volume per day, about 0.4 vessel volume per day, about 0.5 vessel volume per day, about 1 vessel volume per day, about 1.5 vessel volumes per day or more. The methods also involve harvesting nutrient medium that comprises recombinant the recombinant glycoprotein. In some embodiments, the therapeutic glycoproteins may be a lysosomal enzyme. In some embodiments, the therapeutic glycoprotein may be a fusion protein. Harvesting may be performed at a rate of up to about 0.1 vessel volume per day, about 0.2 vessel volume per day, about 0.3 vessel volume per day, about 0.4 vessel volume per day, about 0.5 vessel volume per day, about 1 vessel volume per day, about 1.5 vessel volumes per day or more. Perfusing is also performed, typically at a rate equivalent to the sum of the bleeding rate and the harvesting rate. For example, perfusion rate may be great than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0 vessel volume per day. In some embodiments, perfusion rate is less than about 5.0, 4.5, 4.0, 3.5, 3.0, 2.5, 2.0, 1.5, 1.4, 1.3, 1.2, 1.1, 1.0, 0.9, 0.8, 0.7, 0.6, 0.5 vessel volume per day.

Monitoring Culture Conditions

In certain embodiments of the present invention, the practitioner may find it beneficial or necessary to periodically monitor particular conditions of the growing cell culture. Monitoring cell culture conditions allows the practitioner to determine whether the cell culture is producing recombinant polypeptide or protein at suboptimal levels or whether the culture is about to enter into a suboptimal production phase. In order to monitor certain cell culture conditions, it will be necessary to remove small aliquots of the culture for analysis.

As non-limiting example, it may be beneficial or necessary to monitor temperature, pH, cell density, cell viability, integrated viable cell density, osmolarity, or titer or activity of the expressed therapeutic glycoprotein protein. Numerous techniques are well known in the art that will allow one of ordinary skill in the art to measure these conditions. For example, cell density may be measured using a hemacytometer, a Coulter counter, or Cell density examination (CE-DEX). Viable cell density may be determined by staining a culture sample with Trypan blue. Since only dead cells take up the Trypan blue, viable cell density can be determined by counting the total number of cells, dividing the number of cells that take up the dye by the total number of cells, and taking the reciprocal. Alternatively, the level of the expressed therapeutic glycoprotein can be determined by standard molecular biology techniques such as coomassie staining of SDS-PAGE gels, Western blotting, Bradford assays, Lowry assays, Biuret assays, and UV absorbance.

Figure 10:
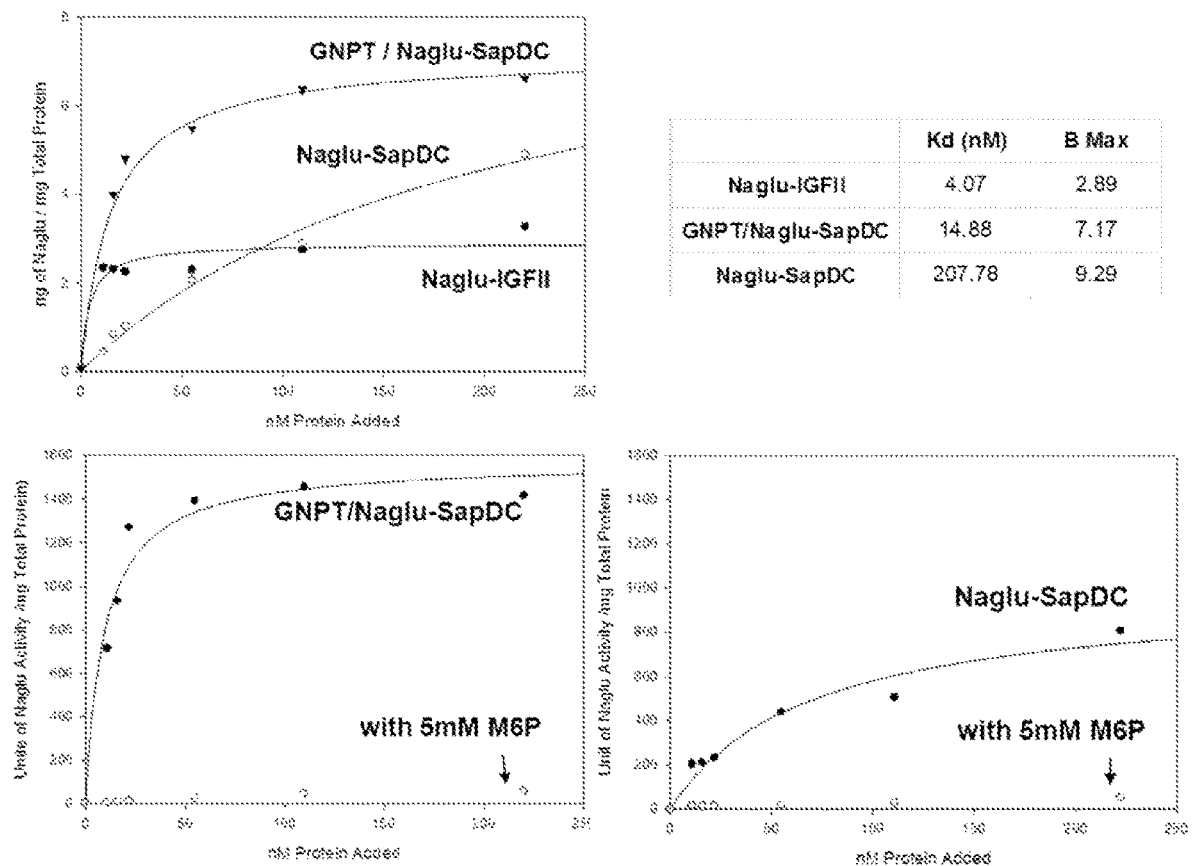
FIG. 10 illustrates in vitro cellular uptake of Naglu-SapDC produced in wild-type HT1080 cells or an N-acetylgucosamine-1-phosphotransferase (GNPT) overexpressing cell line. Cellular uptake of Naglu-IGFII was used as a control.

It may also be beneficial or necessary to monitor the level of M6P phosphorylation and/or glycan pattern to generate a glycosylation profile, as demonstrated in FIGS. 9-10 of the application. For example, in some embodiments, analysis can be performed to monitor glycan critical quality attributes such as antennary fucosylation, glactosylation, sialyation, high mannose structure and phosphorylation structures. In some embodiments, analysis can be performed to characterize the recombinantly produced glycoprotein in relation to a reference sample. In some embodiments, analysis can be performed to characterize the recombinantly produced glycoprotein in relation to a previous lot or batch of the sample protein produced under identical conditions. In some embodiments, analysis can be performed to characterize the recombinantly produced glycoprotein in relation to a previous lot or batch of the sample protein produced under different conditions. In some embodiments, analysis can be performed to characterize the recombinantly produced glycoprotein in relation to a previous lot or batch of the sample protein produced at a different stage of production.

The GNPT cell line can be used to recombinantly produce a therapeutic glycoprotein with increased levels of M6P phosphorylation. In some embodiments, the recombinant therapeutic glycoprotein produced using the GNPT cell line has M6P levels higher than the naturally occurring therapeutic glycoprotein. In some embodiments, the recombinant therapeutic glycoprotein has M6P phosphorylation levels higher than the same therapeutic glycoprotein recombinantly produced in the non-GNPT overexpressing cell line. In some embodiments, the increase in M6P phosphorylation compared to production in a non-GNPT overexpressing cell line is at least 1 fold. In some embodiments, the increase in M6P phosphorylation is at least a 2, 3, 4, 5, 6, 7, 8, 9, 10, 15, 20, 25, 30, 35, 40, 45, 50, 60, 70, 80, or 90 fold increase. In some embodiments, the increase in M6P phosphorylation at least a 1%, 2%, 3%, 4%, 5%, 6%, 7%, 8%, 9%, 10%, 15%, 20%, 30%, 40%, 50%, 60%, 70%, 80% or 90% increase. In some embodiments, the recombinant therapeutic glycoprotein produced using the GNPT cell line has M6P levels at least 10%, 20%, 30%, 40%, 50%, 60%, 70%, 80%, or 90% higher than the wild-type therapeutic glycoprotein.

In some embodiments, a recombinant therapeutic glycoprotein produced using the GNPT cell line may contain at least one M6P residue. In some embodiments, a recombinant therapeutic glycoprotein may contain a plurality of M6P residues. In some embodiments, a recombinant therapeutic glycoprotein may be a bis-phosphorylated glycoprotein with two M6P residues. In some embodiments, a recombinant therapeutic glycoprotein produced using the GNPT cell line may contain at least 1, 2, 3, 4, 5, 6, 7, 8, 9 or 10 M6P residues compared to the wild-type protein.

In some embodiments, a recombinant therapeutic glycoprotein may contain an increase in the number and/or level of high mannose structures, such as, M3, M4, M5, M6, M7 or M8 structures, compared to the wild-type protein. In some embodiments, the increase in M3 structures is 1, 2, 3, 4, 5, 6, 7, 8, 9, 10, 11, 12, 13, 14, 15, 20, 25, 30, 35, 40, 45, 50, 55, 60, 65, 70, 75, 80, 85, or 90 percent compared to the wild-type protein. In some embodiments, the increase in M4 structures is 1, 2, 3, 4, 5, 6, 7, 8, 9, 10, 11, 12, 13, 14, 15, 20, 25, 30, 35, 40, 45, 50, 55, 60, 65, 70, 75, 80, 85, or 90 percent compared to the wild-type protein. In some embodiments, the increase in M5 structures is 1, 2, 3, 4, 5, 6, 7, 8, 9, 10, 11, 12, 13, 14, 15, 20, 25, 30, 35, 40, 45, 50, 55, 60, 65, 70, 75, 80, 85, or 90 percent compared to the wild-type protein. In some embodiments, the increase in M6 structures is 1, 2, 3, 4, 5, 6, 7, 8, 9, 10, 11, 12, 13, 14, 15, 20, 25, 30, 35, 40, 45, 50, 55, 60, 65, 70, 75, 80, 85, or 90 percent compared to the wild-type protein. In some embodiments, the increase in M7 structures is 1, 2, 3, 4, 5, 6, 7, 8, 9, 10, 11, 12, 13, 14, 15, 20, 25, 30, 35, 40, 45, 50, 55, 60, 65, 70, 75, 80, 85, or 90 percent compared to the wild-type protein. In some embodiments, the increase in M8 structures is 1, 2, 3, 4, 5, 6, 7, 8, 9, 10, 11, 12, 13, 14, 15, 20, 25, 30, 35, 40, 45, 50, 55, 60, 65, 70, 75, 80, 85, or 90 percent compared to the wild-type protein.

In some embodiments, the recombinant therapeutic glycoprotein may contain and increase in the number and/or level of total phosphorylated structures, compared to the wild-type protein. In some embodiments, the increase in total phosphorylated structures compared to the wild-type protein is 1, 2, 3, 4, 5, 6, 7, 8, 9, 10, 11, 12, 13, 14, 15, 20, 25, 30, 35, 40, 45, 50, 55, 60, 65, 70, 75, 80, 85, or 90 percent.

In some embodiments, a recombinant therapeutic glycoprotein produced using the GNPT cell line may contain a higher level of antennary structures compared to the wild type protein. In particular, therapeutic glycoproteins produced with the GNPT cell line may have a higher level of A0 antennarity, which is indicative of M6P phosphorylation. In some embodiments, the increase in A0 level compared to the wild-type protein is at least 1, 2, 3, 4, 5, 6, 7, 8, 9, 10, 11, 12, 13, 14, 15, 20, 25, 30, 35, 40, 45, 50, 55, 60, 65, 70, 75, 80, 85, or 90 percent.

In some embodiments, a therapeutic protein suitable for the present invention may contain a bis-phosphorylated oligosaccharides which have higher binding affinity to the CI-M6PR. In some embodiments, a suitable enzyme contains up to about an average of about at least 20% bis-phosphorylated oligosaccharides per enzyme. In other embodiments, a suitable enzyme may contain about 10%, 15%, 18%, 20%, 25%, 30%, 35%, 40%, 45%, 50%, 55%, 60% bis-phosphorylated oligosaccharides per enzyme.

In some embodiments, the increased level in M6P phosphorylation of the therapeutic glycoprotein, as a result of producing using the GNPT cell line, may be tested using any of a variety of well-known binding assays to evaluate the level of CI-M6PR binding. In some embodiments, therapeutic glycoproteins produced using the GNPT cell line have an increase in CI-M6PR of 1, 2, 3, 4, 5, 6, 7, 8, 9, 10, 11, 12, 13, 14, 15, 16, 17, 18, 19, 20, 25, 30, 35, 40, 45, 50, 60, 70, 80, or 90 fold compared to the native protein.

In some embodiments, the level of M6P phosphorylation may be tested by monitoring binding of a therapeutic glycoprotein to the CI-M6PR using any of a variety of well-known in vitro binding assay such as, but not limited to, radiolabeled run on assay, radiolabeled binding assay, ELISA, Surface Plasmone Resonance and Isothermal Titration calorimetry. In some embodiments, the level of M6P phosphorylation may be tested by monitoring binding of a therapeutic glycoprotein to the CI-M6PR by evaluating cellular uptake using methods such as, but not limited to, immunohistochemistry staining, fluorescent immunohistochemistry staining and confocal microscopy. In some embodiments, the level of M6P phosphorylation may be assays using analytical techniques such as, but not limited to, glycosidase treatment, mass spectrometry and HPLC.

Purification of Therapeutic Glycoproteins

Various methods may be used to purify or isolate therapeutic glycoproteins produced according to various methods described herein. In some embodiments, the expressed therapeutic glycoprotein protein (e.g., lysosomal enzymes) may be secreted into the medium and thus cells and other solids may be removed, as by centrifugation or filtering for example, as a first step in the purification process. Alternatively or additionally, the expressed therapeutic glycoprotein may be bound to the surface of the host cell. In this embodiment, the host cells (for example, yeast cells) expressing the polypeptide or protein are lysed for purification. Lysis of host cells (e.g., yeast cells) can be achieved by any number of means well known to those of ordinary skill in the art, including physical disruption by glass beads and exposure to high pH conditions.

The therapeutic glycoprotein may be isolated and purified by standard methods including, but not limited to, chromatography (e.g., ion exchange, affinity, size exclusion, and hydroxyapatite chromatography), gel filtration, centrifugation, or differential solubility, ethanol precipitation or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol 182), Academic Press, 1997, all incorporated herein by reference). For immunoaffinity chromatography in particular, the protein may be isolated by binding it to an affinity column comprising antibodies that were raised against that protein and were affixed to a stationary support. Alternatively, affinity tags such as an influenza coat sequence, poly-histidine, or glutathione-S-transferase can be attached to the protein by standard recombinant techniques to allow for easy purification by passage over the appropriate affinity column. Protease inhibitors such as phenyl methyl sulfonyl fluoride (PMSF), leupeptin, pepstatin or aprotinin may be added at any or all stages in order to reduce or eliminate degradation of the polypeptide or protein during the purification process. Protease inhibitors are particularly desired when cells must be lysed in order to isolate and purify the expressed polypeptide or protein. Exemplary purification methods are described in the Examples sections below.

Pharmaceutical Compositions and Administration

The present invention further provides pharmaceutical compositions containing targeted therapeutics according to the present invention. Typically, suitable pharmaceutical compositions contain at least one pharmaceutically acceptable excipient and are formulated for administration to humans.

For example, pharmaceutical compositions provided herein may be provided in a sterile injectable form (e.g., a form that is suitable for subcutaneous, intravenous, or intrathecal injection). For example, in some embodiments, pharmaceutical compositions are provided in a liquid dosage form that is suitable for injection. In some embodiments, pharmaceutical compositions are provided as powders (e.g., lyophilized and/or sterilized), optionally under vacuum, which are reconstituted with an aqueous diluent (e.g., water, buffer, salt solution, etc.) prior to injection. In some embodiments, pharmaceutical compositions are diluted and/or reconstituted in water, sodium chloride solution, sodium acetate solution, benzyl alcohol solution, phosphate buffered saline, etc. In some embodiments, powder should be mixed gently with the aqueous diluent (e.g., not shaken).

In some embodiments, provided pharmaceutical compositions comprise one or more pharmaceutically acceptable excipients (e.g., preservative, inert diluent, dispersing agent, surface active agent and/or emulsifier, buffering agent, etc.). In some embodiments, pharmaceutical compositions comprise one or more preservatives. In some embodiments, pharmaceutical compositions comprise no preservative.

Compositions of the pharmaceutical compositions described herein may be prepared by any method known or hereafter developed in the art of pharmacology. In some embodiments, such preparatory methods include the step of bringing active ingredient into association with one or more excipients and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to a dose which would be administered to a subject and/or a convenient fraction of such a dose such as, for example, one-half or one-third of such a dose.

Relative amounts of active ingredient, pharmaceutically acceptable excipient, and/or any additional ingredients in a pharmaceutical composition in accordance with the invention may vary, depending upon the identity, size, and/or condition of the subject treated and/or depending upon the route by which the composition is to be administered. By way of example, the composition may comprise between 0.1% and 100% (w/w) active ingredient.

Pharmaceutical compositions of the present invention may additionally comprise a pharmaceutically acceptable excipient, which, as used herein, may be or comprise solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, pharmaceutical compositions according to the present invention can be used for CNS delivery via various techniques and routes including, but not limited to, intraparenchymal, intracerebral, intravetricular cerebral (ICV), intrathecal (e.g., IT-Lumbar, IT-cisterna magna) administrations and any other techniques and routes for injection directly or indirectly to the CNS and/or CSF.

Intrathecal Delivery

In some embodiments, pharmaceutical compositions according to the present invention can be used for intrathecal administration. As used herein, intrathecal administration (also referred to as intrathecal injection or intrathecal delivery) refers to an injection into the spinal canal (intrathecal space surrounding the spinal cord). Various formulations for intrathecal administration are described in WO/2011/163652, the contents of which are incorporated herein by reference.

According to the present invention, a pharmaceutical composition containing a targeted therapeutics may be injected at any region surrounding the spinal canal. In some embodiments, a pharmaceutical composition containing a targeted therapeutics is injected into the lumbar area or the cisterna magna or intraventricularly into a cerebral ventricle space. As used herein, the term "lumbar region" or "lumbar area" refers to the area between the third and fourth lumbar (lower back) vertebrae and, more inclusively, the L2-S1 region of the spine. Typically, intrathecal injection via the lumbar region or lumber area is also referred to as "lumbar IT delivery" or "lumbar IT administration."

Various devices may be used for intrathecal delivery according to the present invention. In some embodiments, a device for intrathecal administration contains a fluid access port (e.g., injectable port); a hollow body (e.g., catheter) having a first flow orifice in fluid communication with the fluid access port and a second flow orifice configured for insertion into spinal cord; and a securing mechanism for securing the insertion of the hollow body in the spinal cord. As a non-limiting example, a suitable securing mechanism contains one or more nobs mounted on the surface of the hollow body and a sutured ring adjustable over the one or more nobs to prevent the hollow body (e.g., catheter) from slipping out of the spinal cord. In various embodiments, the fluid access port comprises a reservoir. In some embodiments, the fluid access port comprises a mechanical pump (e.g., an infusion pump). In some embodiments, an implanted catheter is connected to either a reservoir (e.g., for bolus delivery), or an infusion pump. The fluid access port may be implanted or external In some embodiments, intrathecal administration may be performed by either lumbar puncture (i.e., slow bolus) or via a port-catheter delivery system (i.e., infusion or bolus). In some embodiments, the catheter is inserted between the laminae of the lumbar vertebrae and the tip is threaded up the thecal space to the desired level (generally L3-L4).

For injection, formulations of the invention can be formulated in liquid solutions. In addition, the enzyme may be formulated in solid form and re-dissolved or suspended immediately prior to use. Lyophilized forms are also included. The injection can be, for example, in the form of a bolus injection or continuous infusion (e.g., using infusion pumps) of the enzyme.

Treatment of San B and Other Lysosomal Storage Diseases

The present invention may be used to effectively treat Sanfilippo Syndrome Type B and other lysosomal storage diseases. Sanfilippo Syndrome Type B, or Mucopolysaccharidosis III B (MPS III B), is a heritable metabolic disorder resulting from a deficiency of the enzyme Naglu. Naglu is localized to lysosomes and plays an important role in the catabolism of glycosaminoglycans (GAGs) heparan- and dermatan-sulfate. In the absence of enzyme, these substrates accumulate within cells, ultimately causing engorgement, followed by cellular death and tissue destruction. Due to the widespread expression of enzyme, multiple cell types and organ systems are affected in MPS III B patients.

A defining clinical feature of this disorder is central nervous system (CNS) degeneration, which results in cognitive impairment (e.g., decrease in IQ). Additionally, MRI scans of affected individuals have revealed white matter lesions, dilated perivascular spaces in the brain parenchyma, ganglia, corpus callosum, and brainstem; atrophy; and ventriculomegaly (Wang et al. Molecular Genetics and Metabolism, 2009). The disease typically manifests itself in the first years of life with organomegaly and skeletal abnormalities. Some affected individuals experience a progressive loss of cognitive function, with most affected individuals dying of disease-associated complications in their first or second decade.

Compositions and methods of the present invention may be used to effectively treat individuals suffering from or susceptible to Sanfilippo Syndrome Type B. The terms, "treat" or "treatment," as used herein, refers to amelioration of one or more symptoms associated with the disease, prevention or delay of the onset of one or more symptoms of the disease, and/or lessening of the severity or frequency of one or more symptoms of the disease.

In some embodiments, treatment refers to partially or complete alleviation, amelioration, relief, inhibition, delaying onset, reducing severity and/or incidence of neurological impairment in a Sanfilippo Syndrome Type B patient. As used herein, the term "neurological impairment" includes various symptoms associated with impairment of the central nervous system (e.g., the brain and spinal cord). Symptoms of neurological impairment may include, for example, e.g., cognitive impairment; white matter lesions; dilated perivascular spaces in the brain parenchyma, ganglia, corpus callosum, and/or brainstem; atrophy; and/or ventriculomegaly, among others.

The terms, "improve," "increase" or "reduce," as used herein, indicate values that are relative to a control. In some embodiments, a suitable control is a baseline measurement, such as a measurement in the same individual prior to initiation of the treatment described herein, or a measurement in a control individual (or multiple control individuals) in the absence of the treatment described herein. A "control individual" is an individual afflicted with a lysosomal storage disease (e.g., Sanfillipo Syndrome Type B), who is about the same age and/or gender as the individual suffering from the same lysosmal storage disease, who is being treated (to ensure that the stages of the disease in the treated individual and the control individual(s) are comparable).

The individual (also referred to as "patient" or "subject") being treated is an individual (fetus, infant, child, adolescent, or adult human) having a lysosomal storage disease or having the potential to develop a lysosmal storage disease. In some embodiments, the lysosmal storage disease is Sanfilippo Syndrome. In some specific embodiments the lysosomal storage disease is Sanfilippo Syndrome Type B. The individual can have residual endogenous Naglu expression and/or activity, or no measurable activity. For example, the individual having Sanfilipo Syndrome Type B may have Naglu expression levels that are less than about 30-50%, less than about 25-30%, less than about 20-25%, less than about 15-20%, less than about 10-15%, less than about 5-10%, less than about 0.1-5% of normal Naglu expression levels.

In some embodiments, the individual is an individual who has been recently diagnosed with the disease. Typically, early treatment (treatment commencing as soon as possible after diagnosis) is important to minimize the effects of the disease and to maximize the benefits of treatment.

The invention will be more fully understood by reference to the following examples. They should not, however, be construed as limiting the scope of the invention. All references cited herein are incorporated herein by reference in their entirety.

EXAMPLES

Example 1: Creation of Naglu Fusion Proteins

Several proteins have been implicated in binding to different extracellular regions/domains within the CI-M6P receptor via a M6P-dependant manner, such as Leukemia Inhibitory Factor, Cellular Repressor of E1A-stimulated Genes and Saposin, or via a M6P-independent manner, such as Insulin-like Growth Factor II. Therefore, a series of Naglu-fusion proteins were designed that might bind to CI-M6PR and therefore might facilitate CI-M6PR-mediated delivery of rhNaglu to the lysosome, as described below.

Naglu-SapDC

The Naglu-SapDC protein is a fusion of Naglu and portions of the saposin protein as described below. To create the Naglu-SapDC fusion protein, a nucleic acid construct was created by coupling the human Naglu gene to the sequence encoding the conserved C terminal region and D functional domain of Saposin (SapDC). A GAG3 linker was inserted between the two sequences to allow for rotation between the two peptides following translation. In the resulting Full-Length Naglu-SapDC fusion protein (SEQ ID NO:18), Full-Length Naglu constitutes the N-terminus and the SapDC peptide sequences the C-terminus.

(SEQ ID NO: 18)
MEAVAVAAAVGVLLLAGAGGAAGDEAREAAAVRALVARLLGPGPAADFS

VSVERALAAKPGLDTYSLGGGGAARVRVRGSTGVAAAAGLHRYLRDFCG

CHVAWSGSQLRLPRPLPAVPGELTEATPNRYRYYQNVCTQSYSFVWWDW

ARWEREIDWMALNGINLALAWSGQEAIWQRVYLALGLTQAEINEFFTGP

AFLAWGRMGNLHTWDGPLPPSWHIKQLYLQHRVLDQMRSFGMTPVLPAF

AGHVPEAVTRVFPQVNVTKMGSWGHFNCSYSCSFLLAPEDPIFPIIGSL

FLRELIKEFGTDHIYGADTFNEMQPPSSEPSYLAAATTAVYEAMTAVDT

EAVWLLQGWLFQHQPQFWGPAQIRAVLGAVPRGRLLVLDLFAESQPVYT

RTASFQGQPFIWCMLHNFGGNHGLFGALEAVNGGPEAARLFPNSTMVGT

GMAPEGISQNEVVYSLMAELGWRKDPVPDLAAWVTSFAARRYGVSHPDA

GAAWRLLLRSVYNCSGEACRGHNRSPLVRRPSLQMNTSIWYNRSDVFEA

WRLLLTSAPSLATSPAFRYDLLDLTRQAVQELVSLYYEEARSAYLSKEL

ASLLRAGGVLAYELLPALDEVLASDSRFLLGSWLEQARAAAVSEAEADF

YEQNSRYQLTLWGPEGNILDYANKQLAGLVANYYTPRWRLFLEALVDSV

AQGIPFQQHQFDKNVFQLEQAFVLSKQRYPSQPRGDTVDLAKKIFLKYY

PRWVAGSWGAPGGGGGAAAAAGGGGGGAPGGGGGAAAAAGGGGGGAPGG

GGGAAAAAGGGGGGAP<u>DGGFCEVCKKLVGYLDRNLEK(N)STKQEILAA</u>

<u>LEKGCSFLPDPYQKQCDQFVAEYEPVLIEILVEVMDPSFVCLKIGACPS</u>

<u>AHKPLLGTEKCIWGPSYWCQNTETAAQCNAVEHCKRHVWN</u>

Human Full length Naglu—in italics

GAG3 Linker—in bold

SapDC—underlined

Sites within SapDC sequence (N)—denotes glycosylation sites

Naglu-LIF

The Naglu-LIF protein is a fusion of Naglu and portions of the Leukemia Inhibitory Factor protein as described below. To create the Naglu-LIF fusion protein, a nucleic acid construct was created by coupling the human Naglu gene to the sequence encoding the 102 amino acid sequence comprising the glycosylation sites, and helicies A, B, C and D of the 4 helix bundle of Leukemia Inhibitory Factor (LIF). A GAG3 linker was inserted between the two sequences to allow for rotation between the two peptides following translation. In the resulting Full-Length Naglu-LIF fusion protein (SEQ ID NO:19), Full-Length Naglu constitutes the N-terminus and the LIF peptide sequences the C-terminus.

(SEQ ID NO: 19)
MEAVAVAAAVGVLLLAGAGGAAGDEAREAAAVRALVARLLGPGPAADFS

VSVERALAAKPGLDTYSLGGGGAARVRVRGSTGVAAAAGLHRYLRDFCG

CHVAWSGSQLRLPRPLPAVPGELTEATPNRYRYYQNVCTQSYSFVWWDW

ARWEREIDWMALNGINLALAWSGQEAIWQRVYLALGLTQAEINEFFTGP

AFLAWGRMGNLHTWDGPLPPSWHIKQLYLQHRVLDQMRSFGMTPVLPAF

AGHVPEAVTRVFPQVNVTKMGSWGHFNCSYSCSFLLAPEDPIFPIIGSL

FLRELIKEFGTDHIYGADTFNEMQPPSSEPSYLAAATTAVYEAMTAVDT

EAVWLLQGWLFQHQPQFWGPAQIRAVLGAVPRGRLLVLDLFAESQPVYT

RTASFQGQPFIWCMLHNFGGNHGLFGALEAVNGGPEAARLFPNSTMVGT

GMAPEGISQNEVVYSLMAELGWRKDPVPDLAAWVTSFAARRYGVSHPDA

GAAWRLLLRSVYNCSGEACRGHNRSPLVRRPSLQMNTSIWYNRSDVFEA

WRLLLTSAPSLATSPAFRYDLLDLTRQAVQELVSLYYEEARSAYLSKEL

ASLLRAGGVLAYELLPALDEVLASDSRFLLGSWLEQARAAAVSEAEADF

YEQNSRYQLTLWGPEGNILDYANKQLAGLVANYYTPRWRLFLEALVDSV

AQGIPFQQHQFDKNVFQLEQAFVLSKQRYPSQPRGDTVDLAKKIFLKYY

PRWVAGSWGAPGGGGGAAAAAGGGGGGAPGGGGGAAAAAGGGGGGAPGG

GGGAAAAAGGGGGGAP<u>SPLPITPVNATCAIRHPCHNNLMN{A}IR{A}Q</u>

<u>LA{A}L(N)GSANALFILYYTAQGEPFPNNLDKLCGP(N)VTDFPPFHA</u>

<u>(N)GTEKAKLVELYRIVVYLGTSLG(N)ITRDQKILNPSALSLHSKL</u>

<u>(N)ATADILRGLLSNVLCRLCSKYHVGHVDVTYGPDTSGKDV[[A]]QK</u>

<u>[[A]]KLGCQLLGKYKQIIAVLAQAF</u>

Human Full-Length Naglu—in italics
GAG3 Linker—in bold
LIF—underlined
Sites within LIF Sequence
 (N)—denotes glycosylation sites
 { }—denotes mutations made to alter recognition of the receptor gp130; [[ ]]—denotes mutations made to alter recognition of the LIF receptor Naglu-CREG The Naglu-CREG protein is a fusion of Naglu and portions of the Cellular Repressor of E1A-stimulated Genes protein as described below. To create the Naglu-CREG fusion protein, a nucleic acid construct was created by coupling the human Naglu gene to the sequence encoding the CREG amino acid sequence. A GAG3 linker was inserted between the two sequences to allow for rotation between the two peptides following translation. In the resulting Full-Length Naglu-CREG fusion protein (SEQ ID NO:20), Full-Length Naglu constitutes the N-terminus and the CREG peptide sequences the C-terminus.

(SEQ ID NO: 20)
MEAVAVAAAVGVLLLAGAGGAAGDEAREAAAVRALVARLLGPGPAADFS

VSVERALAAKPGLDTYSLGGGGAARVRVRGSTGVAAAAGLHRYLRDFCG

CHVAWSGSQLRLPRPLPAVPGELTEATPNRYRYYQNVCTQSYSFVWWDW

ARWEREIDWMALNGINLALAWSGQEAIWQRVYLALGLTQAEINEFFTGP

AFLAWGRMGNLHTWDGPLPPSWHIKQLYLQHRVLDQMRSFGMTPVLPAF

AGHVPEAVTRVFPQVNVTKMGSWGHFNCSYSCSFLLAPEDPIFPIIGSL

FLRELIKEFGTDHIYGADTFNEMQPPSSEPSYLAAATTAVYEAMTAVDT

EAVWLLQGWLFQHQPQFWGPAQIRAVLGAVPRGRLLVLDLFAESQPVYT

RTASFQGQPFIWCMLHNFGGNHGLFGALEAVNGGPEAARLFPNSTMVGT

GMAPEGISQNEVVYSLMAELGWRKDPVPDLAAWVTSFAARRYGVSHPDA

GAAWRLLLRSVYNCSGEACRGHNRSPLVRRPSLQMNTSIWYNRSDVFEA

WRLLLTSAPSLATSPAFRYDLLDLTRQAVQELVSLYYEEARSAYLSKEL

ASLLRAGGVLAYELLPALDEVLASDSRFLLGSWLEQARAAAVSEAEADF

YEQNSRYQLTLWGPEGNILDYANKQLAGLVANYYTPRWRLFLEALVDSV

AQGIPFQQHQFDKNVFQLEQAFVLSKQRYPSQPRGDTVDLAKKIFLKYY

PRWVAGSWGAPGGGGGAAAAAGGGGGGAPGGGGGAAAAAGGGGGAPGG

GGGAAAAAGGGGGAP<u>RGGRDHGDWDEASRLPPLPPREDAARVARFVTH</u>

<u>VSDWGALATISTLEAVRGRPFADVLSLSDGPPGAGSGVPYFYLSPLQLS</u>

<u>VSNLQENPYATLTMTLAQTNFCKKHGFPLCVHIMLSGTVTKV(N)ETEM</u>

<u>DIAKHSLFIRHPEMKTWPSSHNWFFAKL(N)ITNIWVLDYFGGPKIVTP</u>

<u>EEYY(N)VTVQ</u>

Human Full-Length Naglu—in italics
GAG3 Linker—in bold
CREG—underlined
Sites within CREG Sequence
 (N)—denotes glycosylation sites Naglu-IGFII The Naglu-IGFII protein is a fusion of Naglu and portions of the Insulin-like Growth Factor II peptide as described below. To create the Naglu-IGFII fusion protein, a nucleic acid construct was created by coupling the human Naglu gene to the sequence encoding the amino acid residues 8-67 (SEQ ID NO:22) of the Insulin-like Growth Factor II peptide IGFII). A GAG3 linker was inserted between the two sequences to allow for rotation between the two peptides following translation. In the resulting Full-Length Naglu-IGFII fusion protein (SEQ ID NO:21), Full-Length Naglu constitutes the N-terminus and the IGFII peptide sequences the C-terminus. Compared to the full-length IGFII molecule, 8-67 IGFII is reported to bind to M6P/IGF II receptor with a 2-10 fold higher affinity while its ability to bind to the IGF I receptor is decreased 30 fold (Hashimoto R, JBC 1995 270(30):18013-18018).

(SEQ ID NO: 21)
MEAVAVAAAVGVLLLAGAGGAAGDEAREAAAVRALVARLLGPGPAADFSV

SVERALAAKPGLDTYSLGGGGAARVRVRGSTGVAAAAGLHRYLRDFCGCH

VAWSGSQLRLPRPLPAVPGELTEATPNRYRYYQNVCTQSYSFVWWDWARW

EREIDWMALNGINLALAWSGQEAIWQRVYLALGLTQAEINEFFTGPAFLA

WGRMGNLHTWDGPLPPSWHIKQLYLQHRVLDQMRSFGMTPVLPAFAGHVP

EAVTRVFPQVNVTKMGSWGHFNCSYSCSFLLAPEDPIFPIIGSLFLRELI

KEFGTDHIYGADTFNEMQPPSSEPSYLAAATTAVYEAMTAVDTEAVWLLQ

GWLFQHQPQFWGPAQIRAVLGAVPRGRLLVLDLFAESQPVYTRTASFQGQ

PFIWCMLHNFGGNHGLFGALEAVNGGPEAARLFPNSTMVGTGMAPEGISQ

```
NEVVYSLMAELGWRKDPVPDLAAWVTSFAARRYGVSHPDAGAAWRLLLRS

VYNCSGEACRGHNRSPLVRRPSLQMNTSIWYNRSDVFEAWRLLLTSAPSL

ATSPAFRYDLLDLTRQAVQELVSLYYEEARSAYLSKELASLLRAGGVLAY

ELLPALDEVLASDSRFLLGSWLEQARAAAVSEAEADFYEQNSRYQLTLWG

PEGNILDYANKQLAGLVANYYTPRWRLFLEALVDSVAQGIPFQQHQFDKN

VFQLEQAFVLSKQRYPSQPRGDTVDLAKKIFLKYYPRWVAGSWGAPGGGG

GAAAAGGGGGAPGGGGAAAAAGGGGGAPGGGGGAAAAAGGGGGAP<ins>L</ins>

<ins>CGGELVDTLQFVCGDRGFYFSRPASRVSRRSRGIVEECCFRSCDLALLET</ins>

<ins>YCATPAKSE</ins>
```

Human Full-Length Naglu—in italics
GAG3 Linker—in bold
IGFII—underlined

```
                                        (SEQ ID NO: 22)
LCGGELVDTLQFVCGDRGFYFSRPASRVSRRSRGIVEECCFRSCDLALLE

TYCATPAKSE
```

SEQ ID NO:18-21 are the amino acid sequences of Full-Length Naglu fusion proteins, which still contain those 23 N-terminal amino acids of the Full-Length Naglu protein that are removed during intracellular processing. The amino acid sequences provided below (SEQ ID NO:23-26) are the corresponding sequences that do not include these 23 N-terminal amino acids.

Naglu-SapDC:

```
                                        (SEQ ID NO: 23)
DEAREAAAVRALVARLLGPGPAADFSVSVERALAAKPGLDTYSLGGGAA

RVRVRGSTGVAAAAGLHRYLRDFCGCHVAWSGSQLRLPRPLPAVPGELTE

ATPNRYRYYQNVCTQSYSFVWWDWARWEREIDWMALNGINLALAWSGQEA

IWQRVYLALGLTQAEINEFFTGPAFLAWGRMGNLHTWDGPLPPSWHIKQL

YLQHRVLDQMRSFGMTPVLPAFAGHVPEAVTRVFPQVNVTKMGSWGHFNC

SYSCSFLLAPEDPIFPIIGSLFLRELIKEFGTDHIYGADTFNEMQPPSSE

PSYLAAATTAVYEAMTAVDTEAVWLLQGWLFQHQPQFWGPAQIRAVLGAV

PRGRLLVLDLFAESQPVYTRTASFQGQPFIWCMLHNFGGNHGLFGALEAV

NGGPEAARLFPNSTMVGTGMAPEGISQNEVVYSLMAELGWRKDPVPDLAA

WVTSFAARRYGVSHPDAGAAWRLLLRSVYNCSGEACRGHNRSPLVRRPSL

QMNTSIWYNRSDVFEAWRLLLTSAPSLATSPAFRYDLLDLTRQAVQELVS

LYYEEARSAYLSKELASLLRAGGVLAYELLPALDEVLASDSRFLLGSWLE

QARAAAVSEAEADFYEQNSRYQLTLWGPEGNILDYANKQLAGLVANYYTP

RWRLFLEALVDSVAQGIPFQQHQFDKNVFQLEQAFVLSKQRYPSQPRGDT

VDLAKKIFLKYYPRWVAGSWGAPGGGGAAAAAGGGGGAPGGGGAAAA

AGGGGGGAPGGGGGAAAAAGGGGGAP<ins>DGGFCEVCKKLVGYLDRNLEK</ins>

<ins>(N)STKQEILAALEKGCSFLPDPYQKQCDQFVAEYEPVLIEILVEVMDPS</ins>

<ins>FVCLKIGACPSAHKPLLGTEKCIWGPSYWCQNTETAAQCNAVEHCKRHVW</ins>

<ins>N</ins>
```

Human Full length Naglu—in italics
GAG3 Linker—in bold
SapDC—underlined
Sites within SapDC Sequence
(N)—denotes glycosylation sites
Naglu-LIF:

```
                                        (SEQ ID NO: 24)
DEAREAAAVRALVARLLGPGPAADFSVSVERALAAKPGLDTYSLGGGGA

ARVRVRGSTGVAAAAGLHRYLRDFCGCHVAWSGSQLRLPRPLPAVPGEL

TEATPNRYRYYQNVCTQSYSFVWWDWARWEREIDWMALNGINLALAWSG

QEAIWQRVYLALGLTQAEINEFFTGPAFLAWGRMGNLHTWDGPLPPSWH

IKQLYLQHRVLDQMRSFGMTPVLPAFAGHVPEAVTRVFPQVNVTKMGSW

GHFNCSYSCSFLLAPEDPIFPIIGSLFLRELIKEFGTDHIYGADTFNEM

QPPSSEPSYLAAATTAVYEAMTAVDTEAVWLLQGWLFQHQPQFWGPAQI

RAVLGAVPRGRLLVLDLFAESQPVYTRTASFQGQPFIWCMLHNFGGNHG

LFGALEAVNGGPEAARLFPNSTMVGTGMAPEGISQNEVVYSLMAELGWR

KDPVPDLAAWVTSFAARRYGVSHPDAGAAWRLLLRSVYNCSGEACRGHN

RSPLVRRPSLQMNTSIWYNRSDVFEAWRLLLTSAPSLATSPAFRYDLLD

LTRQAVQELVSLYYEEARSAYLSKELASLLRAGGVLAYELLPALDEVLA

SDSRFLLGSWLEQARAAAVSEAEADFYEQNSRYQLTLWGPEGNILDYAN

KQLAGLVANYYTPRWRLFLEALVDSVAQGIPFQQHQFDKNVFQLEQAFV

LSKQRYPSQPRGDTVDLAKKIFLKYYPRWVAGSWGAPGGGGAAAAAGG

GGGGAPGGGGAAAAAGGGGGAPGGGGAAAAAGGGGGAP<ins>SPLPITP</ins>

<ins>VNATCAIRHPCHNNLMN{A}IR{A}QLA{A}L(N)GSANALFILYYTAQ</ins>

<ins>GEPFPNNLDKLCGP(N)VTDFPPFHA(N)GTEKAKLVELYRIVVYLGTS</ins>

<ins>LG(N)ITRDQKILNPSALSLHSKL(N)ATADILRGLLSNVLCRLCSKYH</ins>

<ins>VGHVDVTYGPDTSGKDV[[A]]QK[[A]]KLGCQLLGKYKQIIAVLAQA</ins>

<ins>F</ins>
```

Human Full-Length Naglu—in italics
GAG3 Linker—in bold
LIF—underlined
Sites within LIF Sequence
(N)—denotes glycosylation sites
{ }—denotes mutations made to alter recognition of the receptor gp130; [[ ]]—denotes mutations made to alter recognition of the LIF receptor
Naglu-CREG:

```
                                        (SEQ ID NO: 25)
DEAREAAAVRALVARLLGPGPAADFSVSVERALAAKPGLDTYSLGGGGA

ARVRVRGSTGVAAAAGLHRYLRDFCGCHVAWSGSQLRLPRPLPAVPGEL

TEATPNRYRYYQNVCTQSYSFVWWDWARWEREIDWMALNGINLALAWSG

QEAIWQRVYLALGLTQAEINEFFTGPAFLAWGRMGNLHTWDGPLPPSWH

IKQLYLQHRVLDQMRSFGMTPVLPAFAGHVPEAVTRVFPQVNVTKMGSW

GHFNCSYSCSFLLAPEDPIFPIIGSLFLRELIKEFGTDHIYGADTFNEM

QPPSSEPSYLAAATTAVYEAMTAVDTEAVWLLQGWLFQHQPQFWGPAQI

RAVLGAVPRGRLLVLDLFAESQPVYTRTASFQGQPFIWCMLHNFGGNHG
```

-continued

LFGALEAVNGGPEAARLFPNSTMVGTGMAPEGISQNEVVYSLMAELGWR

KDPVPDLAAWVTSFAARRYGVSHPDAGAAWRLLLRSVYNCSGEACRGHN

RSPLVRRPSLQMNTSIWYNRSDVFEAWRLLLTSAPSLATSPAFRYDLLD

LTRQAVQELVSLYYEEARSAYLSKELASLLRAGGVLAYELLPALDEVLA

SDSRFLLGSWLEQARAAAVSEAEADFYEQNSRYQLTLWGPEGNILDYAN

KQLAGLVANYYTPRWRLFLEALVDSVAQGIPFQQHQFDKNVFQLEQAFV

LSKQRYPSQPRGDTVDLAKKIFLKYYPRWVAGSWGAPGGGGAAAAAGG

GGGGAPGGGGGAAAAAGGGGGGAPGGGGGAAAAAGGGGGGAPRGGRDHG

DWDEASRLPPLPPREDAARVARFVTHVSDWGALATISTLEAVRGRPFAD

VLSLSDGPPGAGSGVPYFYLSPLQLSVSNLQENPYATLTMTLAQTNFCK

KHGFPLCVHIMLSGTVTKV(N)ETEMDIAKHSLFIRHPEMKTWPSSHNW

FFAKL(N)ITNIWVLDYFGGPKIVTPEEYY(N)VTVQ

Human Full-Length Naglu—in italics
GAG3 Linker—in bold
CREG—underlined
Sites within CREG Sequence
    (N)—denotes glycosylation sites
    Naglu-IGFII:

(SEQ ID NO: 26)
DEAREAAAVRALVARLLGPGPAADFSVSVERALAAKPGLDTYSLGGGGA

ARVRVRGSTGVAAAAGLHRYLRDFCGCHVAWSGSQLRLPRPLPAVPGEL

TEATPNRYRYYQNVCTQSYSFVWWDWARWEREIDWMALNGINLALAWSG

QEAIWQRVYLALGLTQAEINEFFTGPAFLAWGRMGNLHTWDGPLPPSWH

IKQLYLQHRVLDQMRSFGMTPVLPAFAGHVPEAVTRVFPQVNVTKMGSW

GHFNCSYSCSFLLAPEDPIFPIIGSLFLRELIKEFGTDHIYGADTFNEM

QPPSSEPSYLAAATTAVYEAMTAVDTEAVWLLQGWLFQHQPQFWGPAQI

RAVLGAVPRGRLLVLDLFAESQPVYTRTASFQGQPFIWCMLHNFGGNHG

LFGALEAVNGGPEAARLFPNSTMVGTGMAPEGISQNEVVYSLMAELGWR

KDPVPDLAAWVTSFAARRYGVSHPDAGAAWRLLLRSVYNCSGEACRGHN

RSPLVRRPSLQMNTSIWYNRSDVFEAWRLLLTSAPSLATSPAFRYDLLD

LTRQAVQELVSLYYEEARSAYLSKELASLLRAGGVLAYELLPALDEVLA

SDSRFLLGSWLEQARAAAVSEAEADFYEQNSRYQLTLWGPEGNILDYAN

KQLAGLVANYYTPRWRLFLEALVDSVAQGIPFQQHQFDKNVFQLEQAFV

LSKQRYPSQPRGDTVDLAKKIFLKYYPRWVAGSWGAPGGGGAAAAAGG

GGGGAPGGGGGAAAAAGGGGGGAPGGGGGAAAAAGGGGGGAPLCGGELV

DTLQFVCGDRGFYFSRPASRVSRRSRGIVEECCFRSCDLALLETYCATP

AKSE

Human Full-Length Naglu—in italics
GAG3 Linker—in bold
IGFII—underlined

Example 2: In Vitro M6P Receptor Binding and Cellular Uptake of Naglu-Fusion Proteins The nucleic acid encoding each of the different Naglu fusion proteins was subcloned into a mammalian expression vector and transfected into HT-1080 cells using standard technologies. Transfectants were then screened to generate a HT-1080 overexpressing cell line, using technologies generally known in the art. For all in vitro protein based assays and receptor binding experiments, recombinant protein was produced in a wave bioreactor, using a mammalian cell culture expressing system. Following expression, each fusion protein was subjected to a three step purification process. First, the conditioned media was concentrated using an ultra-filtration (UF) device (Pall Corporation, Port Washington, N.Y. 11050). The concentrated media was then applied to a butyl sepharose chromatography column (Butyl), and the eluate of this purification step was then further purified using a Q sepharose chromatography column (Q). The purified protein was buffer exchanged into PBS (11.9 mM sodium phosphate, 2.7 mM potassium phosphate, 137 mM sodium chloride at pH 7.4) for storage. The resulting fusion proteins were purified to greater than 90% purity.

Figure 2:
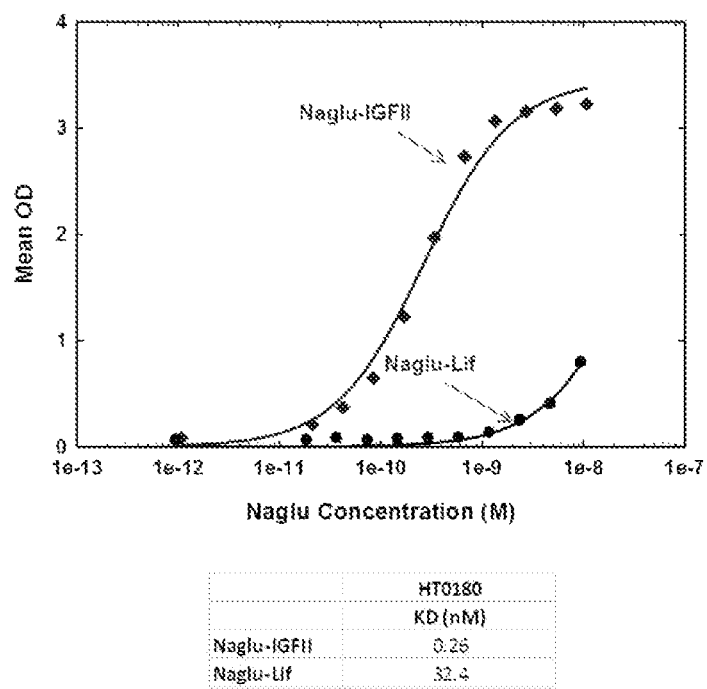
FIG. 2 shows an M6P receptor in vitro binding assay for Naglu-IGFII and Naglu-LIF fusion proteins.

Following purification, ELISAs was performed with various concentrations of fusion proteins and with an antibody directed to human Naglu to evaluate the binding of the Naglu-fusion proteins to CI-M6PR. The data demonstrate that the Naglu-IGFII, Naglu-CREG, Naglu-SapDC and Naglu-LIF fusion proteins were able to bind to CI-M6PR (FIGS. 1 and 2). Of the four fusion proteins, Naglu-IGFII showed the strongest binding with a $K_D$ of approximately 0.21 nM. Naglu-CREG, Naglu-SapDC and Naglu LIF also showed strong binding to CI-M6PR ($K_D$ of 1.25, 5.5 and 32.4 nM, respectively), which was not as strong as the the binding by Naglu-IGFII however (FIGS. 1 and 2).

Figure 3:
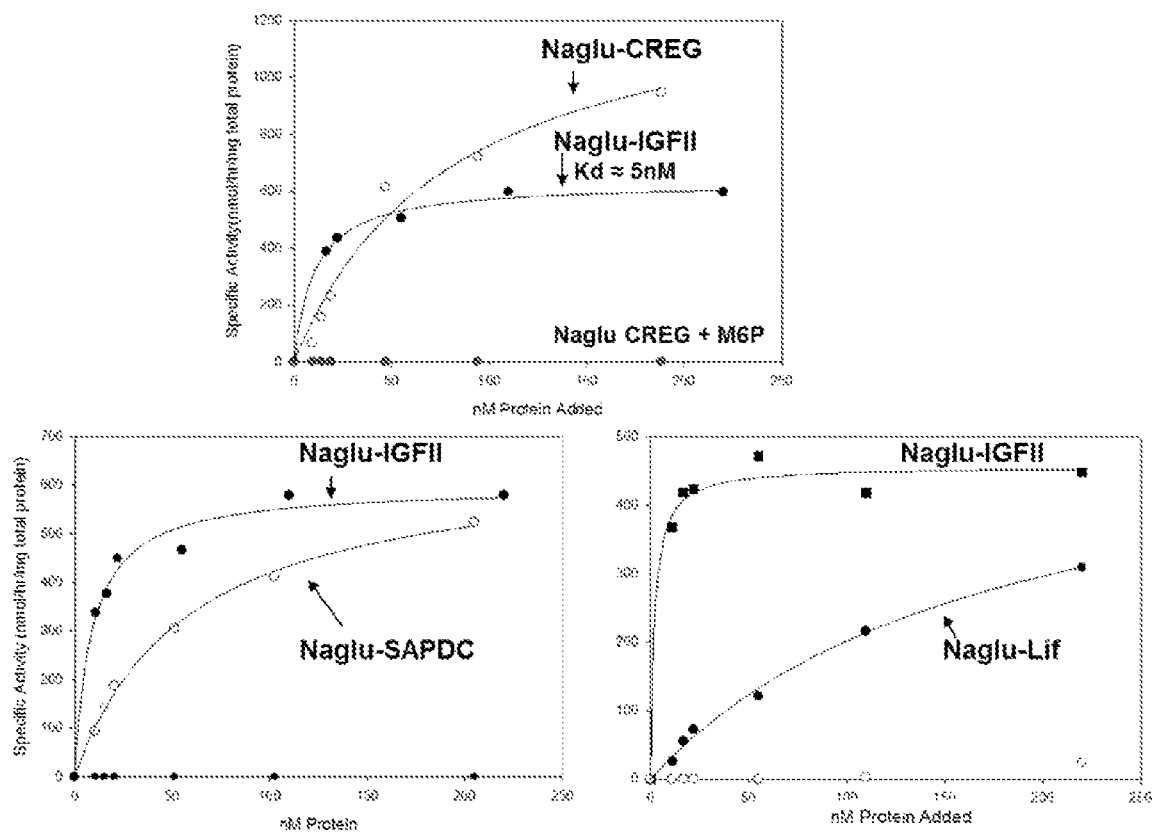
FIG. 3 shows results of an in vitro assay monitoring M6P-receptor mediated cellular uptake of Naglu-CREG, Naglu-SapDC and Naglu-LIF fusion proteins and comparison to the cellular uptake of Naglu-IGFII determined by the same assay.

In vitro CI-M6PR mediated targeting and cellular uptake of each Naglu-fusion protein was also evaluated. Briefly, cells overexpressing CI-M6PR were grown to confluence and treated with a solution of recombinant Naglu-IGFII, Naglu-CREG, Naglu-SapDC or Naglu-LIF at various concentrations, which contained additional mannose-6-phosphate or not (FIG. 3). After a specified period of time, the supernatant was removed and the cells were washed repeatedly. Following lysis of the cells, each sample was assayed for intracellular Naglu enzyme activity. The data indicate that, following treatment with each fusion protein, there was an increase in the level of intracellular Naglu activity, suggesting that all four fusion proteins were effectively internalized by the cells (FIG. 3). This was in stark contrast to incubation of the Naglu-fusion protein in the presence of mannose-6-phosphate, which completely blocked cellular internalization (FIG. 3). The ability of mannose-6-phosphate to prevent CI-M6PR targeting and lysosomal entry of each Naglu-fusion protein (Naglu-CREG, Naglu-SapDC and Naglu-LIF) suggests that mannose-6-phosphate is able to effectively outcompete Naglu-fusion protein binding to CI-M6PR. This demonstrates that the observed cellular internalization and lysosomal entry of each Naglu-fusion protein was the result of CI-M6PR. The data also indicate that cellular uptake of the Naglu-fusion proteins occurs in a dose dependent fashion since intracellular Naglu activity increased in proportion to increasing concentrations of Naglu-fusion protein added to the assay (FIG. 3) Binding of Naglu-IGFII to CI-M6PR is mediated through a protein-protein interaction between the IGF-II domain and CI-M6PR. Cellular uptake of Naglu-IGFII is therefore not dependent on mannose-6-phosphate and not outcompeted by it.

Example 3: Creation of GNPT Cell Lines

Given the critical role GNPT plays in the post-translation modification of N-linked glycans, specifically the M6P- phosphorylation of soluble lysosomal enzymes, experiments were performed to evaluate if overexpression of the GNPT enzyme could result in increased M6P-phosphorylation levels on lysosomal emzymes.

N-acetylglucosamine-1-phosphotransferase (GNTP) protein is a hexameric complex containing two copies each of three distinct subunits (α, β, γ). The nucleic acid encoding the alpha/beta subunits and the gamma subunit of the GNTP protein were cloned into one mammalian expression vector containing an expression cassette for the alpha/beta subunit and one expression cassette for the gamma subunit. The vector was transfected into human HT-1080 cells, which were then grown under selection pressure to establish cell lines overexpressing recombinant GNTP. A cell line overexpressing GNPT was selected and used for secondary transfection with a mammalian expression vector expressing Naglu-LIF, Naglu-CREG, Naglu-SapDC or Naglu-IGFII, or the native form of one of various lysosomal storage disease enzymes (ARSA, I2S, HNS, GAA, GCB). Overexpression of GNTP and of each co-expression product was confirmed by qPCR, ELISA, lysosomal enzyme activity assay and/or Western blot analysis.

The GNPT enzyme exists as a hexameric protein complex containing two copies each of three distinct subunits (α, β, γ). One construct was generated containing two expression cassettes, one encoding the alpha/beta subunits and a second one encoding the gamma subunit.

GNTP Alpha/Beta

To facilitate expression of the alpha and beta subunits of GNPT a nucleic acid construct was created using the nucleic acid sequence of SEQ ID NO:27.

```
(SEQ ID NO: 27)
ATGCTGTTCAAGCTCCTGCAGAGACAGACCTATACCTGCCTGTCCCACA

GGTATGGGCTCTACGTGTGCTTCTTGGGCGTCGTTGTCACCATCGTCTC

CGCCTTCCAGTTCGGAGAGGTGGTTCTGGAATGGAGCCGAGATCAATAC

CATGTTTTGTTTGATTCCTATAGAGACAATATTGCTGGAAAGTCCTTTC

AGAATCGGCTTTGTCTGCCCATGCCGATTGACGTTGTTTACACCTGGGT

GAATGGCACAGATCTTGAACTACTGAAGGAACTACAGCAGGTCAGAGAA

CAGATGGAGGAGGAGCAGAAAGCAATGAGAGAAATCCTTGGGAAAAACA

CAACGGAACCTACTAAGAAGAGTGAGAAGCAGTTAGAGTGTTTGCTAAC

ACACTGCATTAAGGTGCCAATGCTTGTCCTGGACCCAGCCCTGCCAGCC

AACATCACCCTGAAGGACCTGCCATCTCTTTATCCTTCTTTTCATTCTG

CCAGTGACATTTTCAATGTTGCAAAACCAAAAAACCCTTCTACCAATGT

CTCAGTTGTTGTTTTTGACAGTACTAAGGATGTTGAAGATGCCCACTCT

GGACTGCTTAAAGGAAATAGCAGACAGACAGTATGGAGGGGCTACTTGA

CAACAGATAAAGAAGTCCCTGGATTAGTGCTAATGCAAGATTTGGCTTT

CCTGAGTGGATTTCCACCAACATTCAAGGAAACAAATCAACTAAAAACA

AAATTGCCAGAAAATCTTTCCTCTAAAGTCAAACTGTTGCAGTTGTATT

CAGAGGCCAGTGTAGCGCTTCTAAAACTGAATAACCCCAAGGATTTTCA

AGAATTGAATAAGCAAACTAAGAAGAACATGACCATTGATGGAAAAGAA

CTGACCATAAGTCCTGCATATTTATTATGGGATCTGAGCGCCATCAGCC

AGTCTAAGCAGGATGAAGACATCTCTGCCAGTCGTTTTGAAGATAACGA

AGAACTGAGGTACTCATTGCGATCTATCGAGAGGCATGCACCATGGGTT

CGGAATATTTTCATTGTCACCAACGGGCAGATTCCATCCTGGCTGAACC

TTGACAATCCTCGAGTGACAATAGTAACACACCAGGATGTTTTTCGAAA

TTTGAGCCACTTGCCTACCTTTAGTTCACCTGCTATTGAAAGTCACATT

CATCGCATCGAAGGGCTGTCCCAGAAGTTTATTTACCTAAATGATGATG

TCATGTTTGGGAAGGATGTCTGGCCAGATGATTTTTACAGTCACTCCAA

AGGCCAGAAGGTTTATTTGACATGGCCTGTGCCAAACTGTGCCGAGGGC

TGCCCAGGTTCCTGGATTAAGGATGGCTATTGTGACAAGGCTTGTAATA

ATTCAGCCTGCGATTGGGATGGTGGGGATTGCTCTGGAAACAGTGGAGG

GAGTCGCTATATTGCAGGAGGTGGAGGTACTGGGAGTATTGGAGTTGGA

CAGCCCTGGCAGTTTGGTGGAGGAATAAACAGTGTCTCTTACTGTAATC

AGGGATGTGCGAATTCCTGGCTCGCTGATAAGTTCTGTGACCAAGCATG

CAATGTCTTGTCCTGTGGGTTTGATGCTGGCGACTGTGGGCAAGATCAT

TTTCATGAATTGTATAAAGTGATCCTTCTCCCAAACCAGACTCACTATA

TTATTCCAAAAGGTGAATGCCTGCCTTATTTCAGCTTTGCAGAAGTAGC

CAAAAGAGGAGTTGAAGGTGCCTATAGTGACAATCCAATAATTCGACAT

GCTTCTATTGCCAACAAGTGGAAAACCATCCACCTCATAATGCACAGTG

GAATGAATGCCACCACAATACATTTTAATCTCACGTTTCAAAATACAAA

CGATGAAGAGTTCAAAATGCAGATAACAGTGGAGGTGGACACAAGGGAG

GGACCAAAACTGAATTCTACAGCCCAGAAGGGTTACGAAAATTTAGTTA

GTCCCATAACACTTCTTCCAGAGGCGGAAATCCTTTTTGAGGATATTCC

CAAAGAAAACGCTTCCCGAAGTTTAAGAGACATGATGTTAACTCAACA

AGGAGAGCCCAGGAAGAGGTGAAAATTCCCCTGGTAAATATTTCACTCC

TTCCAAAAGACGCCCAGTTGAGTCTCAATACCTTGGATTTGCAACTGGA

ACATGGAGACATCACTTTGAAAGGATACAATTTGTCCAAGTCAGCCTTG

CTGAGATCATTTCTGATGAACTCACAGCATGCTAAAATAAAAAATCAAG

CTATAATAACAGATGAAACAAATGACAGTTTGGTGGCTCCACAGGAAAA

ACAGGTTCATAAAAGCATCTTGCCAAACAGCTTAGGAGTGTCTGAAAGA

TTGCAGAGGTTGACTTTTCCTGCAGTGAGTGTAAAAGTGAATGGTCATG

ACCAGGGTCAGAATCCACCCCTGGACTTGGAGACCACAGCAAGATTTAG

AGTGGAAACTCACACCCAAAAAACCATAGGCGGAAATGTGACAAAAGAA

AAGCCCCCATCTCTGATTGTTCCACTGGAAAGCCAGATGACAAAAGAAA

AGAAAATCACAGGGAAAGAAAAAGAGAACAGTAGAATGGAGGAAAATGC

TGAAAATCACATAGGCGTTACTGAAGTGTTACTTGGAAGAAAGCTGCAG

CATTACACAGATAGTTACTTGGGCTTTTTGCCATGGGAGAAAAAAAAGT

ATTTCCAAGATCTTCTCGACGAAGAAGAGTCATTGAAGACACAATTGGC

ATACTTCACTGATAGCAAAAATACTGGGAGGCAACTAAAAGATACATTT

GCAGATTCCCTCAGATATGTAAATAAAATTCTAAATAGCAAGTTTGGAT

TCACATCGCGGAAAGTCCCTGCTCACATGCCTCACATGATTGACCGGAT

TGTTATGCAAGAACTGCAAGATATGTTCCCTGAAGAATTTGACAAGACG

TCATTTCACAAAGTGCGCCATTCTGAGGATATGCAGTTTGCCTTCTCTT
```

-continued

```
ATTTTTATTATCTCATGAGTGCAGTGCAGCCACTGAATATATCTCAAGT
CTTTGATGAAGTTGATACAGATCAATCTGGTGTCTTGTCTGACAGAGAA
ATCCGAACACTGGCTACCAGAATTCACGAACTGCCGTTAAGTTTGCAGG
ATTTGACAGGTCTGGAACACATGCTAATAAATTGCTCAAAAATGCTTCC
TGCTGATATCACGCAGCTAAATAATATTCCACCAACTCAGGAATCCTAC
TATGATCCCAACCTGCCACCGGTCACTAAAAGTCTAGTAACAAACTGTA
AACCAGTAACTGACAAAATCCACAAAGCATATAAGGACAAAAACAAATA
TAGGTTTGAAATCATGGGAGAAGAAGAAATCGCTTTTAAAATGATTCGT
ACCAACGTTTCTCATGTGGTTGGCCAGTTGGATGACATAAGAAAAAACC
CTAGGAAGTTTGTTTGCCTGAATGACAACATTGACCACAATCATAAAGA
TGCTCAGACAGTGAAGGCTGTTCTCAGGGACTTCTATGAATCCATGTTC
CCCATACCTTCCCAATTTGAACTGCCAAGAGAGTATCGAAACCGTTTCC
TTCATATGCATGAGCTGCAGGAATGGAGGGCTTATCGAGACAAATTGAA
GTTTTGGACCCATTGTGTACTAGCAACATTGATTATGTTTACTATATTC
TCATTTTTTGCTGAGCAGTTAATTGCACTTAAGCGGAAGATATTTCCCA
GAAGGAGGATACACAAAGAAGCTAGTCCCAATCGAATCAGAGTATAG
```

The resulting amino acid sequence (SEQ ID NO:28) included the alpha and beta subunits of GNPT along with the required cleavage recognition site.

```
                                          (SEQ ID NO: 28)
MLFKLLQRQTYTCLSHRYGLYVCFLGVVVTIVSAFQFGEVVLEWSRDQY
HVLFDSYRDNIAGKSFQNRLCLPMPIDVVYTWVNGTDLELLKELQQVRE
QMEEEQKAMREILGKNTTEPTKKSEKQLECLLTHCIKVPMLVLDPALPA
NITLKDLPSLYPSFHSASDIFNVAKPKNPSTNVSVVVFDSTKDVEDAHS
GLLKGNSRQTVWRGYLTTDKEVPGLVLMQDLAFLSGFPPTFKETNQLKT
KLPENLSSKVKLLQLYSEASVALLKLNNPKDFQELNKQTKKNMTIDGKE
LTISPAYLLWDLSAISQSKQDEDISASRFEDNEELRYSLRSIERHAPWV
RNIFIVTNGQIPSWLNLDNPRVTIVTHQDVFRNLSHLPTFSSPAIESHI
HRIEGLSQKFIYLNDDVMFGKDVWPDDFYSHSKGQKVYLTWPVPNCAEG
CPGSWIKDGYCDKACNNSACDWDGGDCSGNSGGSRYIAGGGGTGSIGVG
QPWQFGGGINSVSYCNQGCANSWLADKFCDQACNVLSCGFDAGDCGQDH
FHELYKVILLPNQTHYIIPKGECLPYFSFAEVAKRGVEGAYSDNPIIRH
ASIANKWKTIHLIMHSGMNATTIHFNLTFQNTNDEEFKMQITVEVDTRE
GPKLNSTAQKGYENLVSPITLLPEAEILFEDIPKEKRFPKFKRHDVNST
RRAQEEVKIPLVNISLLPKDAQLSLNTLDLQLEHGDITLKGYNLSKSAL
LRSFLMNSQHAKIKNQAIITDETNDSLVAPQEKQVHKSILPNSLGVSER
LQRLTFPAVSVKVNGHDQGQNPPLDLETTARFRVETHTQKTIGGNVTKE
KPPSLIVPLESQMTKEKKITGKEKENSRMEENAENHIGVTEVLLGRKLQ
HYTDSYLGFLPWEKKKYFQDLLDEEESLKTQLAYFTDSKNTGRQLKDTF
ADSLRYVNKILNSKFGFTSRKVPAHMPHMIDRIVMQELQDMFPEEFDKT
SFHKVRHSEDMQFAFSYFYYLMSAVQPLNISQVFDEVDTDQSGVLSDRE
IRTLATRIHELPLSLQDLTGLEHMLINCSKMLPADITQLNNIPPTQESY
YDPNLPPVTKSLVTNCKPVTDKIHKAYKDKNKYRFEIMGEEEIAFKMIR
TNVSHVVGQLDDIRKNPRKFVCLNDNIDHNHKDAQTVKAVLRDFYESMF
PIPSQFELPREYRNRFLHMHELQEWRAYRDKLKFWTHCVLATLIMFTIF
SFFAEQLIALKRKIFPRRRIHKRASPNRIRV
```

*Alpha/Beta cleavage recognition site—in bold and underlined

GNPT Gamma

To facilitate expression of the gamma subunit of GNPT a nucleic acid construct was created using the nucleic acid sequence of SEQ ID NO:29.

```
                                          (SEQ ID NO: 29)
ATGGCGGCGGGGCTGGCGCGGCTCCTGTTGCTCCTCGGGCTCTCGGCCG
GCGGGCCCGCGCCGGCAGGTGCAGCGAAGATGAAGGTGGTGGAGGAGCC
CAACGCGTTTGGGGTGAACAACCCGTTCTTGCCTCAGGCCAGTCGCCTC
CAGGCCAAGAGGGATCCTTCACCCGTGTCTGGACCCGTGCATCTCTTCC
GACTCTCGGGCAAGTGCTTCAGCCTGGTGGAGTCCACGTACAAGTATGA
GTTCTGCCCGTTCCACAACGTGACCCAGCACGAGCAGACCTTCCGCTGG
AACGCCTACAGTGGGATCCTCGGCATCTGGCACGAGTGGGAGATCGCCA
ACAACACCTTCACGGGCATGTGGATGAGGGACGGTGACGCCTGCCGTTC
CCGGAGCCGGCAGAGCAAGGTGGAGCTGGCGTGTGGAAAAAGCAACCGG
CTGGCCCATGTGTCCGAGCCGAGCACCTGCGTCTACGCGCTGACGTTCG
AGACCCCCCTCGTCTGCCACCCCCACGCCTTGCTAGTGTACCCAACCCT
GCCAGAGGCCCTGCAGCGGCAGTGGGACCAGGTAGAGCAGGACCTGGCC
GATGAGCTGATCACCCCCCAGGGCCATGAGAAGTTGCTGAGGACACTTT
TTGAGGATGCTGGCTACTTAAAGACCCCAGAAGAAAATGAACCCACCCA
GCTGGAGGGAGGTCCTGACAGCTTGGGGTTTGAGACCCTGGAAAACTGC
AGGAAGGCTCATAAAGAACTCTCAAAGGAGATCAAAAGGCTGAAAGGTT
TGCTCACCCAGCACGGCATCCCCTACACGAGGCCCACAGAAACTTCCAA
CTTGGAGCACTTGGGCCACGAGACGCCCAGAGCCAAGTCTCCAGAGCAG
CTGCGGGGTGACCCAGGACTGCGTGGGAGTTTGTGA
```

The resulting amino acid sequence (SEQ ID NO:30) included the gamma subunit of GNPT.

```
                                          (SEQ ID NO: 30)
MAAGLARLLLLLGLSAGGPAPAGAAKMKVVEEPNAFGVNNPFLPQASRLQ
AKRDPSPVSGPVHLFRLSGKCFSLVESTYKYEFCPFHNVTQHEQTFRWNA
YSGILGIWHEWEIANNTFTGMWMRDGDACRSRSRQSKVELACGKSNRLAH
VSEPSTCVYALTFETPLVCHPHALLVYPTLPEALQRQWDQVEQDLADELI
TPQGHEKLLRTLFEDAGYLKTPEENEPTQLEGGPDSLGFETLENCRKAHK
ELSKEIKRLKGLLTQHGIPYTRPTETSNLEHLGHETPRAKSPEQLRGDPG
LRGSL
```

Example 4: Evaluation of Lysosomal Enzymes Produced in a GNPT Cell Line

Figure 4:
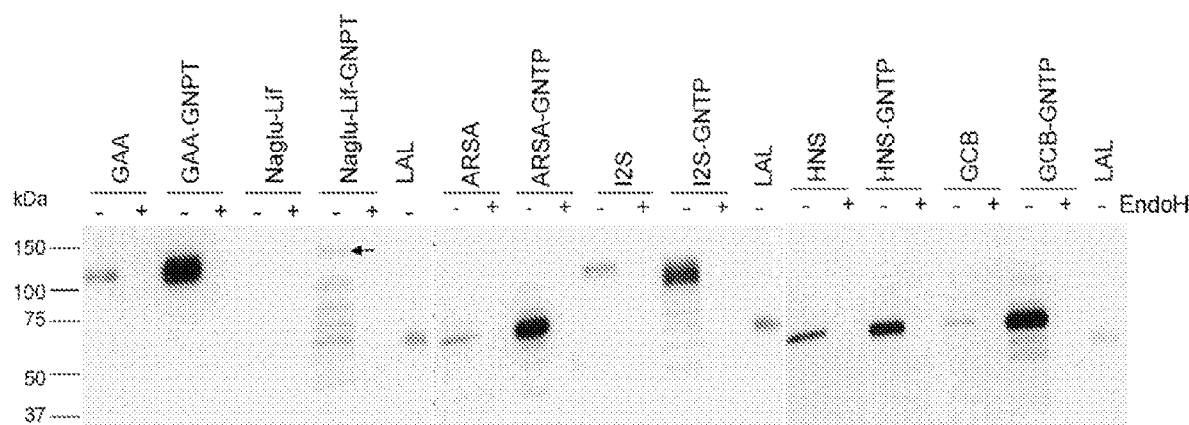
FIG. 4 shows Western blot analysis using an anti-M6P antibody to show the relative content of M6P of acid alpha-glucosidase (GAA); Naglu-LIF fusion protein (Naglu-LIF); arylsulfatase A (ARSA); iduronate 2-sulfatase (I2S); heparan-N-sulfamidase (HNS); and glucocerebrosidase (GCB) protein produced in wild-type HT1080 cells or an N-acetylgucosamine-1-phosphotransferase (GNPT) overexpressing cell line. Western blot analysis was conducted before (−) and after (+) removal of M6P using endoglycosidase H.

Given the critical role GNPT plays in the post-translation modification of N-linked glycans, specifically the M6P-phosphorylation of soluble lysosomal enzymes, experiments were performed to evaluate if overexpression of the GNPT enzyme could result in increased M6P-phosphorylation levels on lysosomal emzymes. Briefly, recombinant HT-1080 cell lines, overexpressing a single lysosomal enzyme (GAA, LAL, ARSA, I2S, HNS or GCB) or co-overexpressing a lysosomal enzyme and GNPT (GAA-GNPT, ARSA-GNPT, I2S-GNPT, HNS-GNPT or GCB-GNPT) were generated using standard methodologies. Similar cell lines were generated overexpressing only Naglu-LIF (Naglu-LIF) or Naglu-LIF and GNPT (Naglu-LIF-GNPT). Each of the cell lines was grown to confluence and conditioned cell medium was collected and concentrated as described. For control purposes, fractions of the concentrated sample were then treated with Endoglycosidase H, and treated and untreated samples were separated by SDS-PAGE (proteins were quantified by ELISA or an enzymatic activity assay and 250 ng of each lysosomal enzyme were loaded) and analyzed by Western blotting using an anti-M6P antibody. As shown in FIG. 4, co-expression of each lysosomal enzyme with GNPT resulted in a dramatic increase in M6P phosphorylation signal, compared to expression of lysosomal enzymes alone. Surprisingly, while Naglu-LIF protein overexpressed alone is not M6P-phosphorylated in any detectable manner, co-expression of Naglu-LIF with GNPT resulted in increased M6P-phosporylation (FIG. 4).

These data indicate that it is possible to use fusion proteins and/or co-expression of GNPT to increase M6P-phosporylation of lysosomal enzymes (e.g., Naglu).

Figure 5:
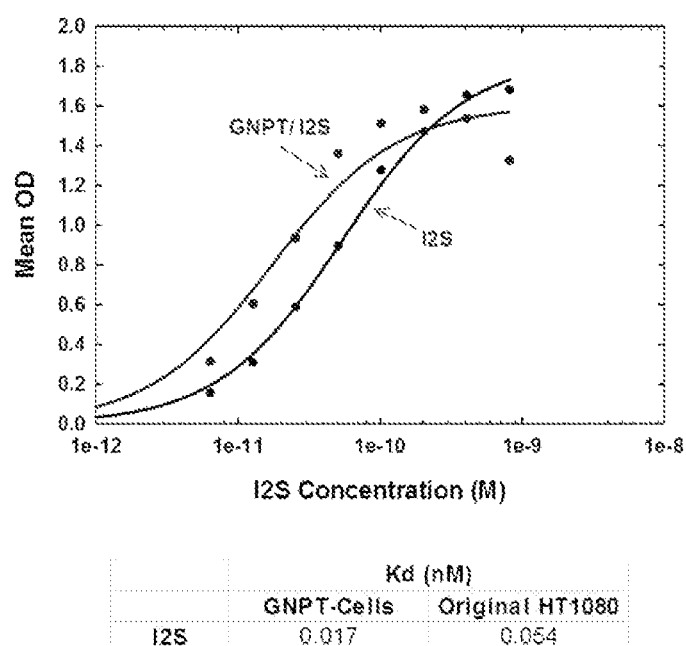
FIG. 5 demonstrates in vitro binding of iduronate 2-sulfatase (I2S) binding to the M6P receptor when produced in wild-type HT1080 cells or an N-acetylgucosamine-1-phosphoTransferase (GNPT) overexpressing cell line.

Example 5: Increased M6P Receptor Binding and Cellular Uptake of Recombinant I2S Produced Using a GNPT Cell Line To further evaluate if expression of recombinant lysosomal proteins in a GNPT overexpressing cell line results in increased M6P-phosphorylation, additional studies were performed regarding the lysosomal enzyme I2S. Recombinant HT-1080 cell lines overexpressing I2S alone or co-overexpressing I2S and GNPT were generated using standard methodologies. Each of the cell lines was grown to confluence and conditioned cell medium was collected and concentrated as described. Each protein was tested for any change in receptor affinity using the CI-M6PR binding assay described in Example 4. This analysis revealed that I2S from cells overexpressing this protein alone bound to CI-M6PR more weakly than I2S from cells also overexpressing GNPT (FIG. 5).

Figure 6:
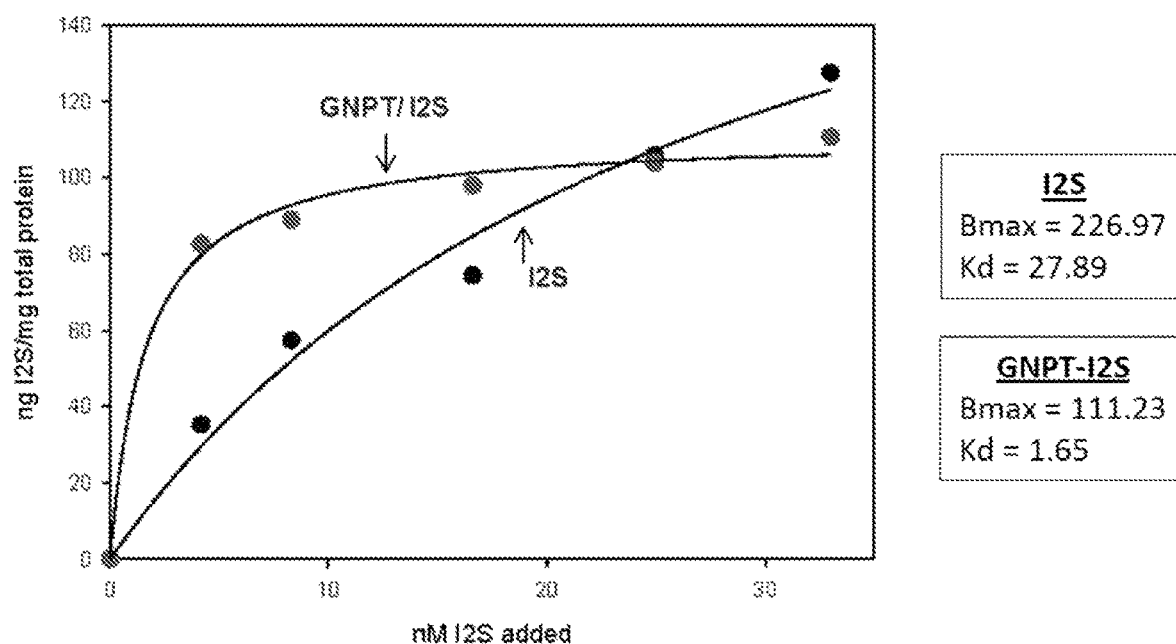
FIG. 6 illustrates the in vitro cellular uptake of iduronate 2-sulfatase (I2S) produced in wild-type HT1080 cells or an N-acetylgucosamine-1-phosphoTransferase (GNPT) overexpressing cell line.

In vitro M6P receptor mediated targeting and cellular uptake of recombinantly produced I2S proteins was also evaluated. Briefly, cells overexpressing CI-M6PR were grown to confluence and treated with a solution of recombinant I2S produced in HT-1080 cells only overexpressing this protein, or recombinant I2S produced in HT-1080 cells also overexpressing GNPT. After a specified period of time, the supernatant was removed and the cells were washed repeatedly. Following lysis, each cell sample was assayed for intracellular I2S enzyme activity. The data demonstrate that I2S produced in GNPT overexpressing cell line was internalized more quickly and displayed a higher affinity ($K_D$=1.65 nM) for CI-M6PR than I2S produced in cells overexpressing I2S alone ($K_D$=27.89 nM) (FIG. 6). Taken together, this increase in cellular uptake is consistent with both the observed increased M6P-phosphorylation (FIG. 4) and tighter receptor binding (FIG. 5), suggesting that enhanced CI-M6PR-mediated cellular uptake by the cell is the result of increased M6P-phosphorylation and CI-M6PR binding affinity.

Example 6: Increased M6P Receptor Binding of Native and Naglu-Fusion Proteins Produced Using a GNPT Cell Line As described above, the level of M6P-phosphorylation of recombinantly produced therapeutic glycoproteins could be increased by using GNPT overexpressing cell lines (FIG. 4). In particular, an increase in M6P-phosphorylation was observed for the therapeutic fusion glycoprotein Naglu-LIF (FIG. 4). Surprisingly, this increase in M6P-phosphorylation of the Naglu protein when fused to LIF, produced a level of M6P-phosphorylation which was not observed for the native Naglu protein, or with respect to non-fusion rhNaglu generated in cells not co-overexpressing GNPT. To further evaluate this phenomenon, additional studies were conducted to evaluate M6P-phosphorylation levels for rhNaglu and various fusion proteins recombinantly produced using GNPT overexpressing cell lines. Briefly, clonal HT-1080 cell lines expressing a single recombinant protein (Naglu-IGFII, rhNaglu, Naglu-CREG or Naglu-SapDC) or co-expressing a lysosomal enzyme and GNPT (GNPT/Naglu-SapDC, GNPT/Naglu-CREG, GNPT/rhNaglu) were generated using standard procedures. Each cell line was grown to confluence, conditioned medium was collected and the respective lysosomal protein and/or fusion protein was purified to greater than 90% purity.

Figure 7:
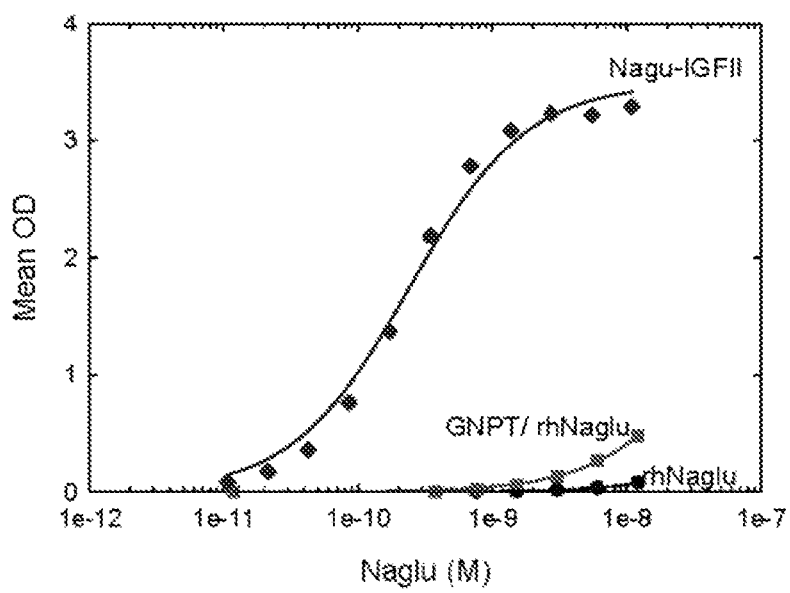
FIG. 7 shows the in vitro M6P receptor binding of recombinant Naglu proteins produced in HT1080 cells or a GNPT overexpressing cell line (GlcNAc-P-T).

For the initial study, an in vitro assay was used to evaluate CI-M6PR binding. This analysis revealed that overexpression of rhNaglu alone resulted in an extremely low binding affinity for CI-M6PR, with a $K_d$ below the assay's detection threshold (FIG. 7). This result is in accordance with our previous findings, which demonstrated little to no M6P-phosphorylation of the rhNaglu enzyme when generated by overexpression in HT-1080 cells. By contrast, rhNaglu produced using a GNPT overexpressing cell line demonstrated, for the first time, a weak binding affinity for CI-M6PR with a $K_d$ value of approximately 65 nM (FIG. 7). While this binding affinity is much lower than the binding affinity of Naglu-IGFII (used as a positive control) (FIG. 7), binding of the latter is mediated through a protein-protein interaction between the IGF-II domain and CI-M6PR. Thus, our data indicate that the low M6P-phosphorylation levels of certain therapeutic glycoproteins, such as Naglu, can be enhanced by the manufacture of these proteins in GNPT overexpressing cell lines. Furthermore, our data suggest that therapeutic glycoproteins which have reduced M6P-phosphorylation levels can be targeted for CI-M6PR-mediated lysosomal delivery by creating fusion proteins where the fused region is capable of N-linked glycosylation and M6P-phosphorylation.

Figure 8:
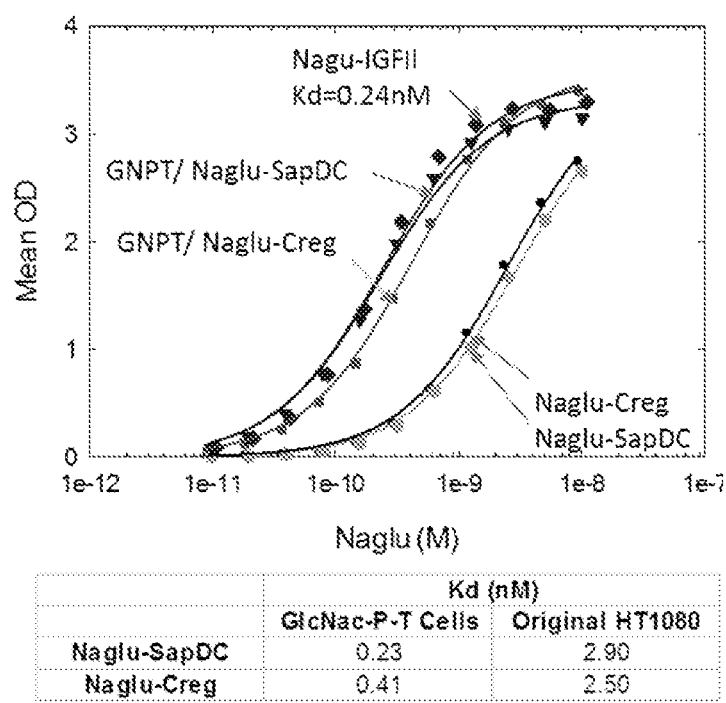
FIG. 8 shows the in vitro M6P receptor binding of various Naglu fusion proteins produced in HT1080 cells or a GNPT overexpressing cell line (GlcNAc-P-T).

In the second phase of our study, CI-M6PR binding of the remaining Naglu fusion proteins was evaluated, using the same in vitro binding assay as described above. Consistent with our previous findings, the data indicate that both Naglu-CREG and Naglu-SapDC fusion proteins were able to bind CI-M6PR. This demonstrated that therapeutic glycoproteins can be engineered as fusion proteins with lysosomal targeting moieties to facilitate binding to CI-M6PR. Naglu-SapDC and Naglu-CREG fusion proteins had a binding affinity for CI-M6PR of 2.90 nM and 2.50 nM, respectively (FIG. 8), which was greater than the binding affinity of rhNaglu (none detected) and rhNaglu produced in cells overexpressing GNPT (65 nM) (FIG. 7). The production of fusion proteins in GNPT overexpressing cells lead to a further increase of their M6P-phosphorylation, as evident from the dramatic increase of their binding affinity for CI-M6PR, (0.23 nM for GNPT/Naglu-SapDC and 0.41 nM for GNPT/Naglu-CREG) that was similar to the binding affinity observed regarding Naglu-IGF-II (0.24 nM) (FIG. 8).

Example 7: Increased M6P-Modification of Naglu-Fusion Proteins Produced Using a GNPT Cell Line To further confirm the increases of M6P on Naglu-LIF and Naglu-SapDC after coexpression with GNPT, a monosaccharide M6P quantitation assay was performed. This method used acid hydrolysis to break down all the glycans on the analyzed glycoproteins; the released monosaccharide, such as M6P, was then detected and quantified by PAD-HPLC (Pulsed Amperometric Detection High Performance Liquid Chromatography). Briefly, M6P disodium salt was used to identify the peak of the M6P liberated from the analyzed samples. The area under the curve for the M6P standard was used to generate a standard curve, allowing the quantification of the liberated M6P from the samples. The M6P content of Naglu-SapDC increased from 0.75 to 1.84 mol/mol (M6P/Protein) after co-expression with GNPT, and the M6P content of Naglu-LIF increased to 1.07 after co-expression with GNPT (FIG. 9). Both, the GNPT co-expressed Naglu-SapDC and the GNPT co-expressed Naglu-LIF had M6P a content that was very similar to the M6P a content of the control protein I2S (FIG. 9). This result indicates that GNPT co-expression increased the M6P content of Naglu fusion proteins to a level that is therapeutically meaningful. The method used to quantify M6P on Naglu-LIF and Naglu-SapDC is set forth in more detail below.

The procedure for mannose-6-phosphate quantitation by PAD-HPLC was adapted from Zhou et al. 2002, Anal Biochem. 15; 306(2):163-170). Protein samples were mixed with 13 M trifluoroacetic acid (TFA) to a final concentration of 6.75 M TFA. The mixture was then transferred to a 0.5 ml glass vial with a screw cap. Standards were prepared using mannose-6-phosphate disodium purchased from Sigma-Aldrich Corporation (St. Louis. Mo.). The standards were prepared in $H_2O$/TFA in concentrations ranging from 50 to 1000 pM, and were then transferred to glass vials with screw caps. All samples were heated at 100° C. for 1.5 hours in a heating block. After heating, the glass vials were placed on ice for 5 minutes, and the samples were transferred to Eppendorf tubes. The samples were centrifuged at 14,000 rpm for 2 minutes and then dried in a SpeedVac® concentrator for ~1.5 hours. 200 µl of Milli-Q® water were then added to each sample and the samples were again dried as before. Then, 100 µl of Milli-Q® water were added to each sample and the samples were filtered through a 0.45 µm Durapore® centrifugal filter unit (Millipore, Billerica, Mass.) at 14,000 rpm for 5 minutes. 20 microliters of each sample and of the standards were injected in a chromatography system with a borate trap column in line with a CarboPac PA 10 analytical column (Dionex ICS-3000 Ion Chromatography System (Thermo Fisher Scientific, Inc., Sunnyvale, Calif.)). An isocratic gradient was run with at 80% Eluent A (100 mM NaOH) and 20% Eluent B (1 M NaAc in 100 mM NaOH) for 15 minutes with a step up to 70% Eluent B for 5 minutes, then back to 20% Eluent B.

Figure 11:
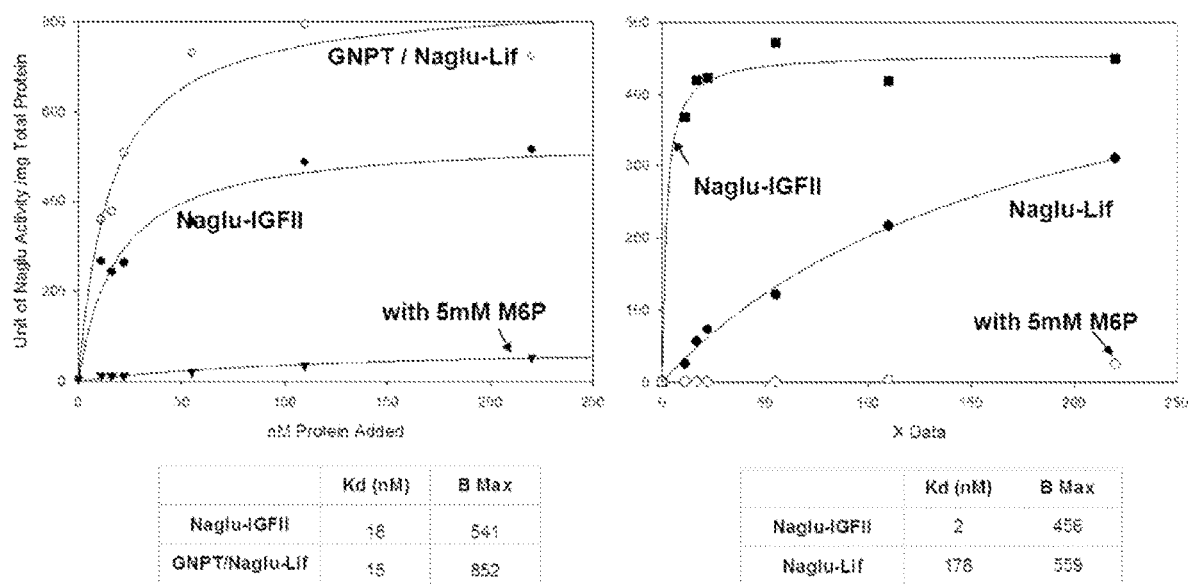
FIG. 11 illustrates in vitro cellular uptake of Naglu-LIF produced in wild-type HT1080 cells or an N-acetylgucosamine-1-phosphotransferase (GNPT) overexpressing cell line. Cellular uptake of Naglu-IGFII was used as a control.

Example 8: Increased Cellular Uptake of Naglu-Fusion Proteins Produced Using a GNPT Cell Line In vitro CI-M6PR mediated targeting and cellular uptake of Naglu-SapDC and Naglu-LIF produced in GNPT overexpression cell lines was also evaluated (FIGS. 10-11). Cellular uptake of Naglu-IGFII was determined for comparison. All samples were run in parallel, under identical conditions, to make the resulting data comparable.

Briefly, cells overexpressing CI-M6PR were grown to confluence and treated with a solution of either recombinant Naglu-SapDC and Naglu-Lif produced in HT-1080 cells alone, or recombinant Naglu-SapDC and Naglu-Lif produced in HT-1080 cells also overexpressing GNPT. After a specified period of time, the supernatant was removed and the cells were washed repeatedly. Following lysis, each cell sample was assayed for intracellular Naglu enzyme activity, and the total protein was measured by a BCA protein assay. The x-axis of the graphs in FIGS. 10-11 represented the amount of Naglu-SapDC or Naglu-LIF applied to the cells. The y-axis represented the intracellular Naglu activity, or the equivalent amount of Naglu enzyme in nanogram (ng) (see FIG. 10 top panel) normalized by the total protein amount.

The data show that Naglu-SapDC produced in GNPT overexpressing cells has an affinity for CI-M6PR that is 14 times higher than the affinity of Naglu-SapDC produced in cells expressing Naglu-SapDC alone ($K_D$=14.88 vs. $K_D$=208.78 nM, respectively) (FIG. 10). The affinity of Naglu-IGFII for CI-M6PR is only 3.6 times higher than the affinity of Naglu-SapDC produced in GNPT overexpressing cells ($K_D$ of 4.07 vs. 14.88 nM, respectively) (FIG. 10). No cellular uptake of Naglu-SapDC was observed when exogenous M6P was added to Naglu-SapDC samples, further confirming that cellular uptake of Naglu-SapDC is mediated by CI-M6PR via the M6P binding domain (FIG. 10).

Similarly, our data show that Naglu-LIF produced in GNPT overexpressing cells has an affinity for CI-M6PR that is higher than the affinity of Naglu-LIF produced in cells expressing Naglu-LIF alone (FIG. 11). The affinity of Naglu-IGFII for CI-M6PR is similar to the affinity of Naglu-LIF produced in GNPT overexpressing cells ($K_D$ of 18 vs. 15 nM, respectively), while the affinity of Naglu-LIF expressed in HT1080 cells alone is significantly lower than the affinity of Naglu-IGFII ($K_D$ of 178 nM vs. 2 nM, respectively). No cellular uptake of Naglu-LIF was observed when exogenous M6P was added to Naglu-LIF samples, further confirming that cellular uptake of Naglu-LIF is mediated by CI-M6PR via the M6P binding domain.

Example 9: In Vivo Delivery of Naglu-SapDC Fusion Protein

Intracellular Accumulation of Naglu-SapDC

For in vivo experiments described herein, Naglu-SapDC prepared in GNPT overexpressing cells was utilized.

To further evaluate intracellular accumulation of the Naglu-SapDC fusion protein, an in vivo study was performed using Naglu KO mice subjected to intrathecal administration of vehicle control (PBS) or Naglu-SapDC; in accordance with the experimental conditions described in Table 7.

TABLE 7

Experimental Design to Assay Efficacy of Naglu-SapDC

| Group | No. | Treatment | Dose (mg/kg brain) | Route | Frequency | Sacrifice |
|---|---|---|---|---|---|---|
| A | 3 | Vehicle | N/A | Intrathecal | 2× Weekly | 24 hrs post final dose |
| B | 6 | Naglu-SapDC | 520 | | | |
| C | 3 | Vehicle | N/A | Intrathecal | 3× Weekly | 24 hrs post final dose |
| D | 6 | Naglu-SapDC | 520 | | | |

Figure 12A:
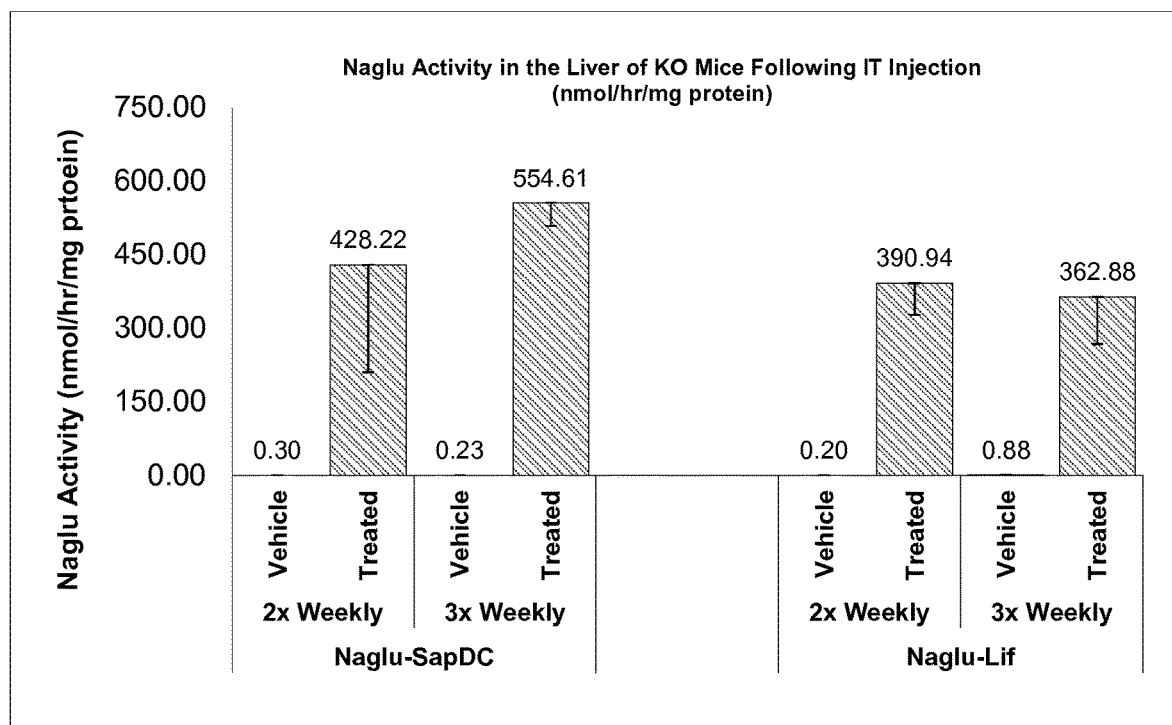
FIG. 12A-B demonstrates in vivo Naglu enzyme activity in mouse (A) liver and (B) brain tissue, following intrathecal delivery of vehicle control or Naglu-SapDC or Naglu-LIF fusion proteins to Naglu knock-out mice.
Figure 12B:
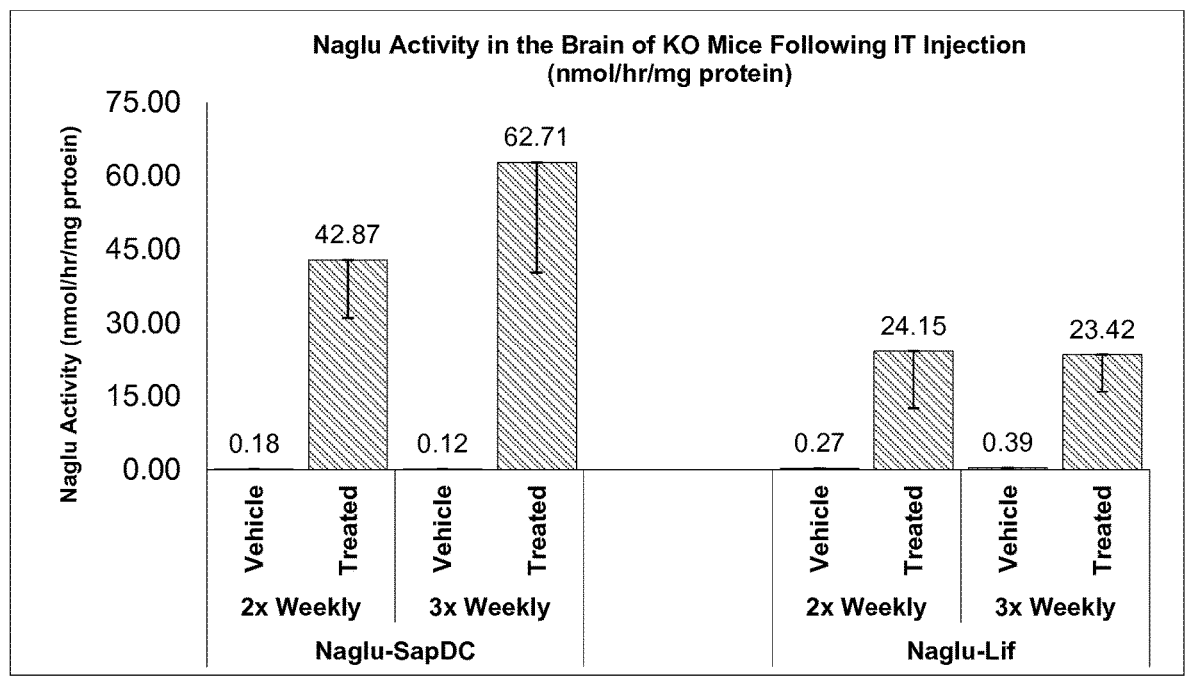

Following each respective treatment, Naglu KO mice were sacrificed 24 hours after their final injection and assayed for Naglu enzyme activity in various tissues. Total Naglu activity was assayed using a well-established enzyme activity assay. Briefly, tissue homogenate was incubated in the presence of the Naglu specific substrate methylumbelliferyl-N-acetyl-α-D-glucosainide for a specified period of time, after which accumulation of cleavage product was measured by examining fluorescence intensity at 360/460 (excitation/emission) using a fluorescent plate reader. The data demonstrate that treatment with Naglu-SapDC resulted in a dramatic increase in Naglu activity in both liver (FIG. 12A) and brain (FIG. 12B) tissue, when compared to vehicle control. This increase in enzyme activity was observed over the duration of the 3 week treatment period.

Biodistribution of Naglu-SapDC Fusion Protein

Figure 13A:
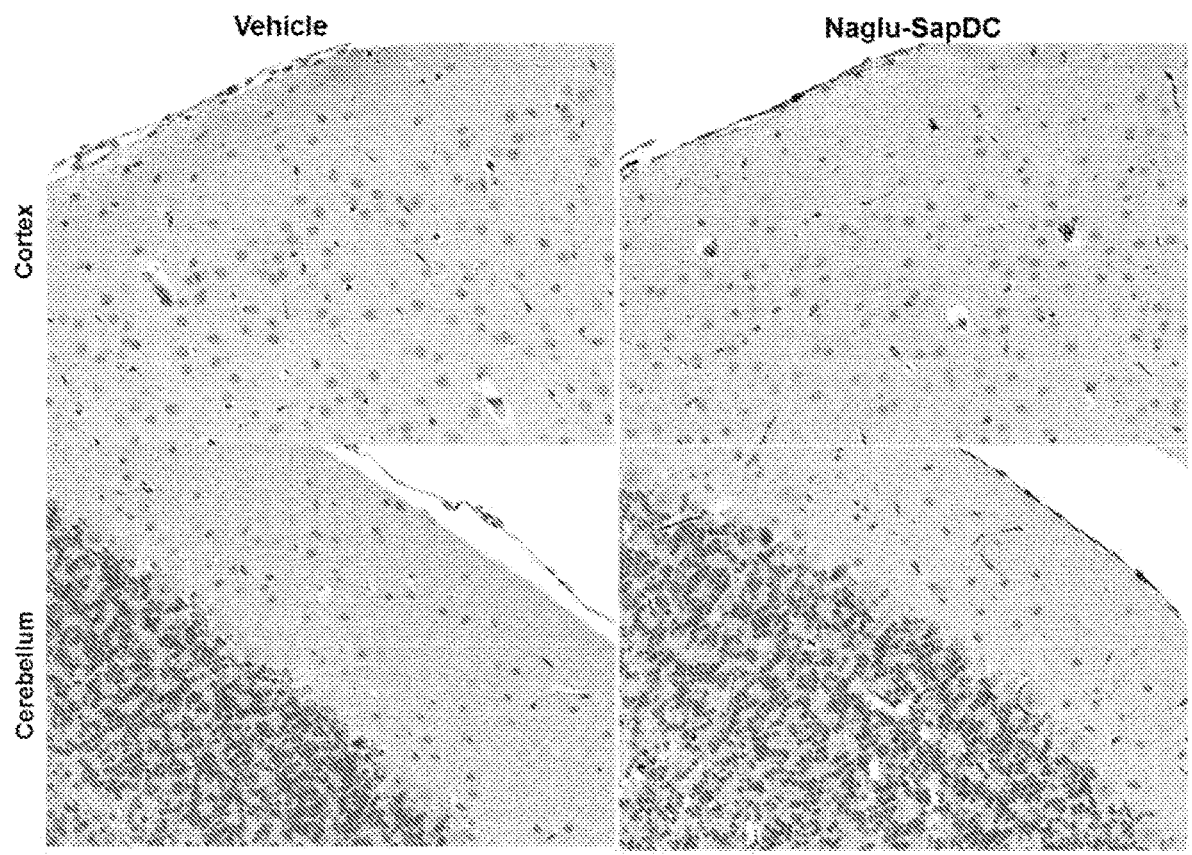
FIG. 13A-F shows immunohistochemical detection of Naglu protein in tissues. Naglu protein is detectable in neurons of the cerebral cortex and cerebellum of Naglu-knockout mice having received three weekly intrathecal injections of vehicle control or (A) Naglu-SapDC or (C) Naglu-LIF fusion proteins. Naglu+ stained neurons in the cerebral cortex of mice injected with Naglu-SapDC and Naglu-LIF are circled (B and D, respectively). Similarly, Naglu was detected in the liver of Naglu-knockout mice following three weekly intrathecal injections of vehicle control or Naglu-SapDC (E) or Naglu-LIF (F).
Figure 13B:
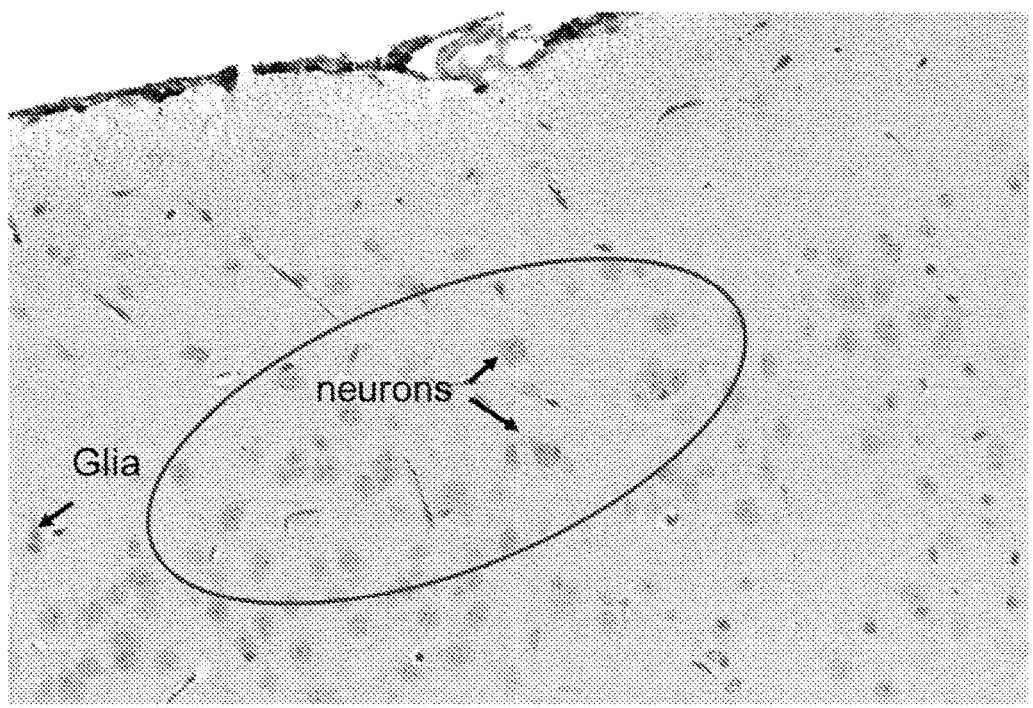
Figure 13C:
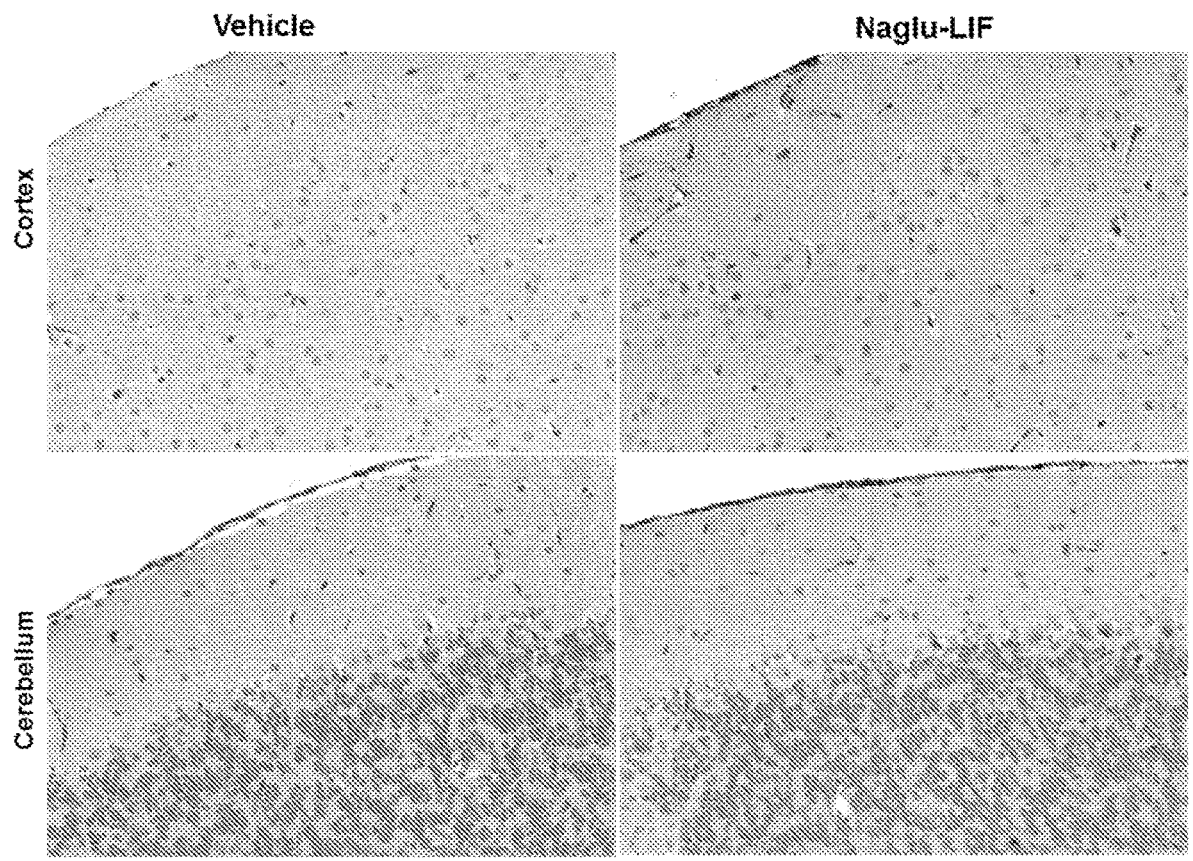
Figure 13D:
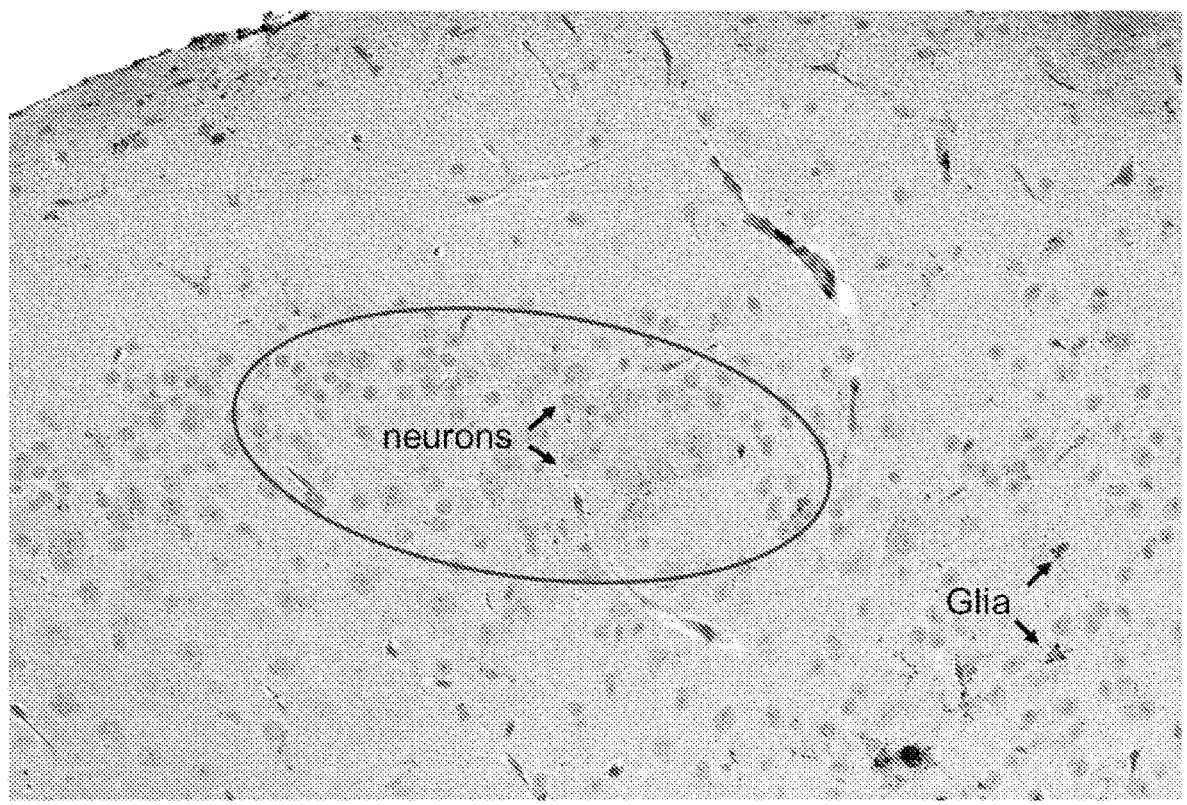
Figure 13E:
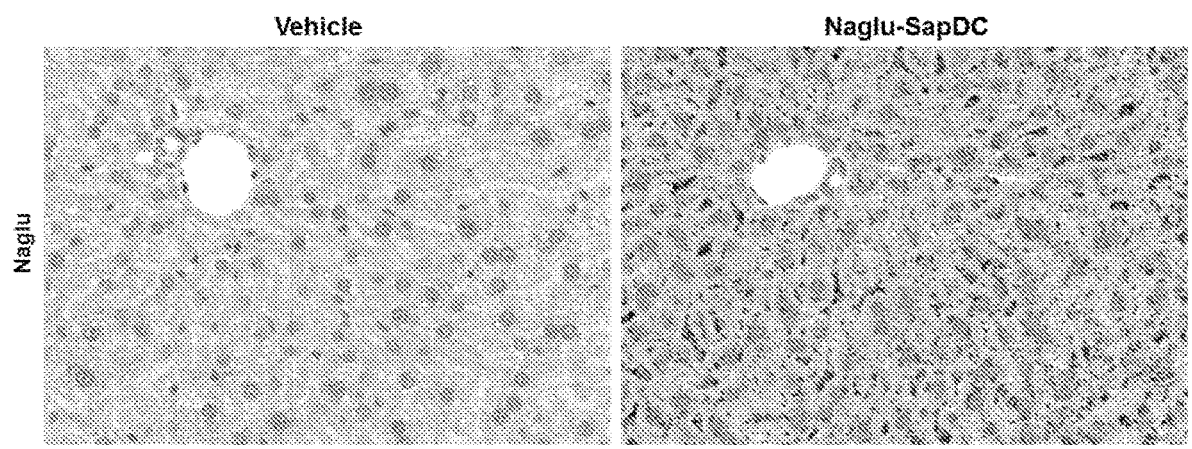

Tissue samples were also collected from the treated mice, fixed in 10% NBF and processed for paraffin embedding. For each tissue assayed, 5 μm paraffin sections were subjected to immunostaining using an antibody specific for human Naglu. The data clearly demonstrate lysosomal delivery of Naglu-SapDC to neurons of the cerebral cortex (FIG. 13 A, B). Most strikingly, the data also demonstrate lysosomal delivery of Naglu-SapDC in hepatic cells of the liver (FIG. 13E). This is surprising insofar as Naglu-SapDC was administered via intrathecal delivery, indicating Naglu-SapDC can reach targets and enter cells far away from its site of administration.

Efficacy of Naglu-SapDC Fusion Protein

Figure 14:
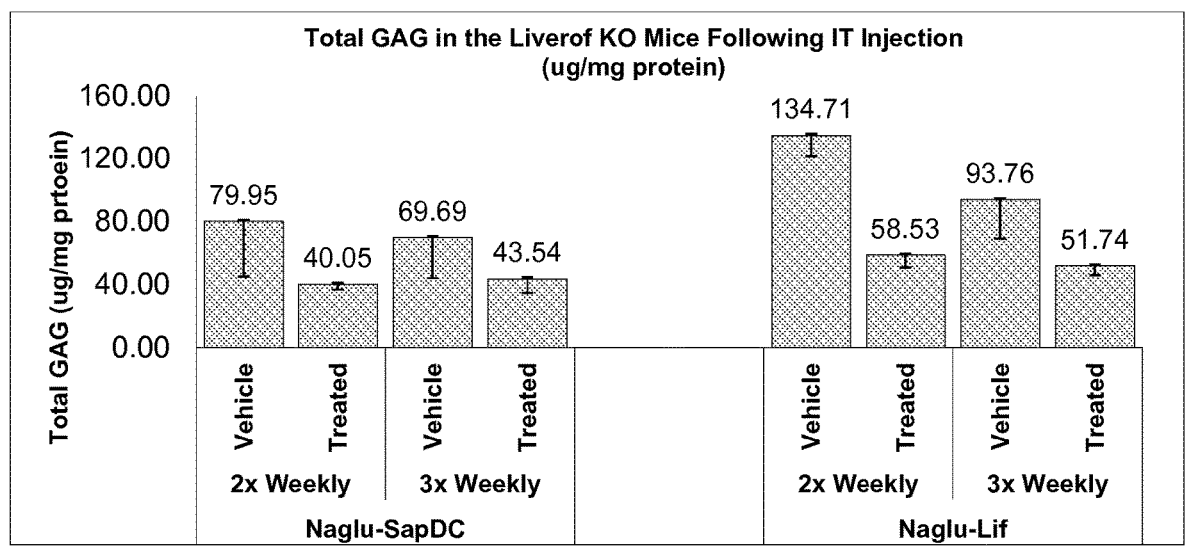
FIG. 14 demonstrates in vivo levels of glycosaminoglycan (GAG) in mouse liver following intrathecal delivery of vehicle control or the Naglu-SapDC and Naglu-LIF fusion proteins to Naglu knock-out mice.
Figure 15:
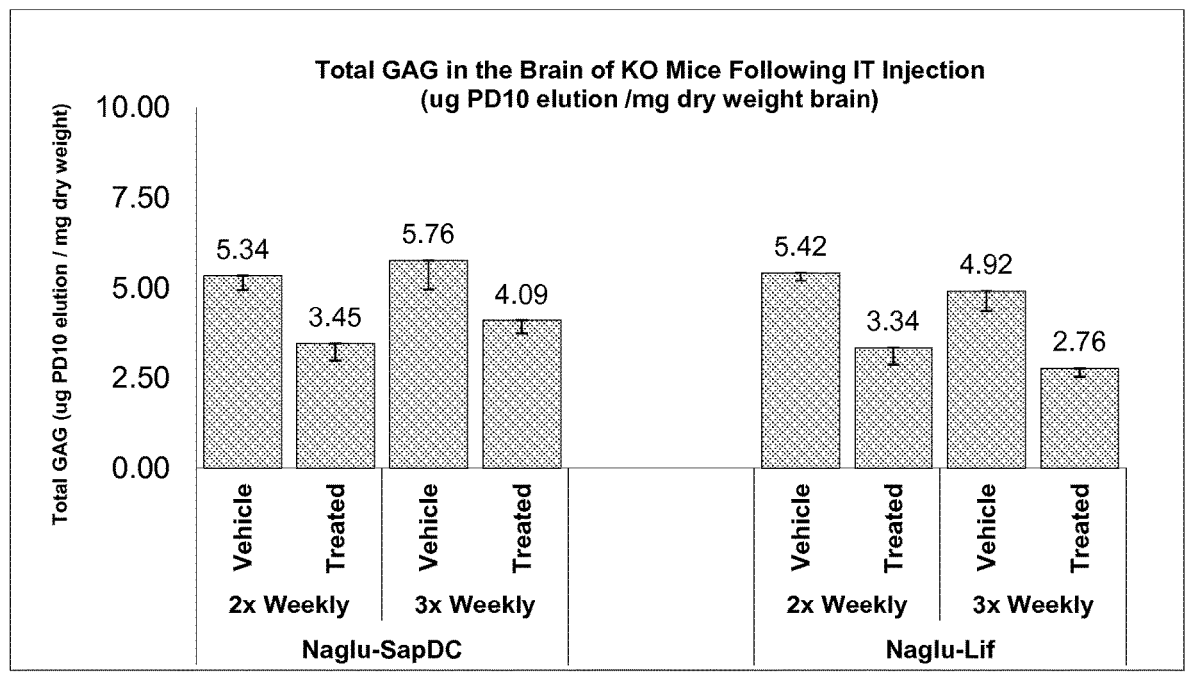
FIG. 15 demonstrates in vivo levels of glycosaminoglycan (GAG) in mouse brain, following two and three weekly intrathecal injections of vehicle control or Naglu-SapDC and Naglu-LIF fusion proteins to Naglu knock-out mice.

The in vivo activity of Naglu enzyme in Naglu knockout mice treated by intrathecal administration of Naglu-SapDC was evaluated by examining the intracellular accumulation of different glycoproteins and their respective cleavage products. One such assay was designed to evaluate the amount of glucosoaminoglycan (GAG) in liver (FIG. 14) and brain tissue (FIG. 15).

Briefly, liver tissues were homogenized and then assayed for GAG according to Jong et al. (Clin Chem 38(6):803-807, 1992). In the case of brain tissue, the homnogenized samples were further digested using pronase and benzonase to break down protein and nucleic acid. GAG was then extracted by passing the sample through a DEAE column. The buffer of the eluate was then exchanged by means of a desalting column, and the total amount of GAG was determined using dimethylmethylene blue staining (Lawrence et al., Nat Chem Biol. 2012 Jan. 8; 8(2):197-204). As shown in FIGS. 14 and 15, intreathecal delivery of Naglu-SapDC resulted in a significant reduction in total GAG concentration within the liver and brain of Naglu knockout mice, when compared to the vehicle control. The reduction of the total GAG level within the brain was maintained over the entire 3 week treatment period (FIG. 15).

Figure 16:
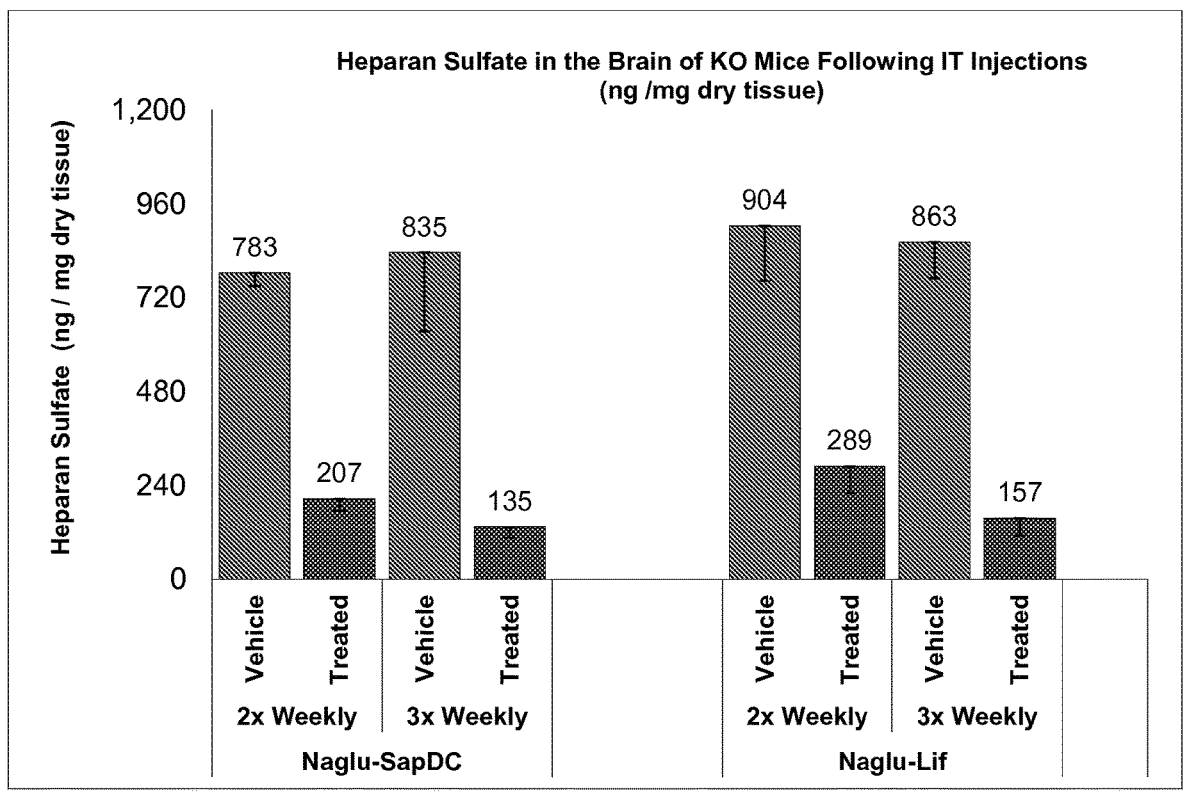
FIG. 16 demonstrates in vivo levels of heparan sulfate (HS) in mouse brain, following two and three weekly intrathecal injections of vehicle control or the Naglu-SapDC and Naglu-LIF fusion proteins to Naglu knock-out mice.

A second assay was performed to evaluate the amount of heparan sulfate in brain tissue following intrathecal delivery of Naglu-SapDC fusion protein. Heparin sulfate is a specific type of GAG which has been shown to accumulate in the brain of San B patients. To measure heparan sulfate in brain tissue, a highly sensitive LC/MS method was used, as described by Lawrence et al. (Nat Chem Biol. 2012 Jan. 8; 8(2):197-204). Briefly, total GAG from brain tissue was extracted using a DEAE column and a desalting column, ad was then dried and weighted. The weighted GAG was then treated with heparin lyases that specifically release unique mono, di and tri saccharides from heparan sulfate. Released disaccharides were then analyzed, identified and quantified by LC/MS and comparison to commercially available disaccharide standards. As in the case of the GAG study described above, the data illustrate that, when compared to vehicle control, treatment with Naglu-SapDC leads to a strong reduction in the total amount of heparan sulfate accumulation in the brain over the duration of the three week treatment period (FIG. 16).

Figure 17:
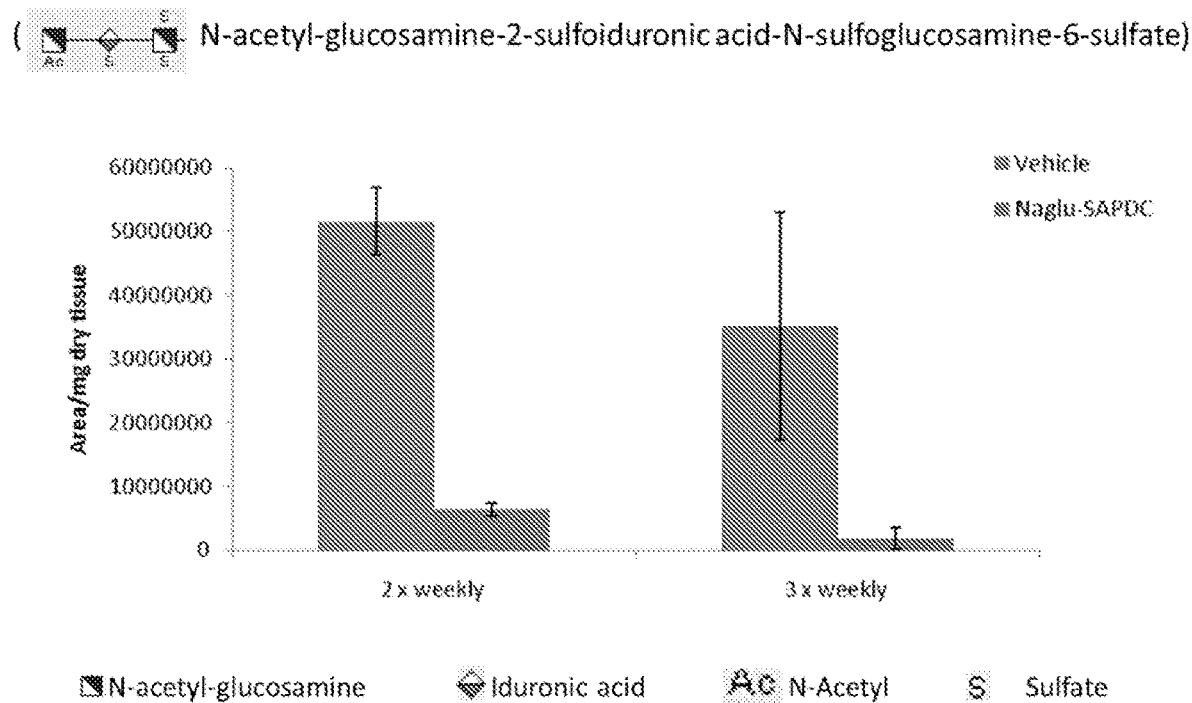
FIGS. 17-19 demonstrate in vivo levels of three San B biomarkers in mouse brain, following intrathecal delivery of vehicle control (PBS) or Naglu-SapDC fusion protein to Naglu knock-out mice.
Figure 18:
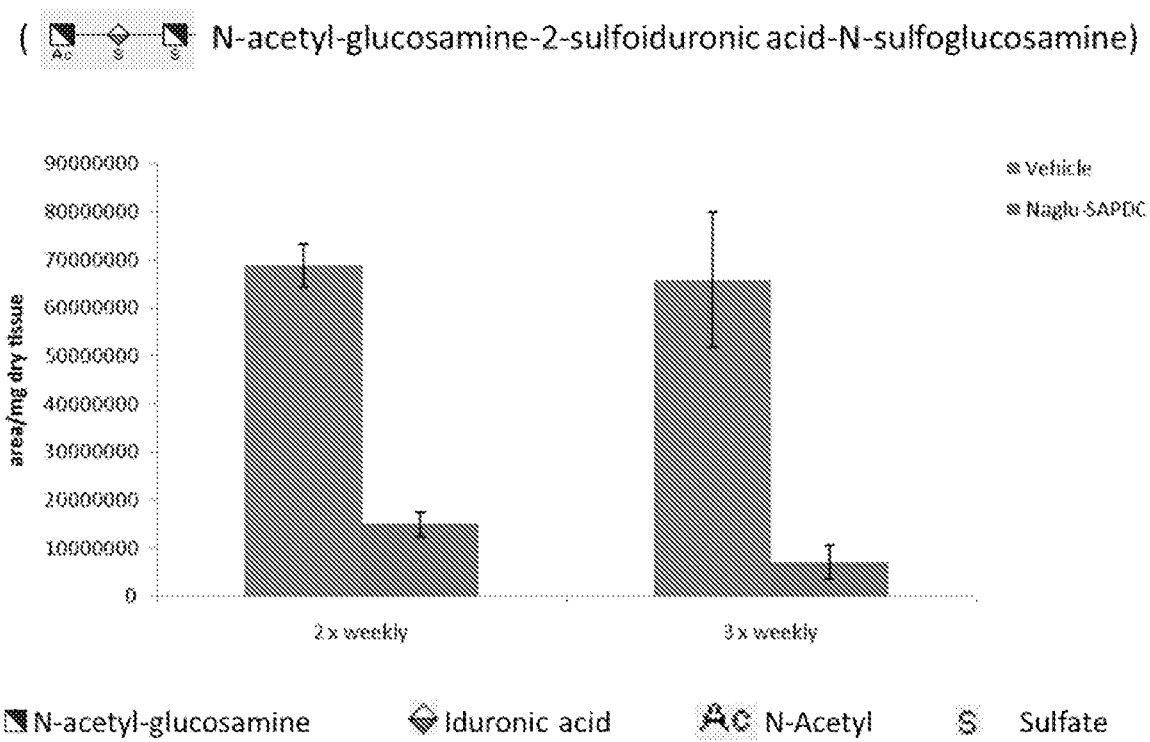
Figure 19:
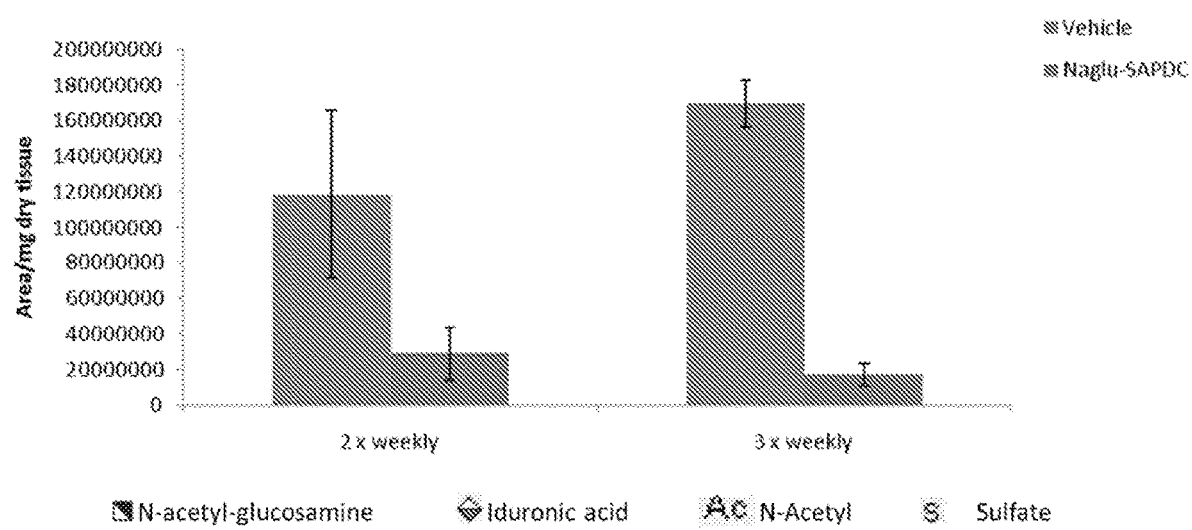

Lastly, intracellular delivery of Naglu-SapDC was evaluated by assaying the presence of different biomarkers for San B, using the same LC/MS methodology used for the determination of heparin sulfate tissue content, described above. Deficiency of Naglu causes the accumulation of aberrant heparan sulfate cleavage products in tissues (presented in FIGS. 17-19) which are natural substrates of Naglu. The data show that intrathecal delivery of Naglu-SapDC to Naglu knockout mice results in a dramatic decrease in the brain of the accumulation of all three aberrant heparan sulfate cleavage products analyzed (FIGS. 17-19). Taken together, all these three experimental approaches demonstrate an overall reduction in GAG levels and cleavage products, suggesting Naglu-SapDC is efficiently internalized into the lysosome of the cell, where it maintains enzyme activity.

Figure 20:
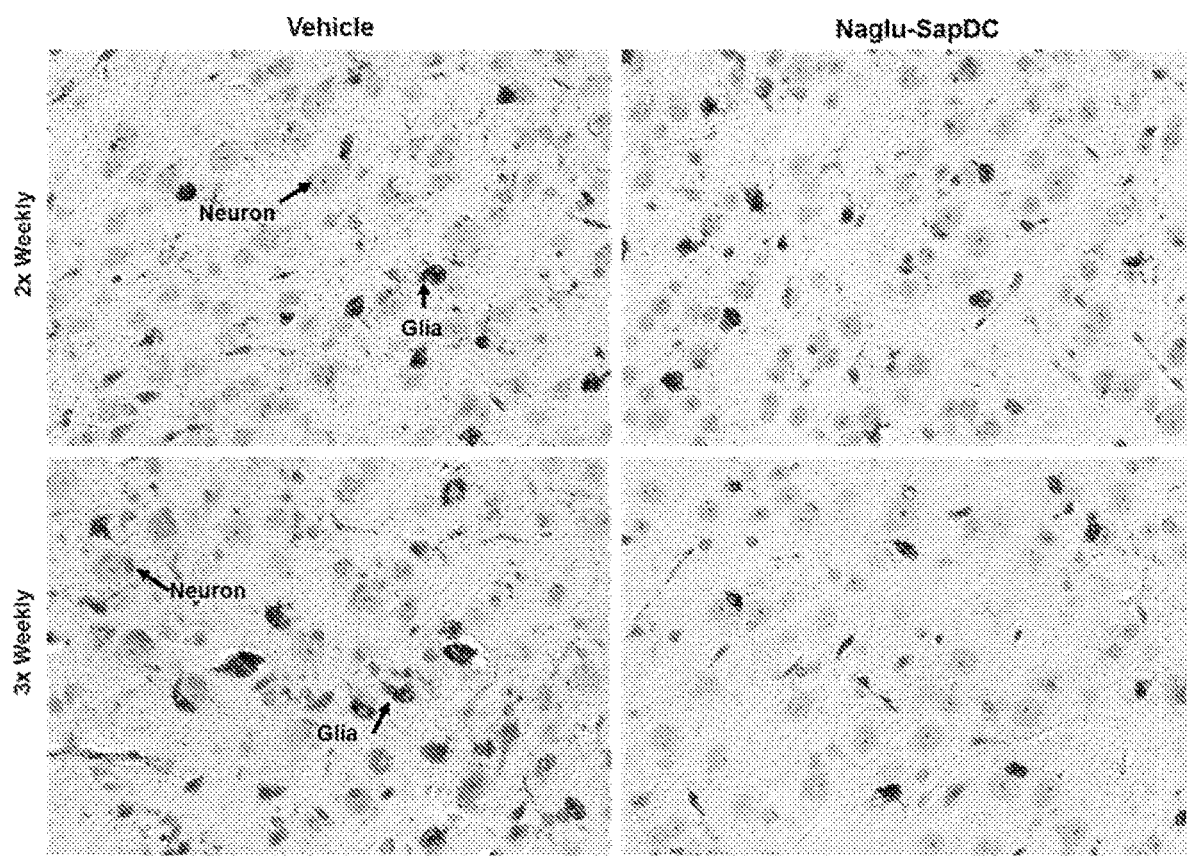
FIG. 20 illustrates LAMP-1 immunohistochemical staining in mouse cerebral cortex tissue, following two or three weekly intrathecal injections of vehicle control or Naglu-SapDC fusion protein.
Figure 21:
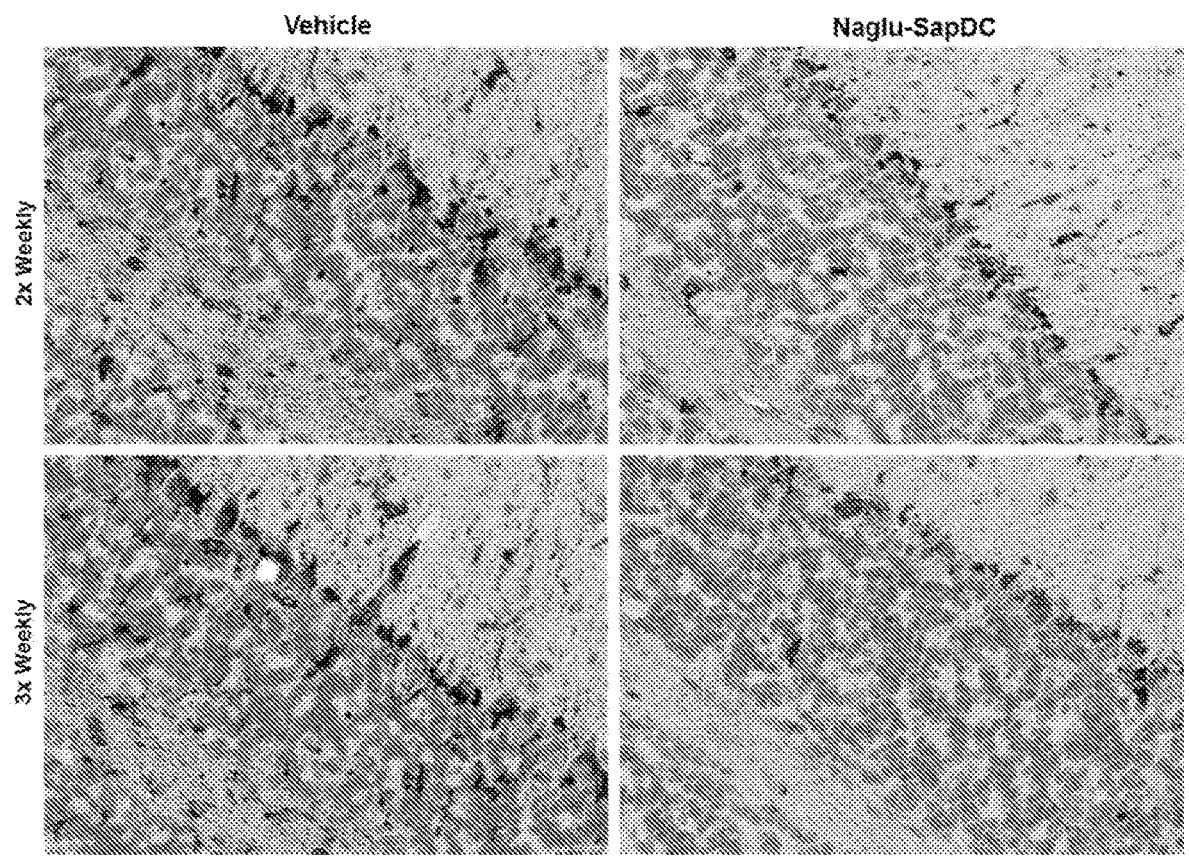
FIG. 21 illustrates LAMP-1 immunohistochemical staining in mouse cerebellum tissue, following two or three weekly intrathecal injections of vehicle control or Naglu-SapDC fusion protein.
Figure 22:
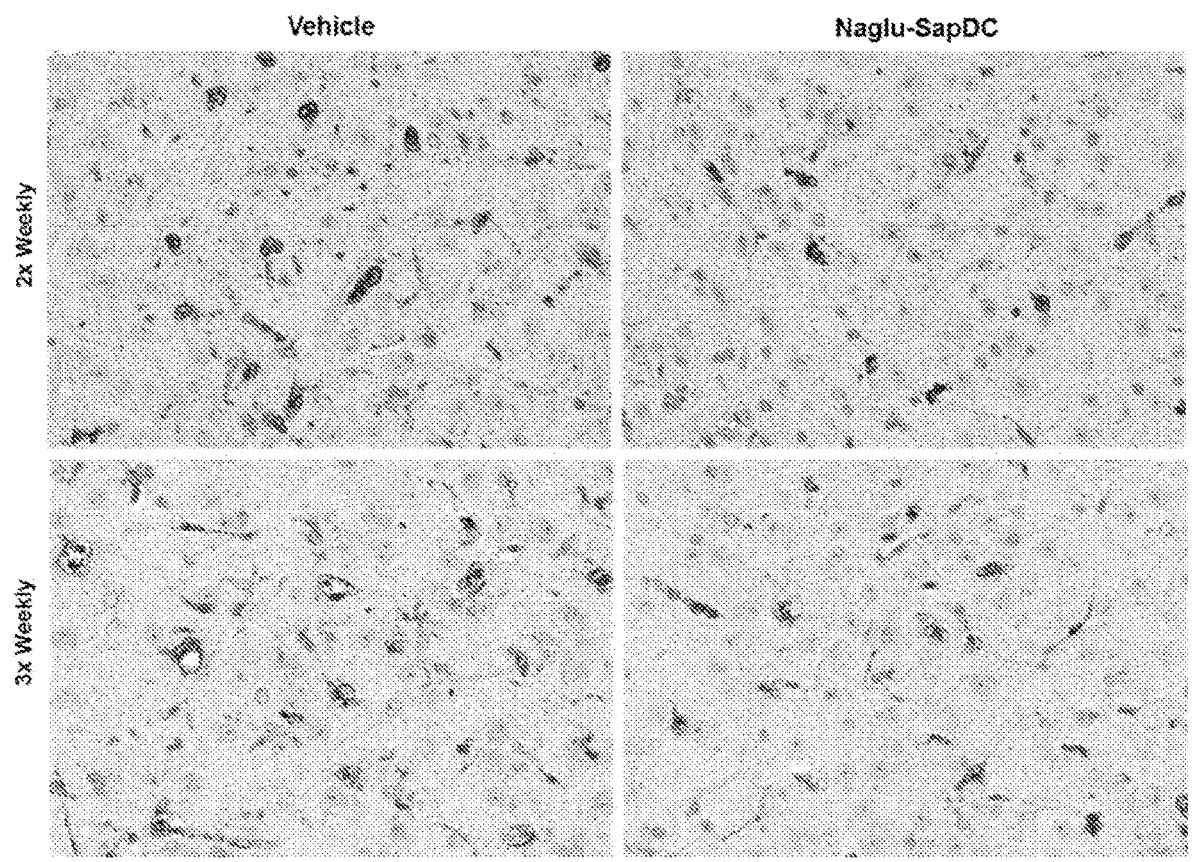
FIG. 22 illustrates LAMP-1 immunohistochemical staining in mouse thalamus tissue, following two or three weekly intrathecal injections of vehicle control or Naglu-SapDC fusion protein.
Figure 23:
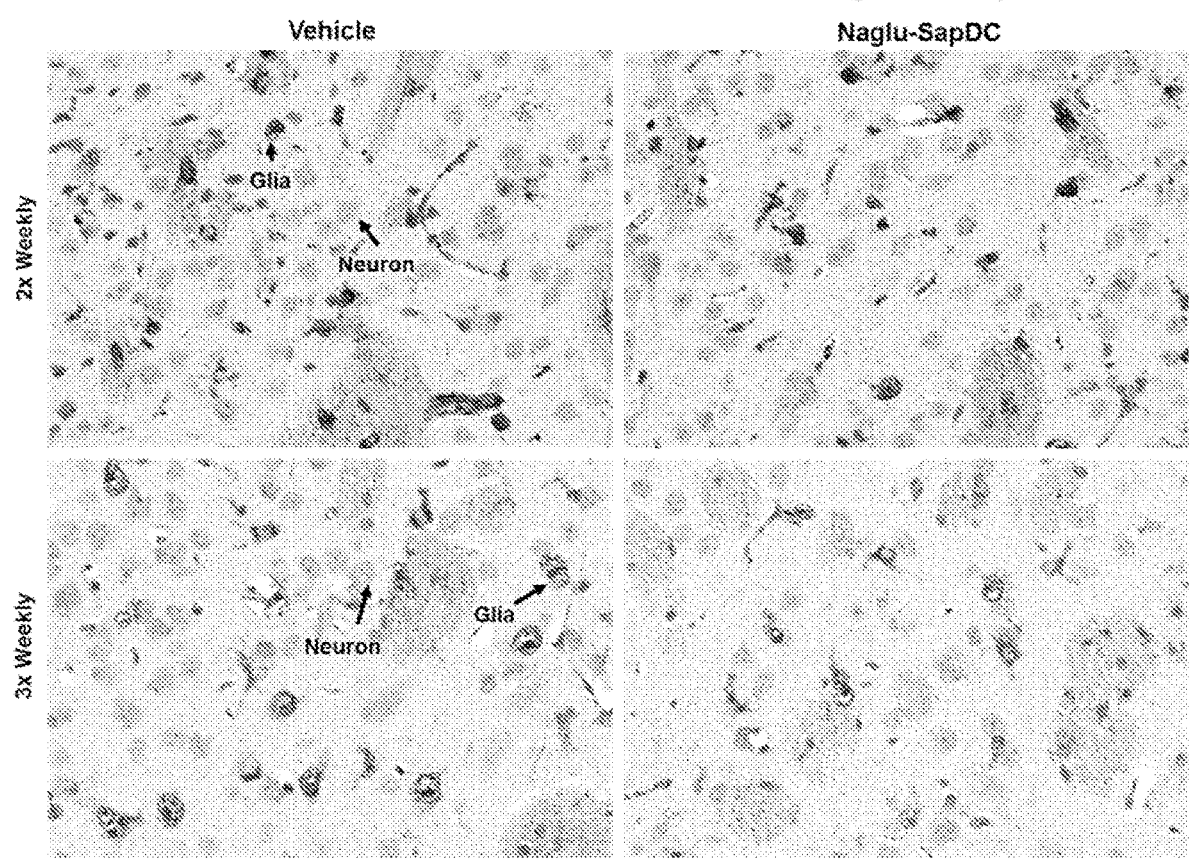
FIG. 23 illustrates LAMP-1 immunohistochemical staining in mouse striatum tissue, following two or three weekly intrathecal injections of vehicle control or Naglu-SapDC fusion protein.
Figure 24:
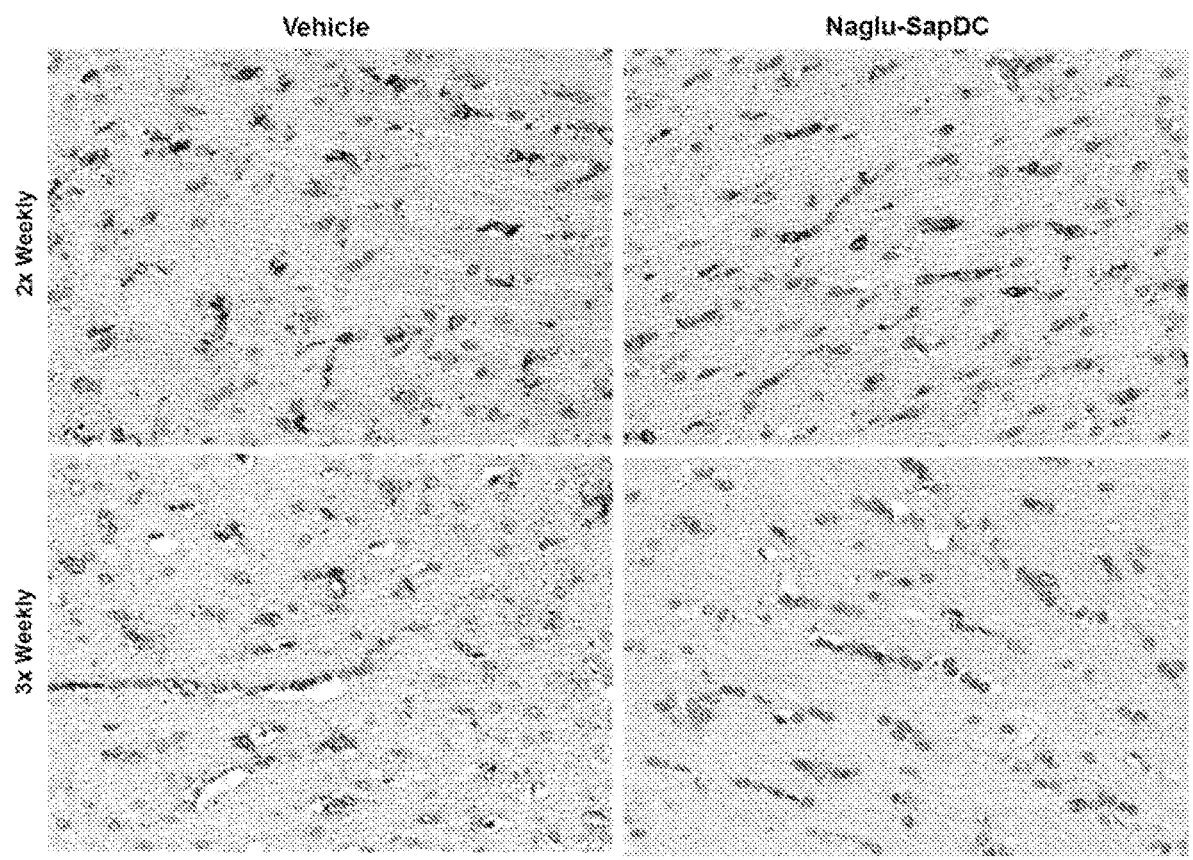
FIG. 24 illustrates LAMP-1 immunohistochemical staining in mouse white matter tissue, following two or three weekly intrathecal injections of vehicle control or Naglu-SapDC fusion protein.
Figure 25:
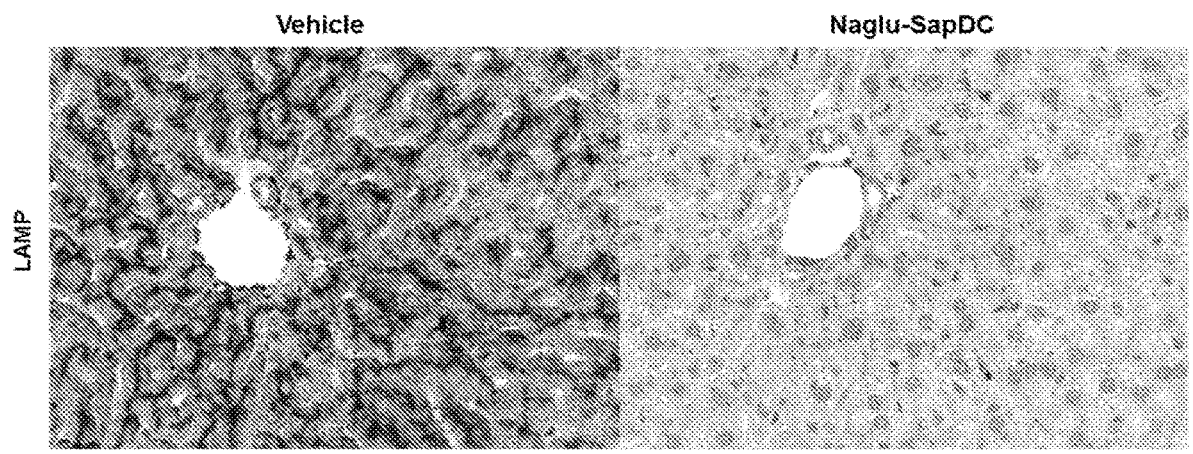
FIG. 25 illustrates LAMP-1 immunohistochemical staining in mouse liver tissue, following three weekly intrathecal injections of vehicle control or Naglu-SapDC fusion protein.

To further elucidate and confirm the intracellular delivery of Naglu-SapDC to lysosomes, the inventors examined the distribution of the lysosomal marker Lamp-1 in each experimental treatment group. Vehicle control mice, when compared to Naglu-SapDC treated mice, showed an increased immunohistochemical staining for Lamp-1 over the entire 3 week period in the apparently enlarged lysosomes of neuronal and glia cells of the cerebral cortex (FIG. 20), cerebellum (FIG. 21), thalamus (FIG. 22), striatum (FIG. 23), white matter (FIG. 24) and liver (FIG. 25).

Figure 26:
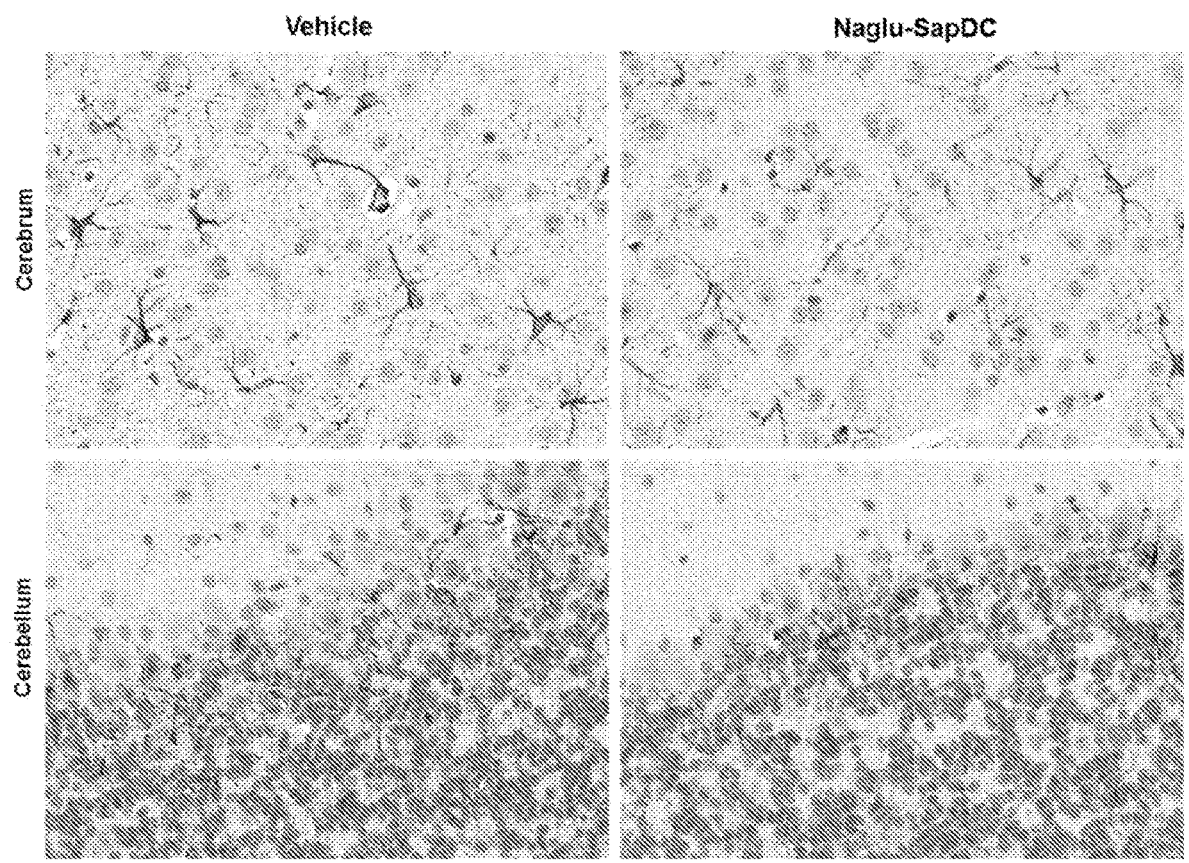
FIG. 26 illustrates immunohistochemical staining of GFAP in mouse cerebrum and cerebellum tissue, following three weekly intrathecal injections of vehicle control or Naglu-SapDC fusion protein.
Figure 27:
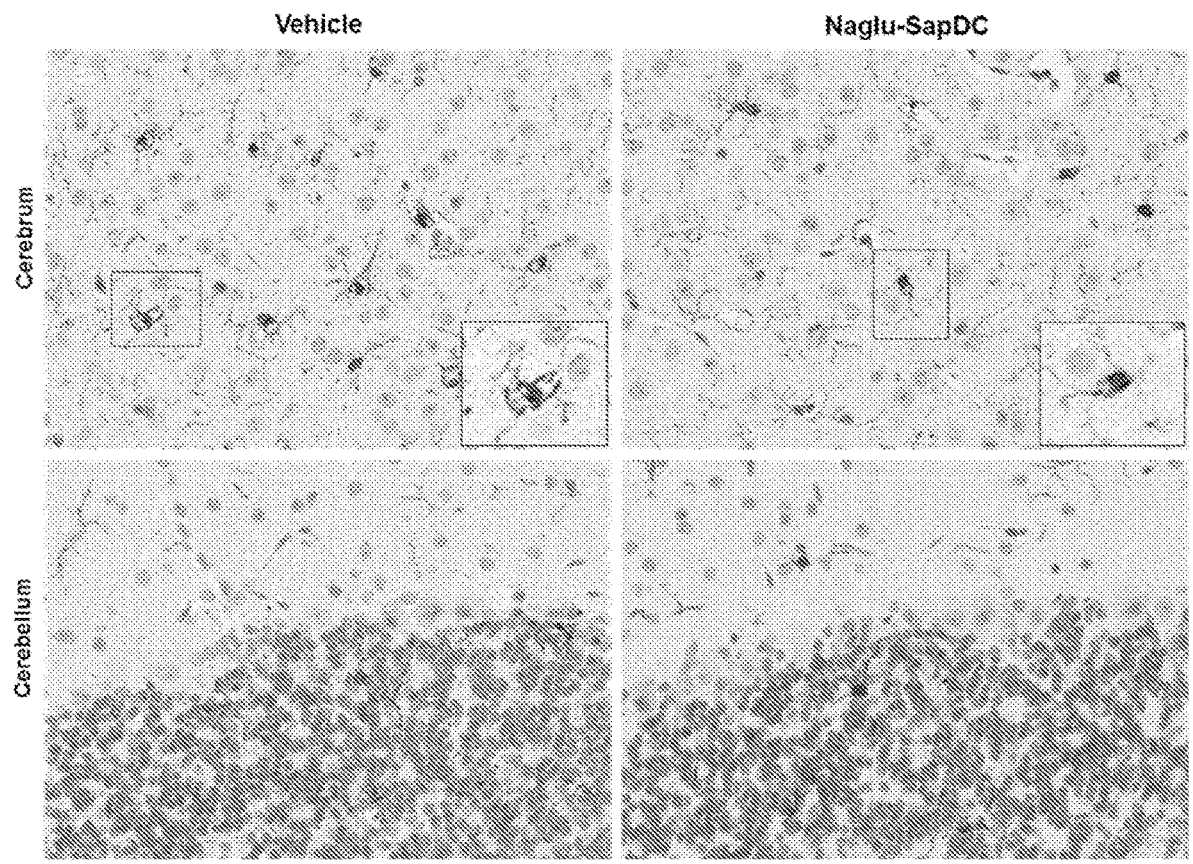
FIG. 27 illustrates immunohistochemical staining of Iba-1 in mouse cerebellum and cerebrum tissue, following three weekly intrathecal injections of vehicle control or Naglu-SapDC fusion protein.

In addition to Lamp-1, two additional cellular biomarkers were used to further evaluate lysosomal targeting and intracellular delivery of Naglu-SapDC. For this study, the ionized calcium-binding adapter molecule 1 (Iba-1) and glial fibrillary acidic protein (GFAP) were chosen as markers. Each protein is a well-established indicator of cellular inflammatory response and can be used to gauge the level and intensity of inflammation in specific cell types. In particular, GFAP staining has been used extensively to demonstrate the size and number of processes in astrocytes, while Iba-1 staining is predominantly used for evaluating microglial cells. As demonstrated in FIG. 26, mice subjected to intrathecal delivery of Naglu-SapDC had a reduced amount of GFAP staining in each neuronal tissue examined, indicating reduced lysosome size and a low number of processes. A similar trend was also observed for Iba-1 staining, for each neuronal sample analyzed (FIG. 27).

These data provide strong in vivo support that Naglu-SapDC is able to bind the CI-M6P receptor, which facilitates lysosomal targeting and entry in various tissues types. Surprisingly, intrathecal delivery of Naglu-SapDC resulted in extensive bioavailability throughout the body, demonstrating localization in neuronal tissue as well as various organ systems of the body, such as the liver. The data further suggest, that upon entry into the cell, the Naglu-SapDC fusion protein maintains enzyme activity and proper function, as demonstrated by the overall reduction in excess accumulation of glucosaminoglycans, heparin sulfate and San B specific biomarkers in Naglu knockout mice, which is a hallmark of Sanfilippo type B disease. Given the fusion protein's excellent efficacy, biodistribution and ability to target lysosomal delivery using the CI-M6P receptor mediated pathway, the data strongly suggest that such an approach could be extremely effective for enzyme replacement therapy. Despite the d little to no M6P-phosphorylation of rhNaglu, Naglu-SapDC fusion proteins can be M6P-phosphorylated and thus targeted for CI-M6P receptor mediated lysosomal delivery. Our data clearly suggest that the described lysosomal targeting approach is applicable not only to the treatment of Sanfillipo type B syndrome, but also to the treatment of any other lysosomal storage diseases in which, for example, the native protein lacks a proper M6P-phosphorylation site, or is poorly M6P-phosphorylated due competitive inhibition or steric hindrance of the GNPT enzymatic pocket.

Example 10: In Vivo Delivery of Naglu-LIF Fusion Protein

Intracellular Accumulation of Naglu-LIF

For in vivo experiments described herein, Naglu-LIF prepared in GNPT overexpressing cells was utilized.

To further evaluate intracellular accumulation of the Naglu-LIF fusion protein, an in vivo study was performed using Naglu KO mice subjected to intrathecal administration of vehicle control (PBS) or Naglu-LIF; in accordance with the experimental conditions described in Table 8.

TABLE 8

Experimental Design to Assay Efficacy of Naglu-LIF

| Group | Treatment No. | Treatment | Dose (mg/kg brain) | Route | Frequency | Sacrifice |
|---|---|---|---|---|---|---|
| A | 3 | Vehicle | N/A | Intrathecal | 2× Weekly | 24 hrs post final dose |
| B | 6 | Naglu-LIF | 520 | | | |
| C | 3 | Vehicle | N/A | Intrathecal | 3× Weekly | 24 hrs post final dose |
| D | 6 | Naglu-LIF | 520 | | | |

Following each respective treatment, Naglu KO mice were sacrificed 24 hours after their final injection and assayed for Naglu enzyme activity in various tissues. Total Naglu activity was assayed using a well-established enzyme activity assay. Briefly, total cell lysate was incubated in the presence of the Naglu specific substrate methylumbelliferyl-N-acetyl-α-D-glucosainide for a specified period of time, after which accumulation of cleavage product was measured by examining fluorescence intensity at 360/460 (excitation/emission) using a fluorescent plate reader. The data demonstrate that treatment with Naglu-LIF resulted in a dramatic increase in Naglu activity in both liver and brain tissue, when compared to vehicle control. This increase in enzyme activity was observed over the duration of the 3 week treatment period.

Biodistribution of Naglu-LIF Fusion Protein

Figure 13F:
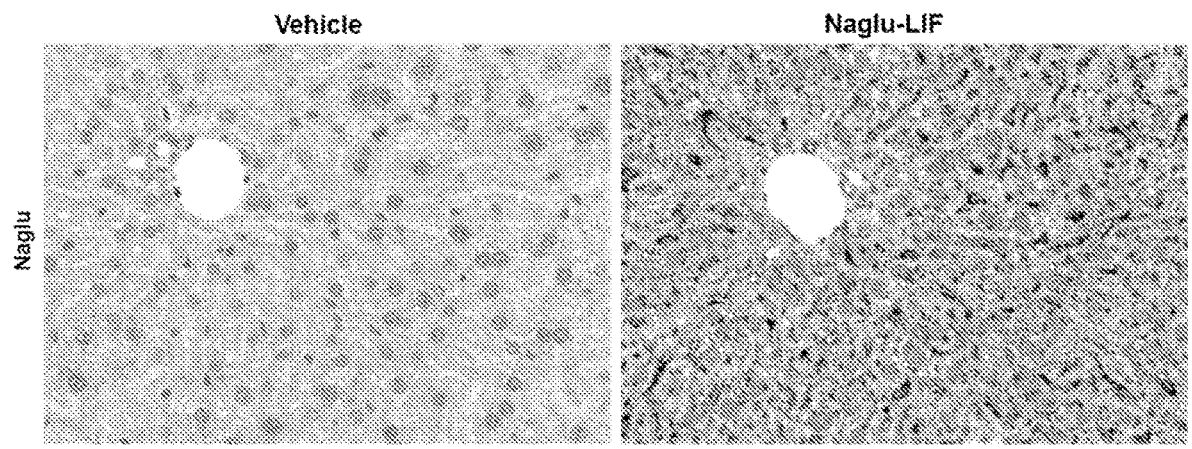

Tissue samples were also collected from the treated mice, fixed in 10% NBF and processed for paraffin embedding. For each tissue assayed, 5 µm paraffin sections was subjected to immunostaining using an antibody specific for human Naglu. The data clearly demonstrate lysosomal delivery of Naglu-LIF to neurons and glia cells of the spinal cord, meninges of the cerebellum, meninges of the cerebral cortex, and neurons and glia cells of limited areas in the cerebral cortex (FIGS. 13C and D). Most strikingly, the data also demonstrate lysosomal delivery of Naglu-LIF in hepatic cells of the liver (FIG. 13F). This is surprising insofar as Naglu-LIF was administered via intrathecal delivery, indicating Naglu-LIF can reach targets and enter cells far away from its site of administration.

Efficacy of Naglu-LIF Fusion Protein

The in vivo activity of Naglu was evaluated by examining the intracellular accumulation of GAG and heparin sulfate, as described above in connection with the analysis of Naglu-SapDC treated knockout mice. As shown in FIG. 14 and FIG. 15, intreathecal delivery of Naglu-LIF resulted in a significant reduction in total GAG concentration within the liver and brain, respectively, of Naglu knockout mice, when compared to the vehicle control. The reduction of the total GAG level within the brain was maintained over the entire 3 week treatment period (FIG. 15).

The data also illustrate that, when compared to vehicle control, treatment with Naglu-LIF leads to a strong reduction in the total amount of heparan sulfate accumulation in the brain over the duration of the three week treatment period (FIG. 16). Taken together, all data demonstrate an overall reduction in GAG levels, suggesting Naglu-LIF is able to be efficiently internalized into the lysosome of the cell, where it maintains enzyme activity.

Figure 28:
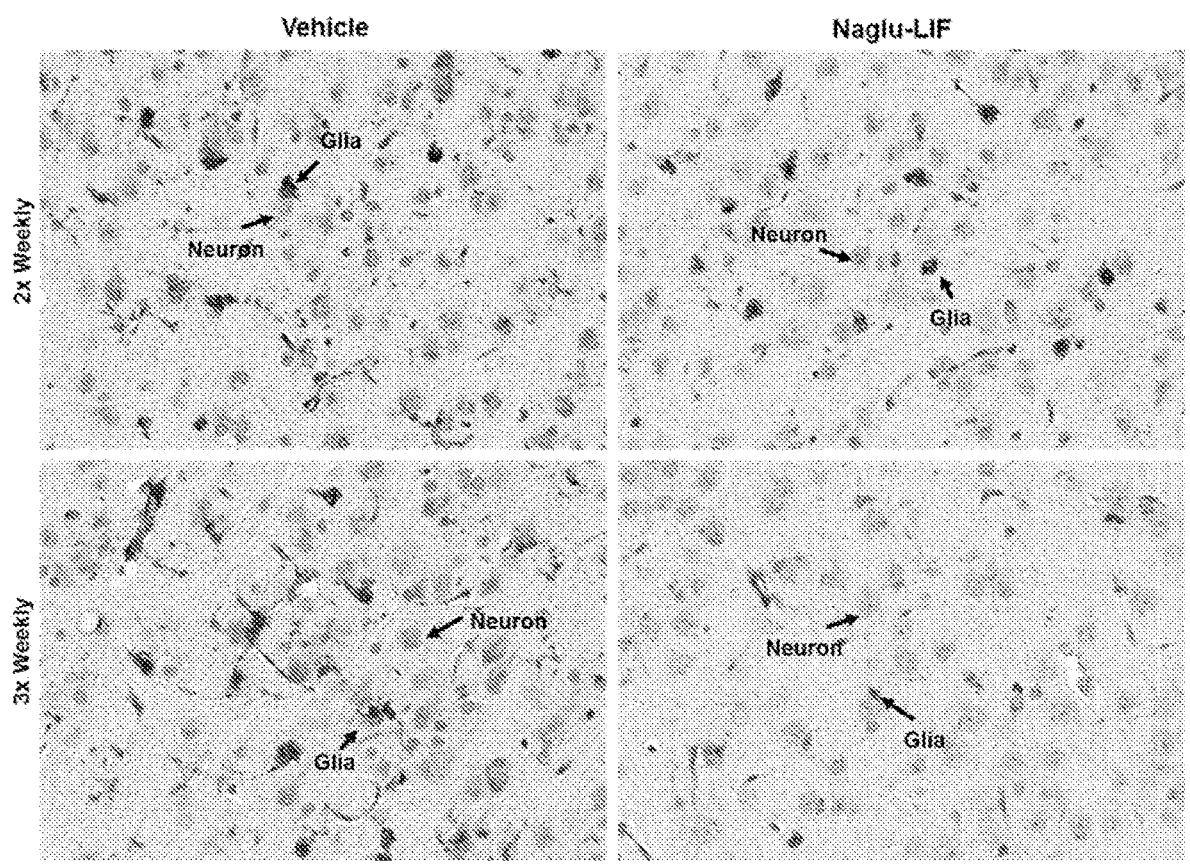
FIG. 28 illustrates LAMP-1 immunohistochemical staining in mouse cerebral cortex tissue following two or three weekly intrathecal injections of vehicle control or Naglu-LIF fusion protein.
Figure 29:
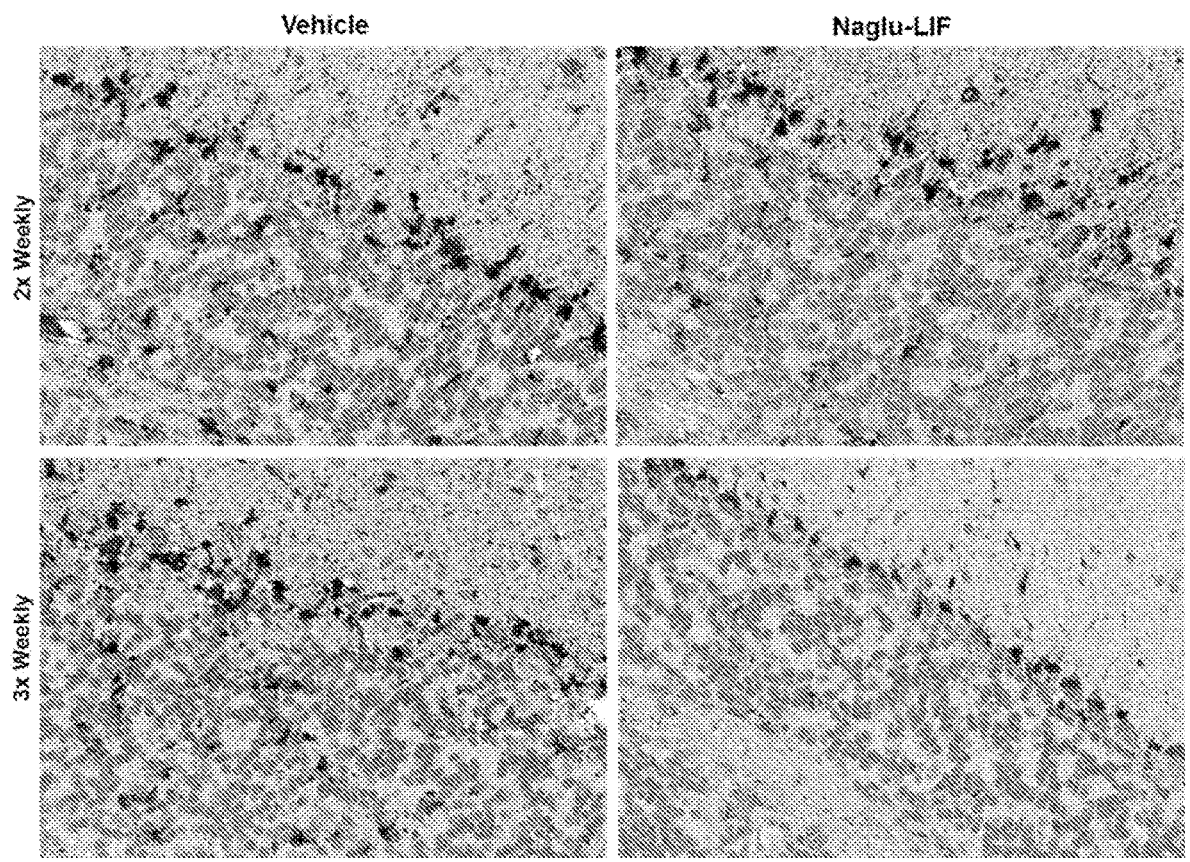
FIG. 29 illustrates LAMP-1 immunohistochemical staining in mouse cerebellum tissue following two or three weekly intrathecal injections of vehicle control or Naglu-LIF fusion protein.
Figure 30:
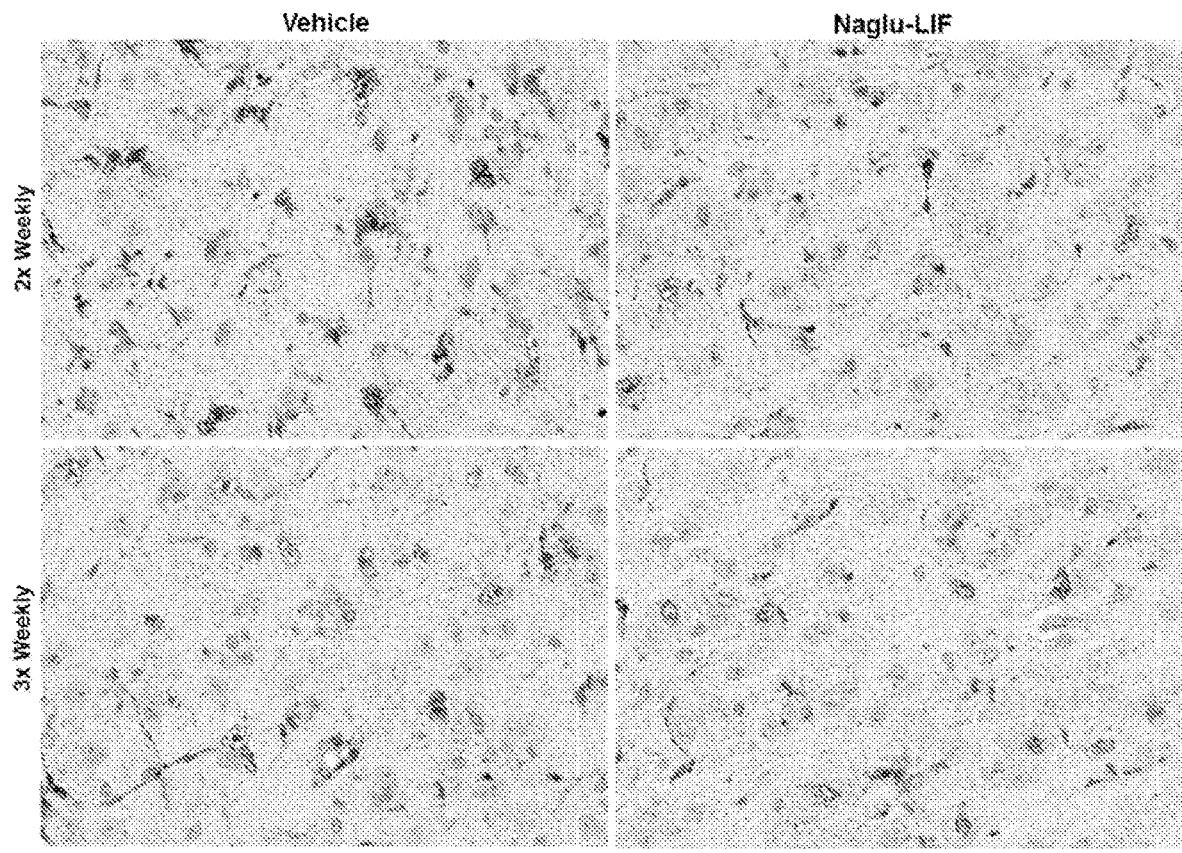
FIG. 30 illustrates LAMP-1 immunohistochemical staining in mouse thalamus tissue following two or three weekly intrathecal injections of vehicle control or Naglu-LIF fusion protein.
Figure 31:
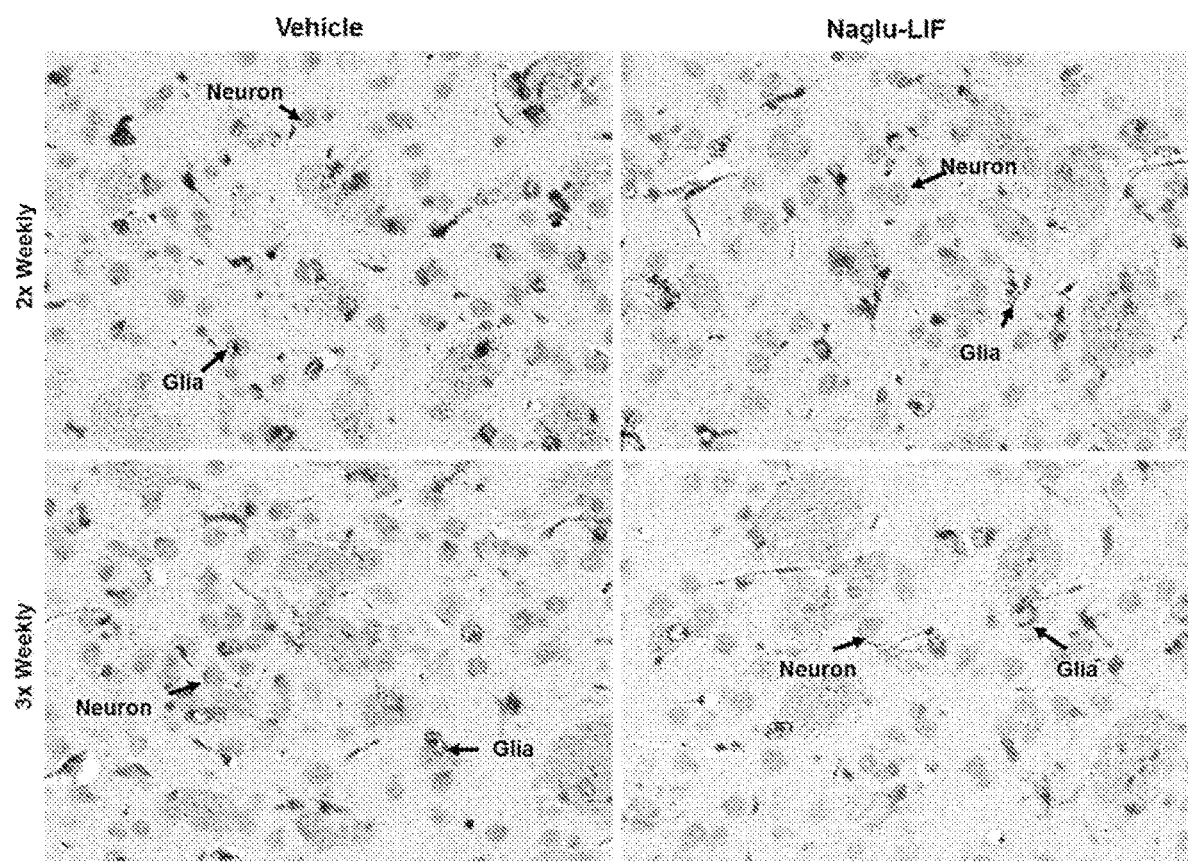
FIG. 31 illustrates LAMP-1 immunohistochemical staining in mouse striatum tissue following two or three weekly intrathecal injections of vehicle control or Naglu-LIF fusion protein.
Figure 32:
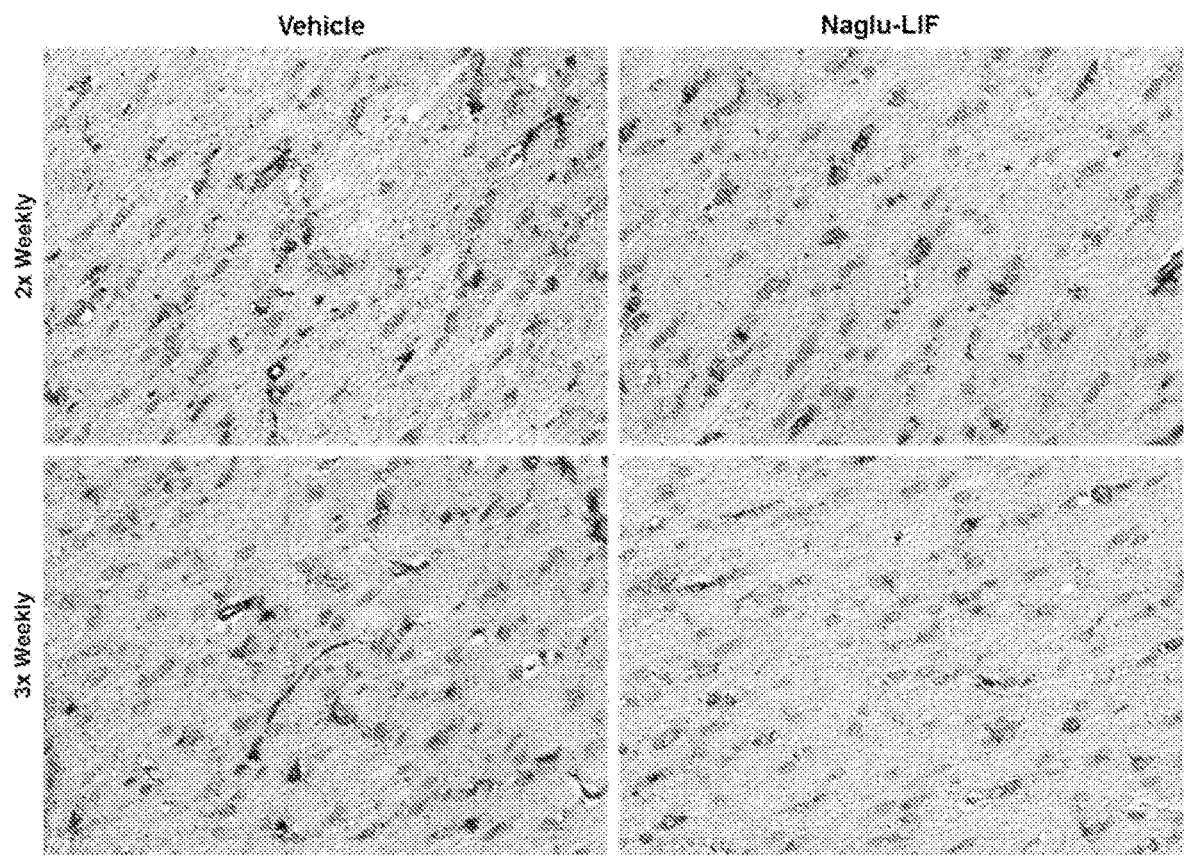
FIG. 32 illustrates LAMP-1 immunohistochemical staining in mouse white matter tissue following two or three weekly intrathecal injections of vehicle control or Naglu-LIF fusion protein.
Figure 33:
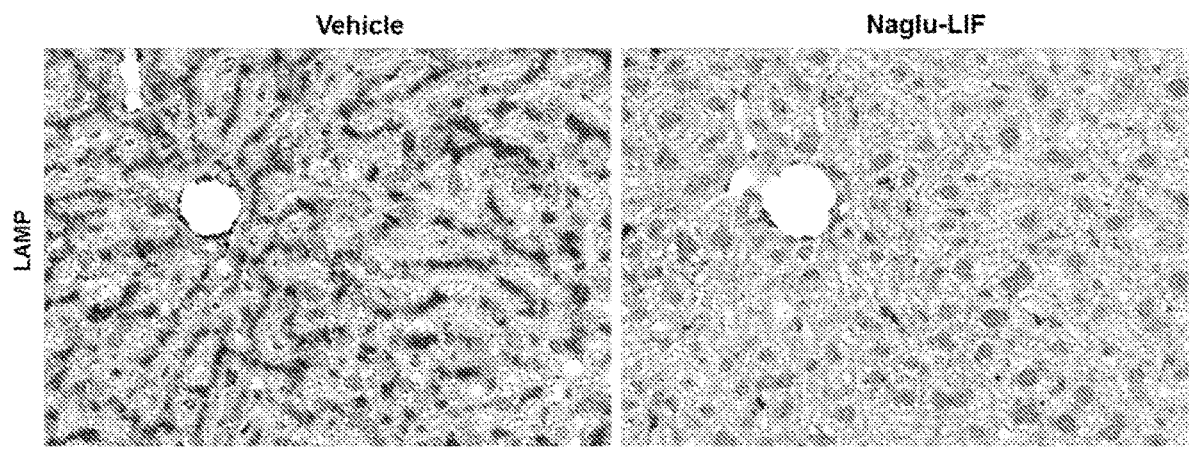
FIG. 33 illustrates LAMP-1 immunohistochemical staining in mouse liver tissue following three weekly intrathecal injections of vehicle control or Naglu-LIF fusion protein.

To further elucidate and confirm the intracellular delivery of Naglu-LIF to lysosomes, the inventors examined the distribution of the lysosomal marker Lamp-1 in each each experimental treatment group. Vehicle control mice, when compared to Naglu-LIF treated mice, showed an increased immunohistochemical staining for Lamp-1 over the entire 3 week period in the apparently enlarged lysosomes of neuronal and glia cells of the cerebral cortex (FIG. 28) cerebellum (FIG. 29), thalamus (FIG. 30), striatum (FIG. 31), white matter (FIG. 32) and liver (FIG. 33).

Figure 34:
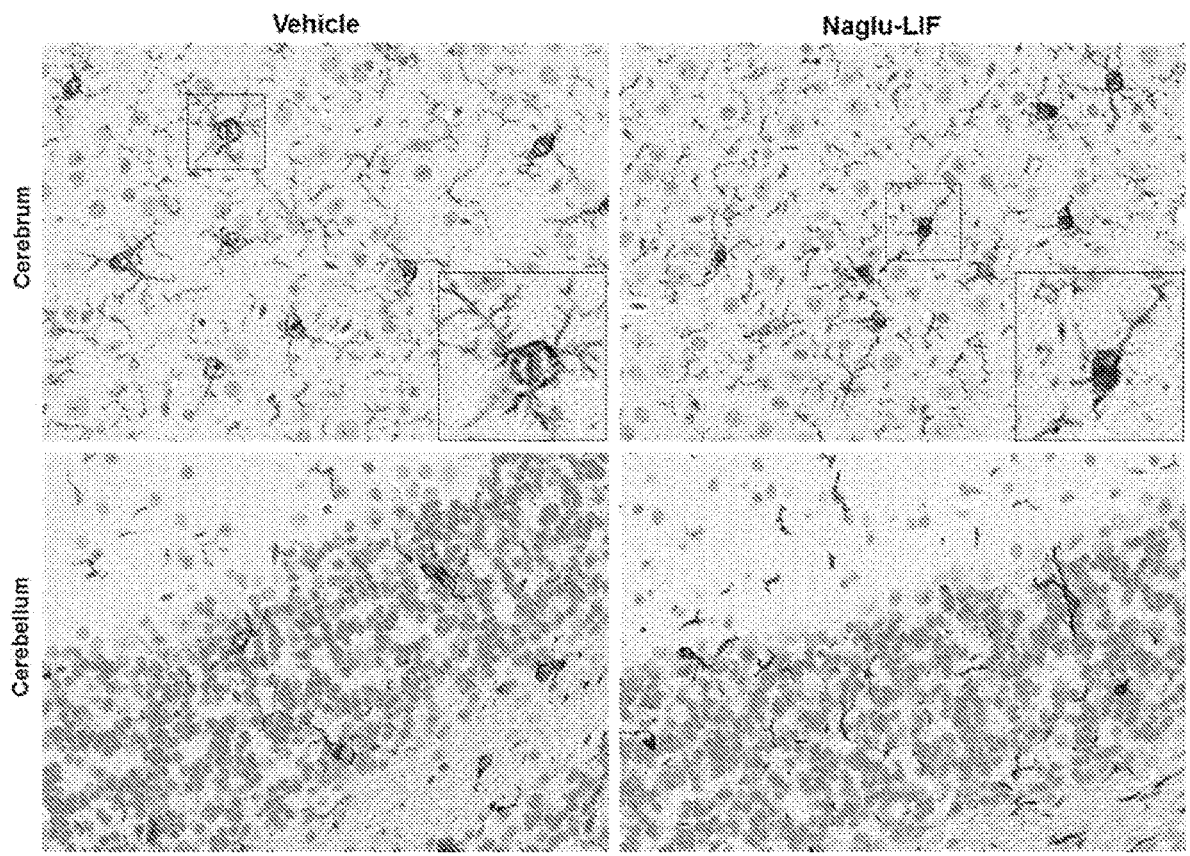
FIG. 34 illustrates immunohistochemical staining of GFAP in mouse cerebrum and cerebellum tissue following three weekly intrathecal injections of vehicle control or Naglu-LIF fusion protein.
Figure 35:
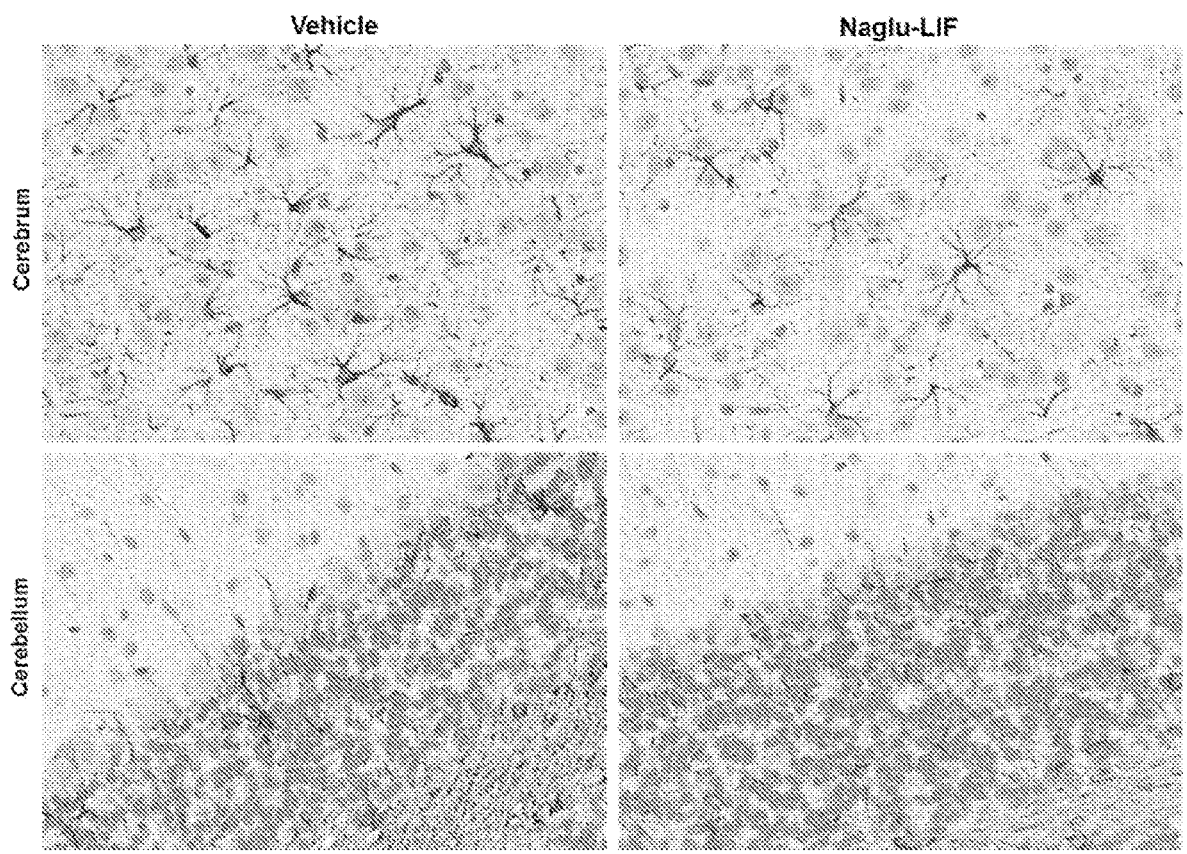
FIG. 35 illustrates immunohistochemical staining of Iba-1 in mouse cerebrum and cerebellum tissue following three weekly intrathecal injections of vehicle control or Naglu-LIF fusion protein.

In addition to Lamp-1, two additional cellular biomarkers were used to further evaluate lysosomal targeting and intracellular delivery of Naglu-LIF. For this study, the ionized calcium-binding adapter molecule 1 (Iba-1) and glial fibrillary acidic protein (GFAP) were chosen as markers. Each protein is a well-established indicator of cellular inflammatory response and can be used to gauge the level and intensity of inflammation in specific cell types. In particular, GFAP staining has been used extensively to demonstrate the size and number of processes in astrocytes, while Iba-1 staining is predominantly used for evaluating microglial cells. As demonstrated in FIG. 34, mice subjected to intrathecal delivery of Naglu-LIF had a reduced amount of GFAP staining for each neuronal tissue examined, indicating reduced lysosome size and a low number of processes. A similar trend was also observed for Iba-1 staining, for each neuronal sample analyzed (FIG. 35).

These data provide strong in vivo support that Naglu-LIF is able to bind the CI-M6P receptor, which facilitates lysosomal targeting and entry in various tissues types. Surprisingly, intrathecal delivery of Naglu-LIF resulted in extensive bioavailability throughout the body, demonstrating localization in neuronal tissue as well as various organ systems of the body, such as the liver. The data further suggest that upon entry into the cell the Naglu-LIF fusion protein maintains enzyme activity and proper function, as demonstrated by the overall reduction in excess accumulation of glucosaminoglycans and heparin sulfate in Naglu knockout mice, which is a hallmark of Sanfilippo type B disease. Given the fusion protein's excellent efficacy, biodistribution and ability to target lysosomal delivery using the CI-M6P receptor mediated pathway, the data strongly suggest that such an approach could be extremely effective for enzyme replacement therapy. Despite the poor M6P-phosphorylation of native Naglu and little to no M6P-phosphorylation of rhNaglu, Naglu-LIF fusion proteins can be M6P-phosphorylated and thus targeted for CI-M6P receptor mediated lysosomal delivery. Our data clearly suggest that that the described lysosomal targeting approach is applicable not only to the treatment of Sanfillipo type B syndrome, but also to the treatment of any other lysosomal storage diseases in which, for example, the native protein lacks a proper M6P-phosphorylation site, or is poorly M6P-phosphorylated due competitive inhibition or steric hindrance of the GNPT enzymatic pocket.

We claim:

1. A nucleic acid encoding a targeted therapeutic fusion protein comprising:
   a lysosomal enzyme, and
   a lysosomal targeting moiety,
   wherein the lysosomal targeting moiety is a prosaposin peptide comprising an amino acid sequence of SEQ ID NO: 4, containing at least one N-linked glycosylation site, and
   wherein the fusion protein, once administered in vivo, results in reduced lysosomal storage.

2. A vector comprising the nucleic acid sequence of claim 1.

3. A host cell comprising the vector of claim 2.

4. The host cell of claim 3, wherein the host cell co-expresses N-acetylglucosamine-1-phosphoTransferase (GNPT).

5. The host cell of claim 4, wherein the host cell comprises an exogenous nucleic acid encoding GNPT.

6. The host cell of claim 4, wherein the host cell has activated expression of endogenous GNPT.

7. A method for producing a targeted therapeutic fusion protein, comprising:

a) culturing cells comprising a nucleic acid of claim 1, wherein the cells co-express N-acetylglucosamine-1-phosphoTransferase (GNPT); and
   b) recovering the fusion protein produced by the cells.

8. The nucleic acid of claim 1, wherein the fusion protein comprises an amino acid sequence at least 90% identical to SEQ ID NO: 18.

9. The nucleic acid of claim 1, wherein the fusion protein comprises an amino acid sequence at least 90% identical to the amino acid sequence of SEQ ID NO. 23.

10. The nucleic acid of claim 1, wherein the lysosomal targeting moiety and the lysosomal enzyme is fused via a linker.

11. The nucleic acid of claim 10, wherein the linker comprises a sequence of

```
                                              (SEQ ID NO.: 15)
GAPGGGGGAAAAAGGGGGAPGGGGGAAAAAGGGGGAPGGGGGAAAAAG
GGGGGAP.
```

* * * * *